(12) United States Patent
Wilson et al.

(10) Patent No.: US 6,270,996 B1
(45) Date of Patent: Aug. 7, 2001

(54) RECOMBINANT ADENOVIRUS AND ADENO-ASSOCIATED VIRUS, CELL LINES AND METHODS OF PRODUCTION AND USE THEREOF

(75) Inventors: James M. Wilson, Gladwyne, PA (US); Krishna J. Fisher, New Orleans, LA (US); Guang-Ping Gao, Havertown, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 09/563,869

(22) Filed: May 3, 2000

Related U.S. Application Data

(63) Continuation of application No. 08/973,334, filed as application No. PCT/US96/10245 on Jun. 4, 1996, which is a continuation-in-part of application No. 08/549,489, filed on Oct. 27, 1995, and a continuation-in-part of application No. 08/462,014, filed on Jun. 5, 1995, now Pat. No. 5,756,283.

(51) Int. Cl.[7] ............. C12N 5/10; C12N 15/35; C12N 15/63; C12P 21/00
(52) U.S. Cl. ............ 435/69.1; 435/455; 435/320.1; 435/457; 435/325; 435/462; 435/463; 435/456
(58) Field of Search .................. 435/5, 6, 69.1, 435/455, 456, 320.1, 457, 325, 366, 462, 463

(56) References Cited

U.S. PATENT DOCUMENTS

| | | | |
|---|---|---|---|
| 4,797,368 | 1/1989 | Carter et al. | 435/320.1 |
| 4,920,209 | 4/1990 | Davis et al. | 435/235.1 |
| 5,139,841 | * 8/1992 | Muzyczka et al. | 435/456 |
| 5,139,941 | 8/1992 | Muzyczka et al. | 435/456 |
| 5,173,414 | 12/1992 | Lebkowski et al. | 435/91.4 |
| 5,252,479 | 10/1993 | Srivastava | 435/235.1 |
| 5,354,678 | 10/1994 | Lebkowski et al. | 435/463 |
| 5,436,146 | 7/1995 | Shenk et al. | 435/457 |
| 5,543,328 | 8/1996 | McClelland et al. | 435/320.1 |
| 5,604,090 | 2/1997 | Alexander et al. | 435/5 |
| 5,622,856 | 4/1997 | Natsoulis | 435/325 |
| 5,707,618 | 1/1998 | Armentano et al. | 424/93.21 |
| 5,753,500 | 5/1998 | Shenk et al. | 435/320.1 |
| 5,756,283 | 5/1998 | Wilson et al. | 435/5 |
| 5,872,154 | 2/1999 | Wilson et al. | 424/154.1 |

FOREIGN PATENT DOCUMENTS

| | | |
|---|---|---|
| 27902/92 | 4/1993 | (AU) . |
| WO91/18088 | 11/1991 | (WO) . |
| WO93/19191 | 9/1993 | (WO) . |
| WO93/24641 | 12/1993 | (WO) . |
| WO94/12649 | 6/1994 | (WO) . |
| WO94/13788 | 6/1994 | (WO) . |
| WO94/17832 | 8/1994 | (WO) . |
| WO94/20517 | 9/1994 | (WO) . |
| WO94/24299 | 10/1994 | (WO) . |
| WO94/26914 | 11/1994 | (WO) . |
| WO94/28152 | 12/1994 | (WO) . |
| WO94/28157 | 12/1994 | (WO) . |
| WO94/28938 | 12/1994 | (WO) . |
| WO95/00655 | 1/1995 | (WO) . |
| WO95/02697 | 1/1995 | (WO) . |
| WO95/06743 | 3/1995 | (WO) . |
| WO95/10623 | 4/1995 | (WO) . |
| WO95/13392 | 5/1995 | (WO) . |
| WO95/20671 | 8/1995 | (WO) . |
| WO95/27071 | 10/1995 | (WO) . |
| WO95/33824 | 12/1995 | (WO) . |
| WO95/34671 | 12/1995 | (WO) . |
| WO96/12030 | 4/1996 | (WO) . |
| WO96/13596 | 5/1996 | (WO) . |
| WO96/13597 | 5/1996 | (WO) . |
| WO96/13598 | 5/1996 | (WO) . |
| WO96/14061 | 5/1996 | (WO) . |
| WO96/18418 | 6/1996 | (WO) . |
| WO96/22378 | 7/1996 | (WO) . |

OTHER PUBLICATIONS

I. Alexander et al, "DNA–Damaging Agents Greatly Increase the Transduction of Nondividing Cells by Adeno–Associated Virus Vectors", *J. Virol.,* 68(12):8282–8287 (Dec., 1994).

F. Collins, "Cystic Fibrosis: Molecular Biology and Therapeutic Implications", *Science,* 256:774–779 (May 8, 1992).

B. Davidson et al, "A Model System for in vivo Gene Transfer into the Central Nervous System Using an Adenoviral Vector", *Nature Genetics,* 3:219–223 (Mar., 1993).

M. Eloit et al, "Construction of a Defective Adenovirus Vector Expressing the Pseudorabies Virus Glycoprotein gp50 and its Use as a Live Vaccine", *J. Gen. Virol.,* 71(10):2425–2431 (Oct., 1990).

J. Engelhardt et al, "Ablation of E2A in Recombinant Adenoviruses Improves Transgene Persistence and Decreases Inflammatory Response in Mouse Liver", *Proc. Natl. Acad. Sci. USA,* 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.,* 4:759–769 (Dec., 1993) [Engelhardt II].

(List continued on next page.)

*Primary Examiner*—David Guzo
(74) *Attorney, Agent, or Firm*—Howson and Howson

(57) ABSTRACT

An adenovirus E1/E4 expressing packaging cell line is provided, which permits the generation of recombinant adenoviruses deleted in both gene regions. A method for enhancing the efficiency of transduction of a recombinant AAV into a target cell is provided by infecting a target cell with a recombinant AAV comprising a selected transgene under the control of regulatory sequences. The infected cell is contacted with an agent which facilitates the conversion of single stranded recombinant virus to its double stranded form.

12 Claims, 11 Drawing Sheets

OTHER PUBLICATIONS

J. Engelhardt et al, "Prolonged Transgene Expression in Cotton Rat Lung with Recombinant Adenoviruses Defective in E2a", *Human Gene Ther.*, 5:1217–1229 (Oct., 1994) [Engelhardt III].

K. Fisher et al, "Biochemical and Functional Analysis of an Adenovirus–Based Ligand Complex for Gene Transfer", *Biochem. J.*, 299:49–58 (Apr. 1, 1994) [Fisher I].

M. Grable et al, "Adenovirus Type 5 Packaging Domain is Composed of a Repeated Element that is Functionally Redundant", *J. Virol.*, 64(5):2047–2056 (May, 1990).

P. Hearing et al, "Identification of a Repeated Sequence Element Required for Efficient Encapsidation of the Adenovirus Type 5 Chromosome", *J. Virol.*, 61(8):2555–2558 (Aug., 1987).

M. Horwitz, "Adenoviridae and Their Replication", *Virology*, 2d edition, ed. B. N. Fields, Raven Press, Ltd., New York, Chapter 60, pp. 1679–1721 (1990).

S. Ishibashi et al, "Hypercholesterolemia in Low Density Lipoprotein Receptor Knockout Mice and its Reversal by Adenovirus–mediated Gene Delivery", *J. Clin. Invest.*, 92:883–893 (Aug., 1993).

M. Kaplitt et al, "Long–term Gene Expression and Phenotypic Correction Using Adeno–associated Virus Vectors in the Mammalian Brain", *Nature Genetics*, 8:148–154 (Oct., 1994).

K. Kozarsky et al, "In Vivo Correction of Low Density Lipoprotein Receptor Deficiency in the Watanabe Heritable Hyperlipidemic Rabbit with Recombinant Adenoviruses", *J. Biol. Chem.*, 269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", *Somatic Cell and Molecular Genetics*, 19(5):449–458 (Sep., 1993) [Kozarsky II].

K. Kozarsky et al, "Gene Therapy: Adenovirus Vectors", *Curr. Opin. Genet. Devel.*, 3:499–503 (Mar., 1993) [Kozarsky III].

C. Laughlin et al., "Cloning of infectious adeno–associated virus genomes in bacterial plasmids," *Gene*, 23:65–73 (Jul., 1983).

J. Logan et al, "Adenovirus Tripartite Leader Sequence Enhances Translation of mRNAs Late After Infection", *Proc. Natl. Acad. Sci. USA*, 81:3655–3659 (Jun., 1984).

B. Roessler et al, "Adenoviral–mediated Gene Transfer to Rabbit Synovium In Vivo", *J. Clin. Invest.*, 92:1085–1092 (Aug., 1993).

D. Russell et al., "Adeno–associated virus vectors preferentially transduce cells in S phase", *Proc. Natl. Acad. Sci. USA*, 91:8915–8919 (Sep., 1994) [Russell I].

M. Rosenfeld et al, "In Vivo Transfer of the Human Cystic Fibrosis Transmembrane Conductance Regulator Gene to the Airway Epithelium", *Cell*, 68:143–155 (Jan. 10, 1992).

R. Samulski et al, "Helper–Free Stocks of Recombinant Adeno–Associated Viruses: Normal Integration Does Not Require Viral Gene Expression", *J. Virol.*, 63(9):3822–3828 (Sep., 1989).

T. Shenk et al, "Genetic Analysis of Adenoviruses", *Current Topics in Microbiol. and Immunol.* 111:1–39 (1984).

W. Smythe et al, "Successful Adenovirus–Mediated Gene Transfer in an In Vivo Model of Human Malignant Mesothelioma", *Ann. Thorac. Surg.*, 57(6):1395–1401 (Jun., 1994).

R. Spessot et al, "Cloning of the Herpes Simplex Virus ICP4 Gene in an Adenovirus Vector: Effects on Adenovirus Gene Expression and Replication," *Virol.*, 168:378–387 (1989).

P. Van Der Vliet et al, "Thermolabile DNA Binding Proteins from Cells Infected with a Temperature–Sensitive Mutant of Adenovirus Defective in Viral DNA Synthesis", *J. Virol.*, 15(2):348–354 (Feb., 1975).

J. Wilson et al, "Vehicles for gene therapy", *Nature*, 365:691–692 (Oct. 21, 1993) [Wilson I].

Y. Yang et al, "MHC Class I–Restricted Cytotoxic T Lymphocytes to Viral Antigens Destroy Hepatocytes in Mice Infected with E1–Deleted Recombinant Adenoviruses", *Immunity*, 1:433–442 (Aug., 1994) [Yang I].

Y. Yang et al, "Cellular Immunity to Viral Antigens Limits E1–Deleted Adenoviruses for Gene Therapy", *Proc. Natl. Acad. Sci. USA*, 91:4407–4411 (May, 1994) [Yang II].

Y. Yang et al, "Inactivation of E2a in Recombinant Adenoviruses Improves the Prospect for Gene Therapy in Cystic Fibrosis", *Nature Genetics*, 7:362–369 (Jul., 1994) [Yang III].

D. Russell et al, "DNA Synthesis and topoisomerase Inhibitors Increase Transduction by Adeno–Associated Virus Vectors", *Proc. Natl. Acad. Sci. USA*, 92:5719–5723 (Jun. 5, 1995) [Russell II].

P. Hermonat et al, "Use of Adeno–Associated Virus as a Mammalian DNA Cloning Vector: Transduction of Neomycin Resistance into Mammalian Tissue Culture Cells", *Proc. Natl. Acad. Sci. USA*, 81:6466–6470 (Oct., 1984).

K. Fisher et al, "Transduction with Recombinant Adeno–Associated Virus for Gene Therapy is Limited by Leading–Strand Synthesis", *J. Virol.*, 70(1):520–532 (Jan., 1996) [Fisher II].

M. Weitzman et al, "Recruitment of Wild–Type and Recombinant Adeno–Associated Virus into Adenovirus Replication Centers", *J. Virol.*, 70(3):1845–1854 (Mar., 1996).

P. Nahreini et al, "Cloning and Integration of DNA Fragments in Human Cells via the Inverted Terminal Repeats of the Adeno–Associated Virus 2 Genome", *Gene*, 119(2):265–272 (1992).

B. Carter, "The Growth Cycle of Adeno–Associated Virus", in *CRC Handbook of Parvoviruses*, ed. P. Tijssen, vol. I, pp. 155–168 (1990).

S. McLaughlin et al, "Adeno–Associated Virus General Transduction Vectors: Analysis of Proviral Structures", *J. Virology*, 62(6):1963–1973 (Jun., 1988).

W. Gunzburg et al, "Virus Vector Design in Gene Therapy", *Molecular Medicine Today*, 1(9):410–417 (Dec., 1995).

J. Schlehofer et al, "Vaccinia Virus, Herpes Simplex VIrus, and Carcinogens Induce DNA Amplification in a Human Cell Line and Support Replication of a Helpervirus Dependent Parvovirus", *Virology*, 152:110–117 (May, 1986).

B. Yakobson et al, "Replication of Adeno–Associated Virus in Synchronized Cells without the Addition of a Helper Virus", *J. Virology*, 61(4):972–981 (Apr., 1987).

R. Boucher et al, "Clinical Protocol—Gene Therapy for Cystic Fibrosis Using E1–Deleted Adenovirus: A Phase I Trial in the Nasal Cavity The University of North Carolina at Chapel Hill", *Human Gene Ther.*, 5:615–639 (May, 1994).

J. Engelhardt et al, "Direct Gene Transfer of Human CFTR into Human Bronchial Epithelia of Xenografts with E1–deleted Adenoviruses", *Nat. Genet.*, 4:27–34 (May, 1993) [Engelhardt IV].

J. Goldstein et al, "Defective Lipoprotein Receptors and Atherosclerosis", *New Engl. J. Med.*, 309(5):288296 (Aug., 1983).

M. Goldman et al, "Expression of $\alpha_v\beta_5$ Integrin Is Necessary for Efficient Adenovirus–Mediated Gene Transfer in the Human Airway", *J. Virol.*, 69:5951–5958 (Oct., 1995) [Goldman I].

M. Goldman et al, "Transfer of the CFTR Gene to the Lung of Nonhuman Primates with E1–Deleted, E2a–Defective Recombinant Adenoviruses: A Preclinical Toxicology Study", *Human Gene Therapy*, 6:839–851 (Jul., 1995) [Goldman II].

M. Goldman et al, "Gene therapy in a xenograft model of cystic fibrosis lung correct chloride transport more effectively than the sodium detect", *Nature Genetics*, 9:126–131 (Feb., 1995) [Goldman III].

M. Grossman et al, "Towards Liver–Directed Gene Therapy: Retrovirus–Mediated Gene Transfer into Human Hepatocytes", *Somatic Cell and Molec. Genet.*, 17(6):601–607 (Nov., 1991).

B. Grubb et al, "Inefficient gene transfer by adenovirus vector to cystic fibrosis airway epithelia of mice and humans", *Nature*, 371:802–806 (Oct. 27, 1994).

S. Ishibashi et al, "Massive Xanthomatosis and Atherosclerosis in Cholesterol–fed Low Density Lipoprotein Receptor–negative Mice", *J. Clin. Invest.*, 93:1885–1893 (May, 1994) [Ishibashi I].

M. Knowles et al, "A Controlled Study of Adenoviral–Vector–Mediated Gene Transfer in the Nasal Epithelium of Patients with Cystic Fibrosis", *N. Engl. J. Med.*, 333(13):823–831 (Sep., 1995).

J. Pilewski et al, "Adenovirus–mediated gene transfer to human bronchial submucosal glands using xenografts", *Amer. J. Physiol: Lung, Cell and Mole Physiol.*, 268:L657–L665 (Apr., 1995) [Pilewski I].

J. Pilewski et al, "ICAM–1 Expression on Bronchial Epithelium after Recombinant Adenovirus Infection", *Am J. Respir. Cell Mol. Biol.*, 12:142–148 (Feb., 1995) [Pilewski II].

T. A. G. Smith et al, "Adenovirus mediated expression of therapeutic plasma levels of human factor IX in mice", *Nature Genetics*, 5:397–402 (Dec., 1993).

K. Tanzawa et al, "WHHL–Rabbit: A Low Density Lipoprotein Receptor–Deficient Animal Model for Familial Hypercholesterolemia", *FEBS Letters*, 118(1):81–84 (Aug., 1980).

Y. Watanabe et al, "Serial Inbreeding of Rabbits with Hereditary Hyperlipidemia (WHHL–Rabbit)", *Atherosclerosis*, 36:261–268 (Jan., 1980).

J. Wilson et al, "Correction of the Genetic Defect in Hepatocytes from the Watanabe Heritable Hyperlipidemic Rabbit", *Proc. Natl. Acad. Sci. USA*, 85:4421–4425 (Jun., 1988) [Wilson II].

J. Wilson et al, "Research Article—Transplantation of Allogeneic Hepatocytes into LDL Receptor Deficient Rabbits Lead to Transient Improvement in Hypercholesterolemia", *Clin. Biotechnology*, 3:21–26 (Feb. 28, 1991) [Wilson III].

C. Wu et al, "Targeting Genes: Delivery and Persistent Expression of a Foreign Gene Driven by Mammalian Regulatory Elements in Vivo", *J. Biol. Chem.*, 264(29):16985–16987 (Oct. 15, 1989).

Y. Yang et al, "Recombinant IL–12 Prevents Formation of Blocking IgA Antibodies to Recombinant Adenovirus and Allows Repeated Gene Therapy to Mouse Lung", *Nat. Med.*, 1(9):890–893 (Sep., 1995) [Yang IV].

Y. Yang et al, "Upregulation of Class I MHC Antigens by Interferon–$\gamma$ is Necessary for the T Cell–Mediated Elimination of Recombinant Adenovirus Infected Hepatocytes In Vivo", *Proc. Natl. Acad. Sci. USA*, 92:7257–7261 (Aug.. 1995) [Yang V].

Y. Yang et al, "Cellular and Humoral Immune Responses to Viral Antigens Create Barriers to Lung–Directed Gene Therapy with Recombinant Adenoviruses", *J. Virol.*, 69(4):2004–2015 (Apr., 1995) [Yang VI].

Y. Yang et al, "Clearance of Adenovirus–Infected Hepatocytes by MHC Class I–Restricted CD4+ CTLs in Vivo", *J. Immunol.*, 155:2564–2570 (Jun., 1995) [Yang VII].

K. Berkner, "Development of Adenovirus Vectors for the Expression of Heterologous Genes", *Biotechniques*, 6(7):616–629 (1988) [Berkner I].

E. Bridge et al, "Redundant Control of Adenovirus Late Gene Expression by Early Region 4", *J. Virol.*, 63(2):631–638 (Feb., 1989) [Bridge I].

Y. Dai et al, "Cellular and Humoral Immune Responses to Adenoviral Vectors Containing Factor IX Gene: Tolerization of Factor IX and Vector Antigens Allows for Long–Term Expression", *Proc. Natl. Acad. Sci. USA*, 92:1401–1405 (Feb., 1995).

Q. Wang et al, "A Packaging Cell Line for Propagation of Recombinant Adenovirus Vectors Containing Two Lethal Gene–Region Deletions", *Gene Therapy*, 2:775–783 (Dec. 19, 1995).

R. Hirt et al, "Inducible Protein Expression Using a Glucocortocoid–Sensitive Vector", *Methods in Cell Biology*, 43:247–262 (1994).

D. Weinberg et al, "A Cell Line that Supports the Growth of a Defective Early Region 4 Deletion Mutant of Human Adenovirus Type 2", *Proc. Natl. Acad. Sci. USA*, 80:5383–5386 (Sep., 1983).

D. Armentano et al, "Characterization of an Adenovirus Gene Transfer Vector Containing an E4 Deletion", *Human Gene Therapy*, 6:1343–1353 (Oct., 1995).

E. Bridge et al, "Adenovirus Early Region 4 and Viral DNA Synthesis", *Virology*, 193:794–801 (1993) [Bridge II].

K. Berkner, "Expression of Heterologous Sequences in Adenoviral Vectors", *Current Topics in Microbiology and Immunology*, 158:39–66 (1992) [Berkner II].

K. Ohman et al, "Two Adenovirus Proteins with Redundant Activities in Virus Growth Facilitates Tripartite Leader mRNA Accumulation", *Virology*, 194:50–58 (1993).

J. Wilson et al, "Clinical Protocol—Gene Therapy of Cystic Fibrosis Lung Disease Using E1 Deleted Adenoviruses: A Phase I Trial", *Human Gene Therapy*, 5:501–519 (1994) [Wilson V].

R. Crystal, "Transfer of Genes to Humans: Early Lessions and Obstacles to Success", *Science*, 270:404–409 (Oct. 20, 1995).

S. Karlsson, "Treatment of Genetic Defects in Hematopoietic Cell Function by Gene Transfer", *Blood*, 78(10):2481–2492 (Nov. 15, 1991).

J–Y. Dong et al, "Systematic Analysis of Repeated Gene Delivery into Animal Lungs with a Recombinant Adenovirus Vector", *Human Gene Therapy*, 7:319–331 (Feb. 10, 1996).

A. Scaria et al, "Complementation of a Human Adenovirus Early Region 4 Deletion Mutant in 293 Cells Using Adenovirus–Polylysine–DNA Complexes", *Gene Therapy*, 2:295–298 (1995).

E. Marshall, "Less Hype, More Biology Needed for Gene Therapy", *Science*, 270:1751 (Dec. 15, 1995) [Marshall I].

A. Coghlan, "Gene Dream Fades Away", *New Scientist*, 145:14–15 (Nov. 25, 1995).

E. Marshall, "Gene Therapy's Growing Pains", *Science*, 269:1050–1055 (Aug. 25, 1995) [Marshall II].

S. Orkin et al, "Report and Recommendations of the Panel to Assess the NIH Investment in Research on Gene Therapy", (Dec. 7, 1995).

I. Verma et al, "Gene Therapy—Promises, Problems and Prospects", *Nature*, 389:239–242 (Sep. 18, 1997).

G. Ross et al, "Gene Therapy in the United States: A Five–Year Status Report", *Human Gene Therapy*, 7:1781–1790 (Sep. 10, 1996).

* cited by examiner

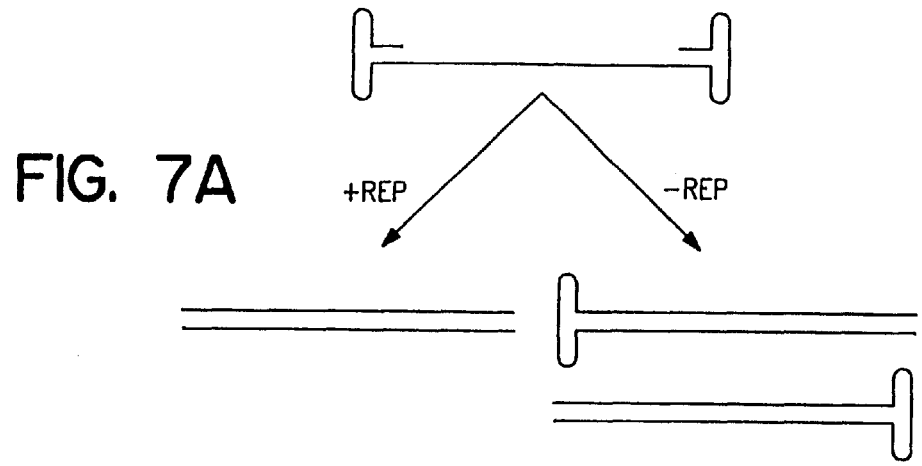
FIG. 7A
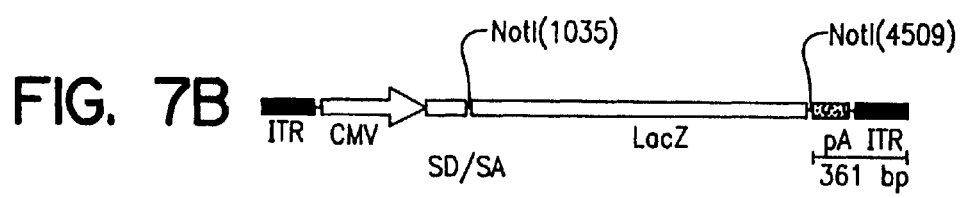
FIG. 7B
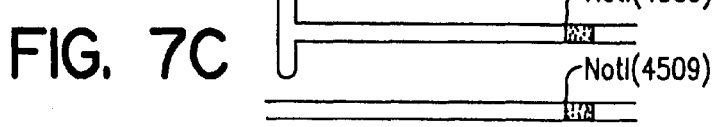
FIG. 7C
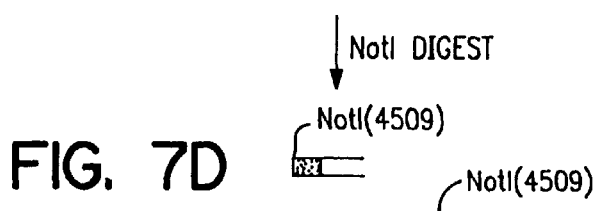
FIG. 7D
FIG. 7E
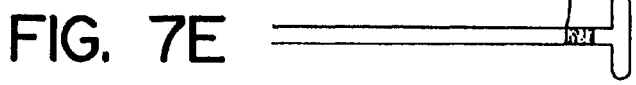
FIG. 7F
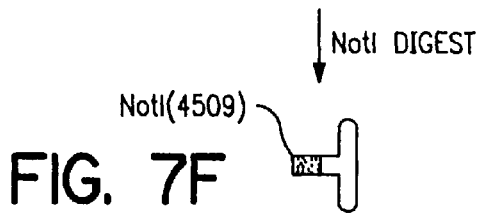

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 3653 base pairs
      (B) TYPE: nucleic acid
      (C) STRANDEDNESS: double
      (D) TOPOLOGY: not relevant (ii) MOLECULE TYPE: cDNA (ix) FEATURE:
      (A) NAME/KEY: CDS
      (B) LOCATION: 1521..2405

(xi) SEQUENCE DESCRIPTION: SEQ ID NO: 1:

```
CTGCATGTGT CAGAGGTTTT CACCGTCATC ACCGAAACGC GCGAGGCAGC           50

AAGCTTGGCA GAAATGGTTG AACTCCCGAG AGTGTCCTAC ACCTAGGGGA          100

GAAGCAGCCA AGGGGTTGTT TCCCACCAAG GACGACCCGT CTGCGCACAA          150

ACGGATGAGC CCATCAGACA AAGACATATT CATTCTCTGC TGCAAACTTG          200

GCATAGCTCT GCTTTGCCTG GGGCTATTGG GGGAAGTTGC GGTTCGTGCT          250

CGCAGGGCTC TCACCCTTGA CTCTTTCAAT AATAACTCTT CTGTGCAAGA          300

TTACAATCTA AACAATTCGG AGAACTCGAC CTTCCTCCTG AGGCAAGGAC          350

CACAGCCAAC TTCCTCTTAC AAGCCGCATC GATTTTGTCC TTCAGAAATA          400

GAAATAAGAA TGCTTGCTAA AAATTATATT TTTACCAATA AGACCAATCC          450

AATAGGTAGA TTATTAGTTA CTATGTTAAG AAATGAATCA TTATCTTTTA          500
```

-continued

```
GTACTATTTT TACTCAAATT CAGAAGTTAG AAATGGGAAT AGAAAATAGA        550

AAGAGACGCT CAACCTCAAT TGAAGAACAG GTGCAAGGAC TATTGACCAC        600

AGGCCTAGAA GTAAAAAAGG GAAAAAAGAG TGTTTTTGTC AAAATAGGAG        650

ACAGGTGGTG GCAACCAGGG ACTTATAGGG GACCTTACAT CTACAGACCA        700

ACAGATGCCC CCTTACCATA TACAGGAAGA TATGACTTAA ATTGGGATAG        750

GTGGGTTACA GTCAATGGCT ATAAAGTGTT ATATAGATCC CTCCCCTTTC        800

GTGAAAGACT CGCCAGAGCT AGACCTCCTT GGTGTATGTT GTCTCAAGAA        850

AAGAAAGACG ACATGAAACA ACAGGTACAT GATTATATTT ATCTAGGAAC        900

AGGAATGCAC TTTTGGGGAA AGATTTTCCA TACCAAGGAG GGGACAGTGG        950

CTGGACTAAT AGAACATTAT TCTGCAAAAA CTTATGGCAT GAGTTATTAT       1000

GATTAGCCTT GATTTGCCCA ACCTTGCGGT TCCCAAGGCT TAAGTAAGTT       1050

TTTGGTTACA AACTGTTCTT AAAACAAGGA TGTGAGACAA GTGGTTTCCT       1100

GACTTGGTTT GGTATCAAAG GTTCTGATCT GAGCTCTGAG TGTTCTATTT       1150

TCCTATGTTC TTTTGGAATT TATCCAAATC TTATGTAAAT GCTTATGTAA       1200

ACCAAGATAT AAAAGAGTGC TGATTTTTTG AGTAAACTTG CAACAGTCCT       1250

AACATTCACC TCTTGTGTGT TTGTGTCTGT TCGCCATCCC GTCTCCGCTC       1300

GTCACTTATC CTTCACTTTC CAGAGGGTCC CCCCGCAGAC CCCGGCGACC       1350

CTCAGGTCGG CCGACTGCGG CAGCTGGCGC CCGAACAGGG ACCCTCGGAT       1400

AAGTGACCCT TGTCTTTATT TCTACTATTT TGTGTTCGTC TTGTTTTGTC       1450

TCTATCTTGT CTGGCTATCA TCACAAGAGC GGAACGGACT CACCTCAGGG       1500

AACCAAGCTA GCCCAATTCG ATGACTACGT CCGGCGTTCC ATTTGGCATG       1550

ACACTACGAC CAACACGATC TCGGTTGTCT CGGCGCACTC CGTACAGTAG       1600

GGATCGTCTA CCTCCTTTTG AGACAGAAAC CCGCGCTACC ATACTGGAGG       1650

ATCATCCGCT GCTGCCCGAA TGTAACACTT TGACAATGCA CAACGTGAGT       1700

TACGTGCGAG GTCTTCCCTG CAGTGTGGGA TTTACGCTGA TTCAGGAATG       1750

GGTTGTTCCC TGGGATATGG TTCTAACGCG GGAGGAGCTT GTAATCCTGA       1800

GGAAGTGTAT GCACGTGTGC CTGTGTTGTG CCAACATTGA TATCATGACG       1850

AGCATGATGA TCCATGGTTA CGAGTCCTGG GCTCTCCACT GTCATTGTTC       1900

CAGTCCCGGT TCCCTGCAGT GTATAGCCGG CGGGCAGGTT TTGGCCAGCT       1950

GGTTTAGGAT GGTGGTGGAT GGCGCCATGT TTAATCAGAG GTTTATATGG       2000

TACCGGGAGG TGGTGAATTA CAACATGCCA AAAGAGGTAA TGTTTATGTC       2050

CAGCGTGTTT ATGAGGGGTC GCCACTTAAT CTACCTGCGC TTGTGGTATG       2100

ATGGCCACGT GGGTTCTGTG GTCCCCGCCA TGAGCTTTGG ATACAGCGCC       2150

TTGCACTGTG GGATTTTGAA CAATATTGTG GTGCTGTGCT GCAGTTACTG       2200

TGCTGATTTA AGTGAGATCA GGGTGCGCTG CTGTGCCCGG AGGACAAGGC       2250

GCCTTATGCT GCGGGCGGTG CGAATCATCG CTGAGGAGAC CACTGCCATG       2300

TTGTATTCCT GCAGGACGGA GCGGCGGCGG CAGCAGTTTA TTCGCGCGCT       2350

GCTGCAGCAC CACCGCCCTA TCCTGATGCA CGATTATGAC TCTACCCCCA       2400

TGTAGGGATC CAAGCTTGCG GGCGCATCGA TGATATCAAG CTTGCATGCC       2450
```

-continued

```
TGCAGGTCGA CTCTAGAGGA TCCCGGGTGG NATCCCTGTG ACCCCTCCCC      2500

AGTGCCTCTC CTGGCCCTGG AAGTTGGCAC TCCAGTGCCC ACCAGCCTTG      2550

TCCTAATAAA ATTAAGTTGN ATCATTTTGT CTGACTAGGT GTCCTTCTAT      2600

AATATTATGG GGTGGAGGGG GGTGGTATGG AGCAANGGGN AANTTGGNAA      2650

GACAANCTGT AGGGCCTGCG GGGTCTATTG GAACAAGCT GGAGTGCAGT       2700

GGCACAATCT TGGCTCACTG CAATCTCCGC CTCCTGGGTT CAAGCGATTC      2750

TCCTGCCTCA GACTCCCGAG TTGTTGGGAT TCCAGGCATG CATGACCAGG      2800

CTCAGATAAT TTTTGTTTTT TGGTAGAGA CGGGGTTTCA CCATATTGGN       2850

CAGGCTGGTC TCCAACTCCT AATCTCAGGT GATCTNCCCA CCTTGGCCTC      2900

CCAAATTGCT GGGATTACAG GNGTGAACCA CTGNTCCCTT CCCTGTCCTT      2950

CTGATTTTAA AATAACTATA CCAGCAGGAG GACGTCCAGA CACAGCATAG      3000

GCTACCTGGC CATGCCCAAC CGGTGGGACA TTTGAGTTGC TTGCTTGGCA      3050

CTGTCCTCTC ATGCGTTGGG TCCACTCAGT AGATGCCTGT TGAATTGGGT      3100

ACGCGGCCAG CTTGGCTGTG AATGTGTGT CAGTTAGGGT GTGGAAAGTC       3150

CCCAGGCTCC CCAGCAGGCA GAAGTATGCA AAGCATGCAT CTCAATTAGT      3200

CAGCAACCAG GTGTGGAAAG TCCCCAGGCT CCCCAGCAGG CAGAAGTATG      3250

CAAAGCATGC ATCTCAATTA GTCAGNAACC ATAGNCCCGC CCCTAACTCC      3300

GTCCATCCCG GCCCTAACTC NGGCCAGTTC CGACCNTNCT CCGGCNNATG      3350

GNTGAGTAAT TTGCNNGATT TATGCAGNGG GCGAGGNCGC CTCGGGCTCT      3400

GAGNTNTTCC AGAAGTAGTG AGGAGGCTTT NNTGGTGGAA TTGATCAGCT      3450

TGGGATCTGA TCAAGAGACA GGATGAGGAT CGNNNCGNAT GATTGAACAA      3500

GATGGGTTGC ACGGAGGTTC TCCGGNCGCT TGGGTGGGGA GGNTATTCGG      3550

NTATTNTTGG TGNACAACAG NNAAACGGNT GTTCTGATGC CGCCGCGTTC      3600

NCGCTTTCAG NGCAGGGGGG CCCCCCTTCT NTTGAGANNA GCNCCCCTTN      3650

TTG                                                         3653
```

(2) INFORMATION FOR SEQ ID NO: 2:

(i) SEQUENCE CHARACTERISTICS:
        (A) LENGTH: 294 amino acids
        (B) TYPE: amino acid
        (C) STRANDEDNESS: <Unknown>
        (D) TOPOLOGY: not relevant (ii) MOLECULE TYPE: protein (xi) SEQUENCE DESCRIPTION: SEQ ID NO: 2:

```
Met Thr Thr Ser Gly Val Pro Phe Gly Met Thr Leu Arg Pro Thr Arg
 1               5                  10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Pro
65                  70                  75                  80

Trp Asp Met Val Leu Thr Arg Glu Glu Leu Val Ile Leu Arg Lys Cys
```

```
               85                  90                  95
Met His Val Cys Leu Cys Cys Ala Asn Ile Asp Ile Met Thr Ser Met
                100                 105                 110

Met Ile Tyr Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
            165                 170                 175

Ser Ser Val Phe Met Arg Gly Arg His Leu Ile Tyr Leu Arg Tyr Trp
        180                 185                 190

Tyr Asp Gly His Val Gly Ser Val Pro Ala Met Ser Phe Gly Tyr
            195                 200                 205

Ser Ala Leu His Cys Gly Ile Leu Asn Asn Ile Val Val Leu Cys Cys
    210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
            245                 250                 255

Thr Thr Ala Met Leu Tyr Ser Cys Arg Thr Glu Arg Arg Gln Gln
            260                 265                 270

Phe Ile Arg Ala Leu Leu Gln His His Arg Pro Ile Leu Met His Asp
        275                 280                 285

Tyr Asp Ser Thr Pro Met
    290

(2) INFORMATION FOR SEQ ID NO: 3:

(i) SEQUENCE CHARACTERISTICS:
        (A) LENGTH: 35408 base pairs
        (B) TYPE: nucleic acid
        (C) STRANDEDNESS: not relevant
        (D) TOPOLOGY: not relevant (ii) MOLECULE TYPE: other nucleic acid (xi) SEQUENCE DESCRIPTION: SEQ ID NO: 3:

CATCATCAAT AATATACCTT ATTTTGGATT GAAGCCAATA TGATAATGAG            50

GGGGTGGAGT TTGTGACGTG GCGCGGGGCG TGGGAACGGG GCGGGTGACG           100

TAGTAGTGTG GCGGAAGTGT GATGTTGCAA GTGTGGCGGA ACACATGTAA           150

GCGACGGATG TGGCAAAAGT GACGTTTTTG GTGTGCGCCG GTGTACACAG           200

GAAGTGACAA TTTTCGCGCG GTTTTAGGCG GATGTTGTAG TAAATTTGGG           250

CGTAACCGAG TAAGATTTGG CCATTTTCGC GGGAAAACTG AATAAGAGGA           300

AGTGAAATCT GAATAATTTT GTGTTACTCA TAGCGCGTAA TATTTGTCTA           350

GGGAGATCAG CCTGCAGGTC GTTACATAAC TTACGGTAAA TGGCCCGCCT           400

GGCTGACCGC CCAACGACCC CCGCCCATTG ACGTCAATAA TGACGTATGT           450

TCCCATAGTA ACGCCAATAG GGACTTTCCA TTGACGTCAA TGGGTGGAGT           500

ATTTACGGTA AACTGCCCAC TTGGCAGTAC ATCAAGTGTA TCATATGCCA           550

AGTACGCCCC CTATTGACGT CAATGACGGT AAATGGCCCG CCTGGCATTA           600

TGCCCAGTAC ATGACCTTAT GGGACTTTCC TACTTGGCAG TACATCTACT           650
```

-continued

```
CGAGGCCACG TTCTGCTTCA CTCTCCCCAT CTCCCCCCCC TCCCCACCCC        700

CAATTTTGTA TTTATTTATT TTTTAATTAT TTTGTGCAGC GATGGGGGCG        750

GGGGGGGGGG GGGGCGCGC GCCAGGCGGG GCGGGGCGGG GCGAGGGGCG         800

GGGCGGGGCG AGGCGGAGAG GTGCGGCGGC AGCCAATCAG AGCGGCGCGC        850

TCCGAAAGTT TCCTTTTATG GCGAGGCGGC GGCGGCGGCG GCCCTATAAA        900

AAGCGAAGCG CGCGGCGGGC GGGAGCGGGA TCAGCCACCG CGGTGGCGGC        950

CGCAATTCCC GGGGATCGAA AGAGCCTGCT AAAGCAAAAA AGAAGTCACC       1000

ATGTCGTTTA CTTTGACCAA CAAGAACGTG ATTTTCGTTG CCGGTCTGGG       1050

AGGCATTGGT CTGGACACCA GCAAGGAGCT GCTCAAGCGC GATCCCGTCG       1100

TTTTACAACG TCGTGACTGG GAAAACCCTG GCGTTACCCA ACTTAATCGC       1150

CTTGCAGCAC ATCCCCCTTT CGCCAGCTGG CGTAATAGCG AAGAGGCCCG       1200

CACCGATCGC CCTTCCCAAC AGTTGCGCAG CCTGAATGGC GAATGGCGCT       1250

TTGCCTGGTT TCCGGCACCA GAAGCGGTGC CGGAAAGCTG GCTGGAGTGC       1300

GATCTTCCTG AGGCCGATAC TGTCGTCGTC CCCTCAAACT GGCAGATGCA       1350

CGGTTACGAT GCGCCCATCT ACACCAACGT AACCTATCCC ATTACGGTCA       1400

ATCCGCCGTT TGTTCCCACG GAGAATCCGA CGGGTTGTTA CTCGCTCACA       1450

TTTAATGTTG ATGAAAGCTG GCTACAGGAA GGCCAGACGC GAATTATTTT       1500

TGATGGCGTT AACTCGGCGT TCATCTGTG GTGCAACGGG CGCTGGGTCG        1550

GTTACGGCCA GGACAGTCGT TTGCCGTCTG AATTTGACCT GAGCGCATTT       1600

TTACGCGCCG GAGAAAACCG CCTCGCGGTG ATGGTGCTGC GTTGGAGTGA       1650

CGGCAGTTAT CTGGAAGATC AGGATATGTG GCGGATGAGC GGCATTTTCC       1700

GTGACGTCTC GTTGCTGCAT AAACCGACTA CACAAATCAG CGATTTCCAT       1750

GTTGCCACTC GCTTTAATGA TGATTTCAGC CGCGCTGTAC TGGAGGCTGA       1800

AGTTCAGATG TGCGGCGAGT TGCGTGACTA CCTACGGGTA ACAGTTTCTT       1850

TATGGCAGGG TGAAACGCAG GTCGCCAGCG GCACCGCGCC TTTCGGCGGT       1900

GAAATTATCG ATGAGCGTGG TGGTTATGCC GATCGCGTCA CACTACGTCT       1950

GAACGTCGAA AACCCGAAAC TGTGGAGCGC CGAAATCCCG AATCTCTATC       2000

GTGCGGTGGT TGAACTGCAC ACCGCCGACG GCACGCTGAT TGAAGCAGAA       2050

GCCTGCGATG TCGGTTTCCG CGAGGTGCGG ATTGAAAATG GTCTGCTGCT       2100

GCTGAACGGC AAGCCGTTGC TGATTCGAGG CGTTAACCGT CACGAGCATC       2150

ATCCTCTGCA TGGTCAGGTC ATGGATGAGC AGACGATGGT GCAGGATATC       2200

CTGCTGATGA AGCAGAACAA CTTTAACGCC GTGCGCTGTT CGCATTATCC       2250

GAACCATCCG CTGTGGTACA CGCTGTGCGA CCGCTACGGC CTGTATGTGG       2300

TGGATGAAGC CAATATTGAA ACCCACGGCA TGGTGCCAAT GAATCGTCTG       2350

ACCGATGATC CGCGCTGGCT ACCGGCGATG AGCGAACGCG TAACGCGAAT       2400

GGTGCAGCGC GATCGTAATC ACCCGAGTGT GATCATCTGG TCGCTGGGGA       2450

ATGAATCAGG CCACGGCGCT AATCACGACG CGCTGTATCG CTGGATCAAA       2500

TCTGTCGATC CTTCCCGCCC GGTGCAGTAT GAAGGCGGCG GAGCCGACAC       2550

CACGGCCACC GATATTATTT GCCCGATGTA CGCGCGCGTG GATGAAGACC       2600
```

| | |
|---|---|
| AGCCCTTCCC GGCTGTGCCG AAATGGTCCA TCAAAAAATG GCTTTCGCTA | 2650 |
| CCTGGAGAGA CGCGCCCGCT GATCCTTTGC GAATACGCCC ACGCGATGGG | 2700 |
| TAACAGTCTT GGCGGTTTCG CTAAATACTG GCAGGCGTTT CGTCAGTATC | 2750 |
| CCCGTTTACA GGGCGGCTTC GTCTGGGACT GGGTGGATCA GTCGCTGATT | 2800 |
| AAATATGATG AAAACGGCAA CCCGTGGTCG GCTTACGGCG GTGATTTTGG | 2850 |
| CGATACGCCG AACGATCGCC AGTTCTGTAT GAACGGTCTG GTCTTTGCCG | 2900 |
| ACCGCACGCC GCATCCAGCG CTGACGGAAG CAAAACACCA GCAGCAGTTT | 2950 |
| TTCCAGTTCC GTTTATCCGG GCAAACCATC GAAGTGACCA GCGAATACCT | 3000 |
| GTTCCGTCAT AGCGATAACG AGCTCCTGCA CTGGATGGTG GCGCTGGATG | 3050 |
| GTAAGCCGCT GGCAAGCGGT GAAGTGCCTC TGGATGTCGC TCCACAAGGT | 3100 |
| AAACAGTTGA TTGAACTGCC TGAACTACCG CAGCCGGAGA GCGCCGGGCA | 3150 |
| ACTCTGGCTC ACAGTACGCG TAGTGCAACC GAACGCGACC GCATGGTCAG | 3200 |
| AAGCCGGGCA CATCAGCGCC TGGCAGCAGT GGCGTCTGGC GGAAAACCTC | 3250 |
| AGTGTGACGC TCCCCGCCGC GTCCCACGCC ATCCCGCATC TGACCACCAG | 3300 |
| CGAAATGGAT TTTTGCATCG AGCTGGGTAA TAAGCGTTGG CAATTTAACC | 3350 |
| GCCAGTCAGG CTTTCTTTCA CAGATGTGGA TTGGCGATAA AAAACAACTG | 3400 |
| CTGACGCCGC TGCGCGATCA GTTCACCCGT GCACCGCTGG ATAACGACAT | 3450 |
| TGGCGTAAGT GAAGCGACCC GCATTGACCC TAACGCCTGG GTCGAACGCT | 3500 |
| GGAAGGCGGC GGGCCATTAC CAGGCCGAAG CAGCGTTGTT GCAGTGCACG | 3550 |
| GCAGATACAC TTGCTGATGC GGTGCTGATT ACGACCGCTC ACGCGTGGCA | 3600 |
| GCATCAGGGG AAAACCTTAT TTATCAGCCG GAAAACCTAC CGGATTGATG | 3650 |
| GTAGTGGTCA AATGGCGATT ACCGTTGATG TTGAAGTGGC GAGCGATACA | 3700 |
| CCGCATCCGG CGCGGATTGG CCTGAACTGC CAGCTGGCGC AGGTAGCAGA | 3750 |
| GCGGGTAAAC TGGCTCGGAT TAGGGCCGCA AGAAAACTAT CCCGACCGCC | 3800 |
| TTACTGCCGC CTGTTTTGAC CGCTGGGATC TGCCATTGTC AGACATGTAT | 3850 |
| ACCCCGTACG TCTTCCCGAG CGAAAACGGT CTGCGCTGCG GGACGCGCGA | 3900 |
| ATTGAATTAT GGCCCACACC AGTGGCGCGG CGACTTCCAG TTCAACATCA | 3950 |
| GCCGCTACAG TCAACAGCAA CTGATGGAAA CCAGCCATCG CCATCTGCTG | 4000 |
| CACGCGGAAG AAGGCACATG GCTGAATATC GACGGTTTCC ATATGGGGAT | 4050 |
| TGGTGGCGAC GACTCCTGGA GCCCGTCAGT ATCGGCGGAA TTACAGCTGA | 4100 |
| GCGCCGGTCG CTACCATTAC CAGTTGGTCT GGTGTCAAAA ATAATAATAA | 4150 |
| CCGGGCAGGC CATGTCTGCC CGTATTTCGC GTAAGGAAAT CCATTATGTA | 4200 |
| CTATTTAAAA AACACAAACT TTTGGATGTT CGGTTTATTC TTTTTCTTTT | 4250 |
| ACTTTTTTAT CATGGGAGCC TACTTCCCGT TTTTCCCGAT TTGGCTACAT | 4300 |
| GACATCAACC ATATCAGCAA AAGTGATACG GGTATTATTT TTGCCGCTAT | 4350 |
| TTCTCTGTTC TCGCTATTAT TCCAACCGCT GTTTGGTCTG CTTTCTGACA | 4400 |
| AACTCGGCCT CGACTCTAGG CGGCCGCGGG GATCCAGACA TGATAAGATA | 4450 |
| CATTGATGAG TTTGGACAAA CCACAACTAG AATGCAGTGA AAAAAATGCT | 4500 |
| TTATTTGTGA AATTTGTGAT GCTATTGCTT TATTTGTAAC CATTATAAGC | 4550 |
| TGCAATAAAC AAGTTAACAA CAACAATTGC ATTCATTTTA TGTTTCAGGT | 4600 |

```
TCAGGGGGAG GTGTGGGAGG TTTTTTCGGA TCCTCTAGAG TCGACCTGCA      4650

GGCTGATCAG TGGAAGGTGC TGAGGTACGA TGAGACCCGC ACCAGGTGCA      4700

GACCCTGCGA GTGTGGCGGT AAACATATTA GGAACCAGCC TGTGATGCTG      4750

GATGTGACCG AGGAGCTGAG GCCCGATCAC TTGGTGCTGG CCTGCACCCG      4800

CGCTGAGTTT GGCTCTAGCG ATGAAGATAC AGATTGAGGT ACTGAAATGT      4850

GTGGGCGTGG CTTAAGGGTG GGAAAGAATA TATAAGGTGG GGGTCTTATG      4900

TAGTTTTGTA TCTGTTTTGC AGCAGCCGCC GCCGCCATGA GCACCAACTC      4950

GTTTGATGGA AGCATTGTGA GCTCATATTT GACAACGCGC ATGCCCCCAT      5000

GGGCCGGGGT GCGTCAGAAT GTGATGGGCT CCAGCATTGA TGGTCGCCCC      5050

GTCCTGCCCG CAAACTCTAC TACCTTGACC TACGAGACCG TGTCTGGAAC      5100

GCCGTTGGAG ACTGCAGCCT CCGCCGCCGC TTCAGCCGCT GCAGCCACCG      5150

CCCGCGGGAT TGTGACTGAC TTTGCTTTCC TGAGCCCGCT TGCAAGCAGT      5200

GCAGCTTCCC GTTCATCCGC CGCGATGAC AAGTTGACGG CTCTTTTGGC       5250

ACAATTGGAT TCTTTGACCC GGGAACTTAA TGTCGTTTCT CAGCAGCTGT      5300

TGGATCTGCG CCAGCAGGTT TCTGCCCTGA AGGCTTCCTC CCCTCCCAAT      5350

GCGGTTTAAA ACATAAATAA AAAACCAGAC TCTGTTTGGA TTTGGATCAA      5400

GCAAGTGTCT TGCTGTCTTT ATTTAGGGGT TTTGCGCGCG CGGTAGGCCC      5450

GGGACCAGCG GTCTCGGTCG TTGAGGGTCC TGTGTATTTT TTCCAGGACG      5500

TGGTAAAGGT GACTCTGGAT GTTCAGATAC ATGGGCATAA GCCCGTCTCT      5550

GGGGTGGAGG TAGCACCACT GCAGAGCTTC ATGCTGCGGG GTGGTGTTGT      5600

AGATGATCCA GTCGTAGCAG GAGCGCTGGG CGTGGTGCCT AAAAATGTCT      5650

TTCAGTAGCA AGCTGATTGC CAGGGGCAGG CCCTTGGTGT AAGTGTTTAC      5700

AAAGCGGTTA AGCTGGGATG GGTGCATACG TGGGGATATG AGATGCATCT      5750

TGGACTGTAT TTTTAGGTTG GCTATGTTCC CAGCCATATC CCTCCGGGGA      5800

TTCATGTTGT GCAGAACCAC CAGCACAGTG TATCCGGTGC ACTTGGGAAA      5850

TTTGTCATGT AGCTTAGAAG GAAATGCGTG GAAGAACTTG GAGACGCCCT      5900

TGTGACCTCC AAGATTTTCC ATGCATTCGT CCATAATGAT GGCAATGGGC      5950

CCACGGGCGG CGGCCTGGGC GAAGATATTT CTGGGATCAC TAACGTCATA      6000

GTTGTGTTCC AGGATGAGAT CGTCATAGGC CATTTTTACA AAGCGCGGGC      6050

GGAGGGTGCC AGACTGCGGT ATAATGGTTC CATCCGGCCC AGGGGCGTAG      6100

TTACCCTCAC AGATTTGCAT TTCCCACGCT TTGAGTTCAG ATGGGGGGAT      6150

CATGTCTACC TGCGGGGCGA TGAAGAAAAC GGTTTCCGGG GTAGGGGAGA      6200

TCAGCTGGGA AGAAAGCAGG TTCCTGAGCA GCTGCGACTT ACCGCAGCCG      6250

GTGGGCCCGT AAATCACACC TATTACCGGG TGCAACTGGT AGTTAAGAGA      6300

GCTGCAGCTG CCGTCATCCC TGAGCAGGGG GGCCACTTCG TTAAGCATGT      6350

CCCTGACTCG CATGTTTTCC CTGACCAAAT CCGCCAGAAG GCGCTCGCCG      6400

CCCAGCGATA GCAGTTCTTG CAAGGAAGCA AAGTTTTTCA ACGGTTTGAG      6450

ACCGTCCGCC GTAGGCATGC TTTTGAGCGT TTGACCAAGC AGTTCCAGGC      6500

GGTCCCACAG CTCGGTCACC TGCTCTACGG CATCTCGATC CAGCATATCT      6550
```

| | |
|---|---|
| CCTCGTTTCG CGGGTTGGGG CGGCTTTCGC TGTACGGCAG TAGTCGGTGC | 6600 |
| TCGTCCAGAC GGGCCAGGGT CATGTCTTTC CACGGGCGCA GGGTCCTCGT | 6650 |
| CAGCGTAGTC TGGGTCACGG TGAAGGGGTG CGCTCCGGGC TGCGCGCTGG | 6700 |
| CCAGGGTGCG CTTGAGGCTG GTCCTGCTGG TGCTGAAGCG CTGCCGGTCT | 6750 |
| TCGCCCTGCG CGTCGGCCAG GTAGCATTTG ACCATGGTGT CATAGTCCAG | 6800 |
| CCCCTCCGCG GCGTGGCCCT TGGCGCGCAG CTTGCCCTTG GAGGAGGCGC | 6850 |
| CGCACGAGGG GCAGTGCAGA CTTTTGAGGG CGTAGAGCTT GGGCGCGAGA | 6900 |
| AATACCGATT CCGGGAGTA GGCATCCGCG CCGCAGGCCC CGCAGACGGT | 6950 |
| CTCGCATTCC ACGAGCCAGG TGAGCTCTGG CCGTTCGGGG TCAAAAACCA | 7000 |
| GGTTTCCCCC ATGCTTTTTG ATGCGTTTCT TACCTCTGGT TTCCATGAGC | 7050 |
| CGGTGTCCAC GCTCGGTGAC GAAAAGGCTG TCCGTGTCCC CGTATACAGA | 7100 |
| CTTGAGAGGC CTGTCCTCGA GCGGTGTTCC GCGGTCCTCC TCGTATAGAA | 7150 |
| ACTCGGACCA CTCTGAGACA AAGGCTCGCG TCCAGGCCAG CACGAAGGAG | 7200 |
| GCTAAGTGGG AGGGGTAGCG GTCGTTGTCC ACTAGGGGGT CCACTCGCTC | 7250 |
| CAGGGTGTGA AGACACATGT CGCCCTCTTC GGCATCAAGG AAGGTGATTG | 7300 |
| GTTTGTAGGT GTAGGCCACG TGACCGGGTG TTCCTGAAGG GGGGCTATAA | 7350 |
| AAGGGGGTGG GGGCGCGTTC GTCCTCACTC TCTTCCGCAT CGCTGTCTGC | 7400 |
| GAGGGCCAGC TGTTGGGGTG AGTACTCCCT CTGAAAAGCG GGCATGACTT | 7450 |
| CTGCGCTAAG ATTGTCAGTT TCCAAAAACG AGGAGGATTT GATATTCACC | 7500 |
| TGGCCCGCGG TGATGCCTTT GAGGGTGGCC GCATCCATCT GGTCAGAAAA | 7550 |
| GACAATCTTT TTGTTGTCAA GCTTGGTGGC AAACGACCCG TAGAGGGCGT | 7600 |
| TGGACAGCAA CTTGGCGATG GAGCGCAGGG TTTTGGTTTTT GTCGCGATCG | 7650 |
| GCGCGCTCCT TGGCCGCGAT GTTTAGCTGC ACGTATTCGC GCGCAACGCA | 7700 |
| CCGCCATTCG GGAAAGACGG TGGTGCGCTC GTCGGGCACC AGGTGCACGC | 7750 |
| GCCAACCGCG GTTGTGCAGG GTGACAAGGT CAACGCTGGT GGCTACCTCT | 7800 |
| CCGCGTAGGC GCTCGTTGGT CCAGCAGAGG CGGCCGCCCT TGCGCGAGCA | 7850 |
| GAATGGCGGT AGGGGGTCTA GCTGCGTCTC GTCCGGGGGG TCTGCGTCCA | 7900 |
| CGGTAAAGAC CCCGGGCAGC AGGCGCGCGT CGAAGTAGTC TATCTTGCAT | 7950 |
| CCTTGCAAGT CTAGCGCCTG CTGCCATGCG CGGGCGGCAA GCGCGCGCTC | 8000 |
| GTATGGGTTG AGTGGGGGAC CCCATGGCAT GGGGTGGGTG AGCGCGGAGG | 8050 |
| CGTACATGCC GCAAATGTCG TAAACGTAGA GGGGCTCTCT GAGTATTCCA | 8100 |
| AGATATGTAG GGTAGCATCT TCCACCGCGG ATGCTGGCGC GCACGTAATC | 8150 |
| GTATAGTTCG TGCGAGGGAG CGAGGAGGTC GGGACCGAGG TTGCTACGGG | 8200 |
| CGGGCTGCTC TGCTCGGAAG ACTATCTGCC TGAAGATGGC ATGTGAGTTG | 8250 |
| GATGATATGG TTGGACGCTG GAAGACGTTG AAGCTGGCGT CTGTGAGACC | 8300 |
| TACCGCGTCA CGCACGAAGG AGGCGTAGGA GTCGCGCAGC TTGTTGACCA | 8350 |
| GCTCGGCGGT GACCTGCACG TCTAGGGCGC AGTAGTCCAG GGTTTCCTTG | 8400 |
| ATGATGTCAT ACTTATCCTG TCCCTTTTTT TTCCACAGCT CGCGGTTGAG | 8450 |
| GACAAACTCT TCGCGGTCTT TCCAGTACTC TTGGATCGGA AACCCGTCGG | 8500 |
| CCTCCGAACG GTAAGAGCCT AGCATGTAGA ACTGGTTGAC GGCCTGGTAG | 8550 |

```
GCGCAGCATC CCTTTTCTAC GGGTAGCGCG TATGCCTGCG CGGCCTTCCG      8600
GAGCGAGGTG TGGGTGAGCG CAAAGGTGTC CCTGACCATG ACTTTGAGGT      8650
ACTGGTATTT GAAGTCAGTG TCGTCGCATC CGCCCTGCTC CCAGAGCAAA      8700
AAGTCCGTGC GCTTTTTGGA ACGCGGATTT GGCAGGGCGA AGGTGACATC      8750
GTTGAAGAGT ATCTTTCCCG CGCGAGGCAT AAAGTTGCGT GTGATGCGGA      8800
AGGGTCCCGG CACCTCGGAA CGGTTGTTAA TTACCTGGGC GGCGAGCACG      8850
ATCTCGTCAA AGCCGTTGAT GTTGTGGCCC ACAATGTAAA GTTCCAAGAA      8900
GCGCGGGATG CCCTTGATGG AAGGCAATTT TTTAAGTTCC TCGTAGGTGA      8950
GCTCTTCAGG GGAGCTGAGC CCGTGCTCTG AAAGGGCCCA GTCTGCAAGA      9000
TGAGGGTTGG AAGCGACGAA TGAGCTCCAC AGGTCACGGG CCATTAGCAT      9050
TTGCAGGTGG TCGCGAAAGG TCCTAAACTG GCGACCTATG GCCATTTTTT      9100
CTGGGGTGAT GCAGTAGAAG GTAAGCGGGT CTTGTTCCCA GCGGTCCCAT      9150
CCAAGGTTCG CGGCTAGGTC TCGCGCGGCA GTCACTAGAG GCTCATCTCC      9200
GCCGAACTTC ATGACCAGCA TGAAGGGCAC GAGCTGCTTC CCAAAGGCCC      9250
CCATCCAAGT ATAGGTCTCT ACATCGTAGG TGACAAAGAC ACGCTCGGTG      9300
CGAGGATGCG AGCCGATCGG GAAGAACTGG ATCTCCCGCC ACCAATTGGA      9350
GGAGTGGCTA TTGATGTGGT GAAAGTAGAA GTCCCTGCGA CGGGCCGAAC      9400
ACTCGTGCTG GCTTTTGTAA AAACGTGCGC AGTACTGGCA GCGGTGCACG      9450
GGCTGTACAT CCTGCACGAG GTTGACCTGA CGACCGCGCA CAAGGAAGCA      9500
GAGTGGGAAT TTGAGCCCCT CGCCTGGCGG GTTTGGCTGG TGGTCTTCTA      9550
CTTCGGCTGC TTGTCCTTGA CCGTCTGGCT GCTCGAGGGG AGTTACGGTG      9600
GATCGGACCA CCACGCCGCG CGAGCCCAAA GTCCAGATGT CCGCGCGCGG      9650
CGGTCGGAGC TTGATGACAA CATCGCGCAG ATGGGAGCTG TCCATGGTCT      9700
GGAGCTCCCG CGGCGTCAGG TCAGGCGGGA GCTCCTGCAG GTTTACCTCG      9750
CATAGACGGG TCAGGGCGCG GGCTAGATCC AGGTGATACC TAATTTCCAG      9800
GGGCTGGTTG GTGGCGGCGT CGATGGCTTG CAAGAGGCCG CATCCCCGCG      9850
GCGCGACTAC GGTACCGCGC GGCGGGCGGT GGGCCGCGGG GGTGTCCTTG      9900
GATGATGCAT CTAAAAGCGG TGACGCGGGC GAGCCCCCGG AGGTAGGGGG      9950
GGCTCCGGAC CCGCCGGGAG AGGGGGCAGG GGCACGTCGG CGCCGCGCGC     10000
GGGCAGGAGC TGGTGCTGCG CGCGTAGGTT GCTGGCGAAC GCGACGACGC     10050
GGCGGTTGAT CTCCTGAATC TGGCGCCTCT GCGTGAAGAC GACGGGCCCG     10100
GTGAGCTTGA GCCTGAAAGA GAGTTCGACA GAATCAATTT CGGTGTCGTT     10150
GACGGCGGCC TGGCGCAAAA TCTCCTGCAC GTCTCCTGAG TTGTCTTGAT     10200
AGGCGATCTC GGCCATGAAC TGCTCGATCT CTTCCTCCTG GAGATCTCCG     10250
CGTCCGGCTC GCTCCACGGT GGCGGCGAGG TCGTTGGAAA TGCGGGCCAT     10300
GAGCTGCGAG AAGGCGTTGA GGCCTCCCTC GTTCCAGACG CGGCTGTAGA     10350
CCACGCCCCC TTCGGCATCG CGGGCGCGCA TGACCACCTG CGCGAGATTG     10400
AGCTCCACGT GCCGGGCGAA GACGGCGTAG TTTCGCAGGC GCTGAAAGAG     10450
GTAGTTGAGG GTGGTGGCGG TGTGTTCTGC CACGAAGAAG TACATAACCC     10500
```

-continued

| | |
|---|---|
| AGCGTCGCAA CGTGGATTCG TTGATATCCC CCAAGGCCTC AAGGCGCTCC | 10550 |
| ATGGCCTCGT AGAAGTCCAC GGCGAAGTTG AAAAACTGGG AGTTGCGCGC | 10600 |
| CGACACGGTT AACTCCTCCT CCAGAAGACG GATGAGCTCG GCGACAGTGT | 10650 |
| CGCGCACCTC GCGCTCAAAG GCTACAGGGG CCTCTTCTTC TTCTTCAATC | 10700 |
| TCCTCTTCCA TAAGGGCCTC CCCTTCTTCT TCTTCTGGCG GCGGTGGGGG | 10750 |
| AGGGGGGACA CGGCGGCGAC GACGGCGCAC CGGGAGGCGG TCGACAAAGC | 10800 |
| GCTCGATCAT CTCCCCGCGG CGACGGCGCA TGGTCTCGGT GACGGCGCGG | 10850 |
| CCGTTCTCGC GGGGGCGCAG TTGGAAGACG CCGCCCGTCA TGTCCCGGTT | 10900 |
| ATGGGTTGGC GGGGGGCTGC CATGCGGCAG GGATACGGCG CTAACGATGC | 10950 |
| ATCTCAACAA TTGTTGTGTA GGTACTCCGC CGCCGAGGGA CCTGAGCGAG | 11000 |
| TCCGCATCGA CCGGATCGGA AAACCTCTCG AGAAAGGCGT CTAACCAGTC | 11050 |
| ACAGTCGCAA GGTAGGCTGA GCACCGTGGC GGGCGGCAGC GGGCGGCGGT | 11100 |
| CGGGGTTGTT TCTGGCGGAG GTGCTGCTGA TGATGTAATT AAAGTAGGCG | 11150 |
| GTCTTGAGAC GGCGGATGGT CGACAGAAGC ACCATGTCCT TGGGTCCGGC | 11200 |
| CTGCTGAATG CGCAGGCGGT CGGCCATGCC CCAGGCTTCG TTTTGACATC | 11250 |
| GGCGCAGGTC TTTGTAGTAG TCTTGCATGA GCCTTTCTAC CGGCACTTCT | 11300 |
| TCTTCTCCTT CCTCTTGTCC TGCATCTCTT GCATCTATCG CTGCGGCGGC | 11350 |
| GGCGGAGTTT GGCCGTAGGT GGCGCCCTCT TCCTCCCATG CGTGTGACCC | 11400 |
| CGAAGCCCCT CATCGGCTGA AGCAGGGCTA GGTCGGCGAC AACGCGCTCG | 11450 |
| GCTAATATGG CCTGCTGCAC CTGCGTGAGG GTAGACTGGA AGTCATCCAT | 11500 |
| GTCCACAAAG CGGTGGTATG CGCCCGTGTT GATGGTGTAA GTGCAGTTGG | 11550 |
| CCATAACGGA CCAGTTAACG GTCTGGTGAC CCGGCTGCGA GAGCTCGGTG | 11600 |
| TACCTGAGAC GCGAGTAAGC CCTCGAGTCA AATACGTAGT CGTTGCAAGT | 11650 |
| CCGCACCAGG TACTGGTATC CCACCAAAAA GTGCGGCGGC GGCTGGCGGT | 11700 |
| AGAGGGGCCA GCGTAGGGTG GCCGGGGCTC CGGGGCGAG ATCTTCCAAC | 11750 |
| ATAAGGCGAT GATATCCGTA GATGTACCTG GACATCCAGG TGATGCCGGC | 11800 |
| GGCGGTGGTG GAGGCGCGCG GAAAGTCGCG GACGCGGTTC CAGATGTTGC | 11850 |
| GCAGCGGCAA AAAGTGCTCC ATGGTCGGGA CGCTCTGGCC GGTCAGGCGC | 11900 |
| GCGCAATCGT TGACGCTCTA GACCGTGCAA AAGGAGAGCC TGTAAGCGGG | 11950 |
| CACTCTTCCG TGGTCTGGTG GATAAATTCG CAAGGGTATC ATGGCGGACG | 12000 |
| ACCGGGGTTC GAGCCCCGTA TCCGGCCGTC CGCCGTGATC CATGCGGTTA | 12050 |
| CCGCCCGCGT GTCGAACCCA GGTGTGCGAC GTCAGACAAC GGGGGAGTGC | 12100 |
| TCCTTTTGGC TTCCTTCCAG GCGCGGCGGC TGCTGCGCTA GCTTTTTTGG | 12150 |
| CCACTGGCCG CGCGCAGCGT AAGCGGTTAG GCTGGAAAGC GAAAGCATTA | 12200 |
| AGTGGCTCGC TCCCTGTAGC CGGAGGGTTA TTTTCCAAGG GTTGAGTCGC | 12250 |
| GGGACCCCCG GTTCGAGTCT CGGACCGGCC GGACTGCGGC GAACGGGGGT | 12300 |
| TTGCCTCCCC GTCATGCAAG ACCCCGCTTG CAAATTCCTC CGGAAACAGG | 12350 |
| GACGAGCCCC TTTTTTGCTT TTCCCAGATG CATCCGGTGC TGCGGCAGAT | 12400 |
| GCGCCCCCT CCTCAGCAGC GGCAAGAGCA AGAGCAGCGG CAGACATGCA | 12450 |
| GGGCACCCTC CCCTCCTCCT ACCGCGTCAG GAGGGGCGAC ATCCGCGGTT | 12500 |

```
GACGCGGCAG CAGATGGTGA TTACGAACCC CCGCGGCGCC GGGCCCGGCA        12550

CTACCTGGAC TTGGAGGAGG GCGAGGGCCT GGCGCGGCTA GGAGCGCCCT        12600

CTCCTGAGCG GTACCCAAGG GTGCAGCTGA AGCGTGATAC GCGTGAGGCG        12650

TACGTGCCGC GGCAGAACCT GTTTCGCGAC CGCGAGGGAG AGGAGCCCGA        12700

GGAGATGCGG GATCGAAAGT TCCACGCAGG GCGCGAGCTG CGGCATGGCC        12750

TGAATCGCGA GCGGTTGCTG CGCGAGGAGG ACTTTGAGCC CGACGCGCGA        12800

ACCGGGATTA GTCCCGCGCG CGCACACGTG GCGGCCGCCG ACCTGGTAAC        12850

CGCATACGAG CAGACGGTGA ACCAGGAGAT TAACTTTCAA AAAAGCTTTA        12900

ACAACCACGT GCGTACGCTT GTGGCGCGCG AGGAGGTGGC TATAGGACTG        12950

ATGCATCTGT GGGACTTTGT AAGCGCGCTG GAGCAAAACC CAAATAGCAA        13000

GCCGCTCATG GCGCAGCTGT TCCTTATAGT GCAGCACAGC AGGGACAACG        13050

AGGCATTCAG GGATGCGCTG CTAAACATAG TAGAGCCCGA GGGCCGCTGG        13100

CTGCTCGATT TGATAAACAT CCTGCAGAGC ATAGTGGTGC AGGAGCGCAG        13150

CTTGAGCCTG GCTGACAAGG TGGCCGCCAT CAACTATTCC ATGCTTAGCC        13200

TGGGCAAGTT TTACGCCCGC AAGATATACC ATACCCCTTA CGTTCCCATA        13250

GACAAGGAGG TAAAGATCGA GGGGTTCTAC ATGCGCATGG CGCTGAAGGT        13300

GCTTACCTTG AGCGACGACC TGGGCGTTTA TCGCAACGAG CGCATCCACA        13350

AGGCCGTGAG CGTGAGCCGG CGGCGCGAGC TCAGCGACCG CGAGCTGATG        13400

CACAGCCTGC AAAGGGCCCT GGCTGGCACG GGCAGCGGCG ATAGAGAGGC        13450

CGAGTCCTAC TTTGACGCGG GCGCTGACCT GCGCTGGGCC CCAAGCCGAC        13500

GCGCCCTGGA GGCAGCTGGG GCCGGACCTG GGCTGGCGGT GGCACCCGCG        13550

CGCGCTGGCA ACGTCGGCGG CGTGGAGGAA TATGACGAGG ACGATGAGTA        13600

CGAGCCAGAG GACGGCGAGT ACTAAGCGGT GATGTTTCTG ATCAGATGAT        13650

GCAAGACGCA ACGGACCCGG CGGTGCGGGC GGCGCTGCAG AGCCAGCCGT        13700

CCGGCCTTAA CTCCACGGAC GACTGGCGCC AGGTCATGGA CCGCATCATG        13750

TCGCTGACTG CGCGCAATCC TGACGCGTTC CGGCAGCAGC CGCAGGCCAA        13800

CCGGCTCTCC GCAATTCTGG AAGCGGTGGT CCCGGCGCGC GCAAACCCCA        13850

CGCACGAGAA GGTGCTGGCG ATCGTAAACG CGCTGGCCGA AAACAGGGCC        13900

ATCCGGCCCG ACGAGGCCGG CCTGGTCTAC GACGCGCTGC TTCAGCGCGT        13950

GGCTCGTTAC AACAGCGGCA ACGTGCAGAC CAACCTGGAC CGGCTGGTGG        14000

GGGATGTGCG CGAGGCCGTG GCGCAGCGTG AGCGCGCGCA GCAGCAGGGC        14050

AACCTGGGCT CCATGGTTGC ACTAAACGCC TTCCTGAGTA CACAGCCCGC        14100

CAACGTGCCG CGGGGACAGG AGGACTACAC CAACTTTGTG AGCGCACTGC        14150

GGCTAATGGT GACTGAGACA CCGCAAAGTG AGGTGTACCA GTCTGGGCCA        14200

GACTATTTTT TCCAGACCAG TAGACAAGGC CTGCAGACCG TAAACCTGAG        14250

CCAGGCTTTC AAAAACTTGC AGGGGCTGTG GGGGGTGCGG GCTCCCACAG        14300

GCGACCGCGC GACCGTGTCT AGCTTGCTGA CGCCCAACTC GCGCCTGTTG        14350

CTGCTGCTAA TAGCGCCCTT CACGGACAGT GGCAGCGTGT CCCGGGACAC        14400

ATACCTAGGT CACTTGCTGA CACTGTACCG CGAGGCCATA GGTCAGGCGC        14450
```

| | |
|---|---|
| ATGTGGACGA GCATACTTTC CAGGAGATTA CAAGTGTCAG CCGCGCGCTG | 14500 |
| GGGCAGGAGG ACACGGGCAG CCTGGAGGCA ACCCTAAACT ACCTGCTGAC | 14550 |
| CAACCGGCGG CAGAAGATCC CCTCGTTGCA CAGTTTAAAC AGCGAGGAGG | 14600 |
| AGCGCATTTT GCGCTACGTG CAGCAGAGCG TGAGCCTTAA CCTGATGCGC | 14650 |
| GACGGGGTAA CGCCCAGCGT GGCGCTGGAC ATGACCGCGC GCAACATGGA | 14700 |
| ACCGGGCATG TATGCCTCAA ACCGGCCGTT TATCAACCGC CTAATGGACT | 14750 |
| ACTTGCATCG CGCGGCCGCC GTGAACCCCG AGTATTTCAC CAATGCCATC | 14800 |
| TTGAACCCGC ACTGGCTACC GCCCCCTGGT TTCTACACCG GGGATTCGA | 14850 |
| GGTGCCCGAG GTAACGATG GATTCCTCTG GACGACATA GACGACAGCG | 14900 |
| TGTTTTCCCC GCAACCGCAG ACCCTGCTAG AGTTGCAACA GCGCGAGCAG | 14950 |
| GCAGAGGCGC CGCTGCGAAA GGAAAGCTTC CGCAGGCCAA GCAGCTTGTC | 15000 |
| CGATCTAGGC GCTGCGGCCC CGCGGTCAGA TGCTAGTAGC CCATTTCCAA | 15050 |
| GCTTGATAGG GTCTCTTACC AGCACTCGCA CCACCCGCCC GCGCCTGCTG | 15100 |
| GGCGAGGAGG AGTACCTAAA CAACTCGCTG CTGCAGCCGC AGCGCGAAAA | 15150 |
| AAACCTGCCT CCGGCATTTC CCAACAACGG GATAGAGAGC CTAGTGGACA | 15200 |
| AGATGAGTAG ATGGAAGACG TACGCGCAGG AGCACAGGGA CGTGCCAGGC | 15250 |
| CCGCGCCCGC CCACCCGTCG TCAAAGGCAC GACCGTCAGC GGGGTCTGGT | 15300 |
| GTGGGAGGAC GATGACTCGG CAGACGACAG CAGCGTCCTG GATTTGGGAG | 15350 |
| GGAGTGGCAA CCCGTTTGCG CACCTTCGCC CCAGGCTGGG GAGAATGTTT | 15400 |
| TAAAAAAAAA AAAGCATGAT GCAAAATAAA AAACTCACCA AGGCCATGGC | 15450 |
| ACCGAGCGTT GGTTTTCTTG TATTCCCCTT AGTATGCGGC GCGCGGCGAT | 15500 |
| GTATGAGGAA GGTCCTCCTC CCTCCTACGA GAGTGTGGTG AGCGCGGCGC | 15550 |
| CAGTGGCGGC GGCGCTGGGT TCTCCCTTCG ATGCTCCCCT GGACCCGCCG | 15600 |
| TTTGTGCCTC CGCGGTACCT GCGGCCTACC GGGGGGAGAA ACAGCATCCG | 15650 |
| TTACTCTGAG TTGGCACCCC TATTCGACAC CACCCGTGTG TACCTGGTGG | 15700 |
| ACAACAAGTC AACGGATGTG GCATCCCTGA ACTACCAGAA CGACCACAGC | 15750 |
| AACTTTCTGA CCACGGTCAT TCAAAACAAT GACTACAGCC CGGGGGAGGC | 15800 |
| AAGCACACAG ACCATCAATC TTGACGACCG GTCGCACTGG GGCGGCGACC | 15850 |
| TGAAAACCAT CCTGCATACC AACATGCCAA ATGTGAACGA GTTCATGTTT | 15900 |
| ACCAATAAGT TTAAGGCGCG GGTGATGGTG TCGCGCTTGC CTACTAAGGA | 15950 |
| CAATCAGGTG GAGCTGAAAT ACGAGTGGGT GGAGTTCACG CTGCCCGAGG | 16000 |
| GCAACTACTC CGAGACCATG ACCATAGACC TTATGAACAA CGCGATCGTG | 16050 |
| GAGCACTACT TGAAAGTGGG CAGACAGAAC GGGGTTCTGG AAAGCGACAT | 16100 |
| CGGGGTAAAG TTTGACACCC GCAACTTCAG ACTGGGGTTT GACCCCGTCA | 16150 |
| CTGGTCTTGT CATGCCTGGG GTATATACAA CGAAGCCTT CCATCCAGAC | 16200 |
| ATCATTTTGC TGCCAGGATG CGGGGTGGAC TTCACCCACA GCCGCCTGAG | 16250 |
| CAACTTGTTG GGCATCCGCA AGCGGCAACC CTTCCAGGAG GGCTTTAGGA | 16300 |
| TCACCTACGA TGATCTGGAG GGTGGTAACA TTCCCGCACT GTTGGATGTG | 16350 |
| GACGCCTACC AGGCGAGCTT GAAAGATGAC ACCGAACAGG GCGGGGGTGG | 16400 |
| CGCAGGCGGC AGCAACAGCA GTGGCAGCGG CGCGGAAGAG AACTCCAACG | 16450 |

-continued

| | |
|---|---|
| CGGCAGCCGC GGCAATGCAG CCGGTGGAGG ACATGAACGA TCATGCCATT | 16500 |
| CGCGGCGACA CCTTTGCCAC ACGGGCTGAG GAGAAGCGCG CTGAGGCCGA | 16550 |
| AGCAGCGGCC GAAGCTGCCG CCCCCGCTGC GCAACCCGAG GTCGAGAAGC | 16600 |
| CTCAGAAGAA ACCGGTGATC AAACCCCTGA CAGAGGACAC CAAGAAACGC | 16650 |
| AGTTACAACC TAATAAGCAA TGACAGCACC TTCACCCAGT ACCGCAGCTG | 16700 |
| GTACCTTGCA TACAACTACG GCGACCCTCA GACCGGAATC CGCTCATGGA | 16750 |
| CCCTGCTTTG CACTCCTGAC GTAACCTGCG GCTCGGAGCA GGTCTACTGG | 16800 |
| TCGTTGCCAG ACATGATGCA AGACCCCGTG ACCTTCCGCT CCACGCGCCA | 16850 |
| GATCAGCAAC TTTCCGGTGG TGGGCGCCGA GCTGTTGCCC GTGCACTCCA | 16900 |
| AGAGCTTCTA CAACGACCAG GCCGTCTACT CCCAACTCAT CCGCCAGTTT | 16950 |
| ACCTCTCTGA CCCACGTGTT CAATCGCTTT CCCGAGAACC AGATTTTGGC | 17000 |
| GCGCCCGCCA GCCCCCACCA TCACCACCGT CAGTGAAAAC GTTCCTGCTC | 17050 |
| TCACAGATCA CGGGACGCTA CCGCTGCGCA ACAGCATCGG AGGAGTCCAG | 17100 |
| CGAGTGACCA TTACTGACGC CAGACGCCGC ACCTGCCCCT ACGTTTACAA | 17150 |
| GGCCCTGGGC ATAGTCTCGC CGCGCGTCCT ATCGAGCCGC ACTTTTTGAG | 17200 |
| CAAGCATGTC CATCCTTATA TCGCCCAGCA ATAACACAGG CTGGGGCCTG | 17250 |
| CGCTTCCCAA GCAAGATGTT TGGCGGGGCC AAGAAGCGCT CCGACCAACA | 17300 |
| CCCAGTGCGC GTGCGCGGGC ACTACCGCGC GCCCTGGGGC GCGCACAAAC | 17350 |
| GCGGCCGCAC TGGGCGCACC ACCGTCGATG ACGCCATCGA CGCGGTGGTG | 17400 |
| GAGGAGGCGC GCAACTACAC GCCCACGCCG CCACCAGTGT CCACAGTGGA | 17450 |
| CGCGGCCATT CAGACCGTGG TGCGCGGAGC CCGGCGCTAT GCTAAAATGA | 17500 |
| AGAGACGGCG GAGGCGCGTA GCACGTCGCC ACCGCCGCCG ACCCGGCACT | 17550 |
| GCCGCCCAAC GCGCGGCGGC GGCCCTGCTT AACCGCGCAC GTCGCACCGG | 17600 |
| CCGACGGGCG GCCATGCGGG CCGCTCGAAG GCTGGCCGCG GGTATTGTCA | 17650 |
| CTGTGCCCCC CAGGTCCAGG CGACGAGCGG CCGCCGCAGC AGCCGCGGCC | 17700 |
| ATTAGTGCTA TGACTCAGGG TCGCAGGGGC AACGTGTATT GGGTGCGCGA | 17750 |
| CTCGGTTAGC GGCCTGCGCG TGCCCGTGCG CACCCGCCCC CCGCGCAACT | 17800 |
| AGATTGCAAG AAAAAACTAC TTAGACTCGT ACTGTTGTAT GTATCCAGCG | 17850 |
| GCGGCGGCGC GCAACGAAGC TATGTCCAAG CGCAAAATCA AGAAGAGAT | 17900 |
| GCTCCAGGTC ATCGCGCCGG AGATCTATGG CCCCCCGAAG AAGGAAGAGC | 17950 |
| AGGATTACAA GCCCCGAAAG CTAAAGCGGG TCAAAAAGAA AAAGAAAGAT | 18000 |
| GATGATGATG AACTTGACGA CGAGGTGGAA CTGCTGCACG CTACCGCGCC | 18050 |
| CAGGCGACGG GTACAGTGGA AAGGTCGACG CGTAAAACGT GTTTTGCGAC | 18100 |
| CCGGCACCAC CGTAGTCTTT ACGCCCGGTG AGCGCTCCAC CCGCACCTAC | 18150 |
| AAGCGCGTGT ATGATGAGGT GTACGGCGAC GAGGACCTGC TTGAGCAGGC | 18200 |
| CAACGAGCGC CTCGGGGAGT TTGCCTACGG AAAGCGGCAT AAGGACATGC | 18250 |
| TGGCGTTGCC GCTGGACGAG GGCAACCCAA CACCTAGCCT AAAGCCCGTA | 18300 |
| ACACTGCAGC AGGTGCTGCC CGCGCTTGCA CCGTCCGAAG AAAAGCGCGG | 18350 |
| CCTAAAGCGC GAGTCTGGTG ACTTGGCACC CACCGTGCAG CTGATGGTAC | 18400 |

-continued

| | |
|---|---|
| CCAAGCGCCA GCGACTGGAA GATGTCTTGG AAAAAATGAC CGTGGAACCT | 18450 |
| GGGCTGGAGC CCGAGGTCCG CGTGCGGCCA ATCAAGCAGG TGGCGCCGGG | 18500 |
| ACTGGGCGTG CAGACCGTGG ACGTTCAGAT ACCCACTACC AGTAGCACCA | 18550 |
| GTATTGCCAC CGCCACAGAG GGCATGGAGA CACAAACGTC CCCGGTTGCC | 18600 |
| TCAGCGGTGG CGGATGCCGC GGTGCAGGCG GTCGCTGCGG CCGCGTCCAA | 18650 |
| GACCTCTACG GAGGTGCAAA CGGACCCGTG GATGTTTCGC GTTTCAGCCC | 18700 |
| CCCGGCGCCC GCGCGGTTCG AGGAAGTACG GCGCCGCCAG CGCGCTACTG | 18750 |
| CCCGAATATG CCCTACATCC TTCCATTGCG CCTACCCCCG GCTATCGTGG | 18800 |
| CTACACCTAC CGCCCCAGAA GACGAGCAAC TACCCGACGC CGAACCACCA | 18850 |
| CTGGAACCCG CCGCCGCCGT CGCCGTCGCC AGCCCGTGCT GGCCCCGATT | 18900 |
| TCCGTGCGCA GGGTGGCTCG CGAAGGAGGC AGGACCCTGG TGCTGCCAAC | 18950 |
| AGCGCGCTAC CACCCCAGCA TCGTTTAAAA GCCGGTCTTT GTGGTTCTTG | 19000 |
| CAGATATGGC CCTCACCTGC CGCCTCCGTT TCCCGGTGCC GGGATTCCGA | 19050 |
| GGAAGAATGC ACCGTAGGAG GGGCATGGCC GGCCACGGCC TGACGGGCGG | 19100 |
| CATGCGTCGT GCGCACCACC GGCGGCGGCG CGCGTCGCAC CGTCGCATGC | 19150 |
| GCGGCGGTAT CCTGCCCCTC CTTATTCCAC TGATCGCCGC GGCGATTGGC | 19200 |
| GCCGTGCCCG GAATTGCATC CGTGGCCTTG CAGGCGCAGA GACACTGATT | 19250 |
| AAAAACAAGT TGCATGTGGA AAAATCAAAA TAAAAAGTCT GGACTCTCAC | 19300 |
| GCTCGCTTGG TCCTGTAACT ATTTTGTAGA ATGGAAGACA TCAACTTTGC | 19350 |
| GTCTCTGGCC CCGCGACACG GCTCGCGCCC GTTCATGGGA AACTGGCAAG | 19400 |
| ATATCGGCAC CAGCAATATG AGCGGTGGCG CCTTCAGCTG GGGCTCGCTG | 19450 |
| TGGAGCGGCA TTAAAAATTT CGGTTCCACC GTTAAGAACT ATGGCAGCAA | 19500 |
| GGCCTGGAAC AGCAGCACAG GCCAGATGCT GAGGGATAAG TTGAAAGAGC | 19550 |
| AAAATTTCCA ACAAAAGGTG GTAGATGGCC TGGCCTCTGG CATTAGCGGG | 19600 |
| GTGGTGGACC TGGCCAACCA GGCAGTGCAA AATAAGATTA ACAGTAAGCT | 19650 |
| TGATCCCCGC CCTCCCGTAG AGGAGCCTCC ACCGGCCGTG GAGACAGTGT | 19700 |
| CTCCAGAGGG GCGTGGCGAA AAGCGTCCGC GCCCCGACAG GGAAGAAACT | 19750 |
| CTGGTGACGC AAATAGACGA GCCTCCCTCG TACGAGGAGG CACTAAAGCA | 19800 |
| AGGCCTGCCC ACCACCCGTC CCATCGCGCC CATGGCTACC GGAGTGCTGG | 19850 |
| GCCAGCACAC ACCCGTAACG CTGGACCTGC CTCCCCCCGC CGACACCCAG | 19900 |
| CAGAAACCTG TGCTGCCAGG CCCGACCGCC GTTGTTGTAA CCCGTCCTAG | 19950 |
| CCGCGCGTCC CTGCGCCGCG CCGCCAGCGG TCCGCGATCG TTGCGGCCCG | 20000 |
| TAGCCAGTGG CAACTGGCAA AGCACACTGA ACAGCATCGT GGGTCTGGGG | 20050 |
| GTGCAATCCC TGAAGCGCCG ACGATGCTTC TGAATAGCTA ACGTGTCGTA | 20100 |
| TGTGTGTCAT GTATGCGTCC ATGTCGCCGC CAGAGGAGCT GCTGAGCCGC | 20150 |
| CGCGCGCCCC CTTTCCAAGA TGGCTACCCC TTCGATGATG CCGCAGTGGT | 20200 |
| CTTACATGCA CATCTCGGGC CAGGACGCCT CGGAGTACCT GAGCCCCGGG | 20250 |
| CTGGTGCAGT TTGCCCGCGC CACCGAGACG TACTTCAGCC TGAATAACAA | 20300 |
| GTTTAGAAAC CCCACGGTGG CGCCTACGCA CGACGTGACC ACAGACCGGT | 20350 |
| CCCAGCGTTT GACGCTGCGG TTCATCCCTG TGGACCGTGA GGATACTGCG | 20400 |

| | |
|---|---|
| TACTCGTACA AGGCGCGGTT CACCCTAGCT GTGGGTGATA ACCGTGTGCT | 20450 |
| GGACATGGCT TCCACGTACT TTGACATCCG CGGCGTGCTG GACAGGGGCC | 20500 |
| CTACTTTTAA GCCCTACTCT GGCACTGCCT ACAACGCCCT GGCTCCCAAG | 20550 |
| GGTGCCCCAA ATCCTTGCGA ATGGGATGAA GCTGCTACTG CTCTTGAAAT | 20600 |
| AAACCTAGAA GAAGAGGACG ATGACAACGA AGACGAAGTA GACGAGCAAG | 20650 |
| CTGAGCAGCA AAAAACTCAC GTATTTGGGC AGGCGCCTTA TTCTGGTATA | 20700 |
| AATATTACAA AGGAGGGTAT TCAAATAGGT GTCGAAGGTC AAACACCTAA | 20750 |
| ATATGCCGAT AAAACATTTC AACCTGAACC TCAAATAGGA GAATCTCAGT | 20800 |
| GGTACGAAAC TGAAATTAAT CATGCAGCTG GGAGAGTCCT TAAAAAGACT | 20850 |
| ACCCCAATGA AACCATGTTA CGGTTCATAT GCAAAACCCA CAAATGAAAA | 20900 |
| TGGAGGGCAA GGCATTCTTG TAAAGCAACA AAATGGAAAG CTAGAAAGTC | 20950 |
| AAGTGGAAAT GCAATTTTTC TCAACTACTG AGGCGACCGC AGGCAATGGT | 21000 |
| GATAACTTGA CTCCTAAAGT GGTATTGTAC AGTGAAGATG TAGATATAGA | 21050 |
| AACCCCAGAC ACTCATATTT CTTACATGCC CACTATTAAG GAAGGTAACT | 21100 |
| CACGAGAACT AATGGGCCAA CAATCTATGC CCAACAGGCC TAATTACATT | 21150 |
| GCTTTTAGGG ACAATTTTAT TGGTCTAATG TATTACAACA GCACGGGTAA | 21200 |
| TATGGGTGTT CTGGCGGGCC AAGCATCGCA GTTGAATGCT GTTGTAGATT | 21250 |
| TGCAAGACAG AAACACAGAG CTTTCATACC AGCTTTTGCT TGATTCCATT | 21300 |
| GGTGATAGAA CCAGGTACTT TTCTATGTGG AATCAGGCTG TTGACAGCTA | 21350 |
| TGATCCAGAT GTTAGAATTA TTGAAAATCA TGGAACTGAA GATGAACTTC | 21400 |
| CAAATTACTG CTTTCCACTG GGAGGTGTGA TTAATACAGA GACTCTTACC | 21450 |
| AAGGTAAAAC CTAAAACAGG TCAGGAAAAT GGATGGGAAA AAGATGCTAC | 21500 |
| AGAATTTTCA GATAAAAATG AAATAAGAGT TGGAAATAAT TTTGCCATGG | 21550 |
| AAATCAATCT AAATGCCAAC CTGTGGAGAA ATTTCCTGTA CTCCAACATA | 21600 |
| GCGCTGTATT TGCCCGACAA GCTAAAGTAC AGTCCTTCCA ACGTAAAAAT | 21650 |
| TTCTGATAAC CCAAACACCT ACGACTACAT GAACAAGCGA GTGGTGGCTC | 21700 |
| CCGGGTTAGT GGACTGCTAC ATTAACCTTG GAGCACGCTG GTCCCTTGAC | 21750 |
| TATATGGACA ACGTCAACCC ATTTAACCAC CACCGCAATG CTGGCCTGCG | 21800 |
| CTACCGCTCA ATGTTGCTGG GCAATGGTCG CTATGTGCCC TTCCACATCC | 21850 |
| AGGTGCCTCA GAAGTTCTTT GCCATTAAAA ACCTCCTTCT CCTGCCGGGC | 21900 |
| TCATACACCT ACGAGTGGAA CTTCAGGAAG GATGTTAACA TGGTTCTGCA | 21950 |
| GAGCTCCCTA GGAAATGACC TAAGGGTTGA CGGAGCCAGC ATTAAGTTTG | 22000 |
| ATAGCATTTG CCTTTACGCC ACCTTCTTCC CCATGGCCCA CAACACCGCC | 22050 |
| TCCACGCTTG AGGCCATGCT TAGAAACGAC ACCAACGACC AGTCCTTTAA | 22100 |
| CGACTATCTC TCCGCCGCCA ACATGCTCTA CCCTATACCC GCCAACGCTA | 22150 |
| CCAACGTGCC CATATCCATC CCCTCCCGCA ACTGGGCGG TTTCCGCGGC | 22200 |
| TGGGCCTTCA CGCGCCTTAA GACTAAGGAA ACCCCATCAC TGGGCTCGGG | 22250 |
| CTACGACCCT TATTACACCT ACTCTGGCTC TATACCCTAC CTAGATGGAA | 22300 |
| CCTTTTACCT CAACCACACC TTTAAGAAGG TGGCCATTAC CTTTGACTCT | 22350 |

-continued

| | |
|---|---|
| TCTGTCAGCT GGCCTGGCAA TGACCGCCTG CTTACCCCCA ACGAGTTTGA | 22400 |
| AATTAAGCGC TCAGTTGACG GGGAGGGTTA CAACGTTGCC CAGTGTAACA | 22450 |
| TGACCAAAGA CTGGTTCCTG GTACAAATGC TAGCTAACTA CAACATTGGC | 22500 |
| TACCAGGGCT TCTATATCCC AGAGAGCTAC AAGGACCGCA TGTACTCCTT | 22550 |
| CTTTAGAAAC TTCCAGCCCA TGAGCCGTCA GGTGGTGGAT GATACTAAAT | 22600 |
| ACAAGGACTA CCAACAGGTG GGCATCCTAC ACCAACACAA CAACTCTGGA | 22650 |
| TTTGTTGGCT ACCTTGCCCC CACCATGCGC GAAGGACAGG CCTACCCTGC | 22700 |
| TAACTTCCCC TATCCGCTTA TAGGCAAGAC CGCAGTTGAC AGCATTACCC | 22750 |
| AGAAAAAGTT TCTTTGCGAT CGCACCCTTT GGCGCATCCC ATTCTCCAGT | 22800 |
| AACTTTATGT CCATGGGCGC ACTCACAGAC CTGGGCCAAA ACCTTCTCTA | 22850 |
| CGCCAACTCC GCCCACGCGC TAGACATGAC TTTTGAGGTG GATCCCATGG | 22900 |
| ACGAGCCCAC CCTTCTTTAT GTTTTGTTTG AAGTCTTTGA CGTGGTCCGT | 22950 |
| GTGCACCGGC CGCACCGCGG CGTCATCGAA ACCGTGTACC TGCGCACGCC | 23000 |
| CTTCTCGGCC GGCAACGCCA CAACATAAAG AAGCAAGCAA CATCAACAAC | 23050 |
| AGCTGCCGCC ATGGGCTCCA GTGAGCAGGA ACTGAAAGCC ATTGTCAAAG | 23100 |
| ATCTTGGTTG TGGGCCATAT TTTTTGGGCA CCTATGACAA GCGCTTTCCA | 23150 |
| GGCTTTGTTT CTCCACACAA GCTCGCCTGC GCCATAGTCA ATACGGCCGG | 23200 |
| TCGCGAGACT GGGGGCGTAC ACTGGATGGC CTTTGCCTGG AACCCGCACT | 23250 |
| CAAAAACATG CTACCTCTTT GAGCCCTTTG GCTTTTCTGA CCAGCGACTC | 23300 |
| AAGCAGGTTT ACCAGTTTGA GTACGAGTCA CTCCTGCGCC GTAGCGCCAT | 23350 |
| TGCTTCTTCC CCCGACCGCT GTATAACGCT GGAAAAGTCC ACCCAAAGCG | 23400 |
| TACAGGGCC CAACTCGGCC GCCTGTGGAC TATTCTGCTG CATGTTTCTC | 23450 |
| CACGCCTTTG CCAACTGGCC CCAAACTCCC ATGGATCACA ACCCCACCAT | 23500 |
| GAACCTTATT ACCGGGGTAC CCAACTCCAT GCTCAACAGT CCCCAGGTAC | 23550 |
| AGCCCACCCT GCGTCGCAAC CAGGAACAGC TCTACAGCTT CCTGGAGCGC | 23600 |
| CACTCGCCCT ACTTCCGCAG CCACAGTGCG CAGATTAGGA GCGCCACTTC | 23650 |
| TTTTTGTCAC TTGAAAAACA TGTAAAAATA ATGTACTAGA GACACTTTCA | 23700 |
| ATAAAGGCAA ATGCTTTTAT TTGTACACTC TCGGGTGATT ATTTACCCCC | 23750 |
| ACCCTTGCCG TCTGCGCCGT TTAAAAATCA AAGGGGTTCT GCCGCGCATC | 23800 |
| GCTATGCGCC ACTGGCAGGG ACACGTTGCG ATACTGGTGT TTAGTGCTCC | 23850 |
| ACTTAAACTC AGGCACAACC ATCCGCGGCA GCTCGGTGAA GTTTTCACTC | 23900 |
| CACAGGCTGC GCACCATCAC CAACGCGTTT AGCAGGTCGG GCGCCGATAT | 23950 |
| CTTGAAGTCG CAGTTGGGGC CTCCGCCCTG CGCGCGCGAG TTGCGATACA | 24000 |
| CAGGGTTGCA GCACTGGAAC ACTATCAGCG CCGGGTGGTG CACGCTGGCC | 24050 |
| AGCACGCTCT TGTCGGAGAT CAGATCCGCG TCCAGGTCCT CCGCGTTGCT | 24100 |
| CAGGGCGAAC GGAGTCAACT TTGGTAGCTG CCTTCCCAAA AAGGGCGCGT | 24150 |
| GCCCAGGCTT TGAGTTGCAC TCGCACCGTA GTGGCATCAA AAGGTGACCG | 24200 |
| TGCCCGGTCT GGGCGTTAGG ATACAGCGCC TGCATAAAAG CCTTGATCTG | 24250 |
| CTTAAAAGCC ACCTGAGCCT TTGCGCCTTC AGAGAAGAAC ATGCCGCAAG | 24300 |
| ACTTGCCGGA AAACTGATTG GCCGGACAGG CCGCGTCGTG CACGCAGCAC | 24350 |

```
CTTGCGTCGG TGTTGGAGAT CTGCACCACA TTTCGCCCCC ACCGGTTCTT      24400

CACGATCTTG GCCTTGCTAG ACTGCTCCTT CAGCGCGCGC TGCCCGTTTT      24450

CGCTCGTCAC ATCCATTTCA ATCACGTGCT CCTTATTTAT CATAATGCTT      24500

CCGTGTAGAC ACTTAAGCTC GCCTTCGATC TCAGCGCAGC GGTGCAGCCA      24550

CAACGCGCAG CCCGTGGGCT CGTGATGCTT GTAGGTCACC TCTGCAAACG      24600

ACTGCAGGTA CGCCTGCAGG AATCGCCCCA TCATCGTCAC AAAGGTCTTG      24650

TTGCTGGTGA AGGTCAGCTG CAACCCGCGG TGCTCCTCGT TCAGCCAGGT      24700

CTTGCATACG GCCGCCAGAG CTTCCACTTG GTCAGGCAGT AGTTTGAAGT      24750

TCGCCTTTAG ATCGTTATCC ACGTGGTACT TGTCCATCAG CGCGCGCGCA      24800

GCCTCCATGC CCTTCTCCCA CGCAGACACG ATCGGCACAC TCAGCGGGTT      24850

CATCACCGTA ATTTCACTTT CCGCTTCGCT GGGCTCTTCC TCTTCCTCTT      24900

GCGTCCGCAT ACCACGCGCC ACTGGGTCGT CTTCATTCAG CCGCCGCACT      24950

GTGCGCTTAC CTCCTTTGCC ATGCTTGATT AGCACCGGTG GGTTGCTGAA      25000

ACCCACCATT TGTAGCGCCA CATCTTCTCT TTCTTCCTCG CTGTCCACGA      25050

TTACCTCTGG TGATGGCGGG CGCTCGGGCT TGGGAGAAGG GCGCTTCTTT      25100

TTCTTCTTGG GCGCAATGGC CAAATCCGCC GCCGAGGTCG ATGGCCGCGG      25150

GCTGGGTGTG CGCGGCACCA GCGCGTCTTG TGATGAGTCT TCCTCGTCCT      25200

CGGACTCGAT ACGCCGCCTC ATCCGCTTTT TTGGGGGCGC CCGGGGAGGC      25250

GGCGGCGACG GGGACGGGGA CGACACGTCC TCCATGGTTG GGGGACGTCG      25300

CGCCGCACCG CGTCCGCGCT CGGGGGTGGT TTCGCGCTGC TCCTCTTCCC      25350

GACTGGCCAT TTCCTTCTCC TATAGGCAGA AAAAGATCAT GGAGTCAGTC      25400

GAGAAGAAGG ACAGCCTAAC CGCCCCTCT GAGTTCGCCA CCACCGCCTC       25450

CACCGATGCC GCCAACGCGC CTACCACCTT CCCCGTCGAG GCACCCCGC       25500

TTGAGGAGGA GGAAGTGATT ATCGAGCAGG ACCCAGGTTT TGTAAGCGAA      25550

GACGACGAGG ACCGCTCAGT ACCAACAGAG GATAAAAAGC AAGACCAGGA      25600

CAACGCAGAG GCAAACGAGG AACAAGTCGG GCGGGGGGAC GAAAGGCATG      25650

GCGACTACCT AGATGTGGGA GACGACGTGC TGTTGAAGCA TCTGCAGCGC      25700

CAGTGCGCCA TTATCTGCGA CGCGTTGCAA GAGCGCAGCG ATGTGCCCCT      25750

CGCCATAGCG GATGTCAGCC TTGCCTACGA ACGCCACCTA TTCTCACCGC      25800

GCGTACCCCC CAAACGCCAA GAAAACGGCA CATGCGAGCC CAACCCGCGC      25850

CTCAACTTCT ACCCCGTATT TGCCGTGCCA GAGGTGCTTG CCACCTATCA      25900

CATCTTTTTC CAAAACTGCA AGATACCCCT ATCCTGCCGT GCCAACCGCA      25950

GCCGAGCGGA CAAGCAGCTG GCCTTGCGGC AGGGCGCTGT CATACCTGAT      26000

ATCGCCTCGC TCAACGAAGT GCCAAAAATC TTTGAGGGTC TTGGACGCGA      26050

CGAGAAGCGC GCGGCAAACG CTCTGCAACA GGAAAACAGC GAAAATGAAA      26100

GTCACTCTGG AGTGTTGGTG GAACTCGAGG GTGACAACGC GCGCCTAGCC      26150

GTACTAAAAC GCAGCATCGA GGTCACCCAC TTTGCCTACC CGGCACTTAA      26200

CCTACCCCCC AAGGTCATGA GCACAGTCAT GAGTGAGCTG ATCGTGCGCC      26250

GTGCGCAGCC CCTGGAGAGG GATGCAAATT TGCAAGAACA AACAGAGGAG      26300
```

```
                                                        -continued
GGCCTACCCG CAGTTGGCGA CGAGCAGCTA GCGCGCTGGC TTCAAACGCG           26350

CGAGCCTGCC GACTTGGAGG AGCGACGCAA ACTAATGATG GCCGCAGTGC           26400

TCGTTACCGT GGAGCTTGAG TGCATGCAGC GGTTCTTTGC TGACCCGGAG           26450

ATGCAGCGCA AGCTAGAGGA AACATTGCAC TACACCTTTC GACAGGGCTA           26500

CGTACGCCAG GCCTGCAAGA TCTCCAACGT GGAGCTCTGC AACCTGGTCT           26550

CCTACCTTGG AATTTTGCAC GAAAACCGCC TTGGGCAAAA CGTGCTTCAT           26600

TCCACGCTCA AGGGCGAGGC GCGCCGCGAC TACGTCCGCG ACTGCGTTTA           26650

CTTATTTCTA TGCTACACCT GGCAGACGGC CATGGGCGTT TGGCAGCAGT           26700

GCTTGGAGGA GTGCAACCTC AAGGAGCTGC AGAAACTGCT AAAGCAAAAC           26750

TTGAAGGACC TATGGACGGC CTTCAACGAG CGCTCCGTGG CCGCGCACCT           26800

GGCGGACATC ATTTTCCCCG AACGCCTGCT TAAAACCCTG CAACAGGGTC           26850

TGCCAGACTT CACCAGTCAA AGCATGTTGC AGAACTTTAG GAACTTTATC           26900

CTAGAGCGCT CAGGAATCTT GCCCGCCACC TGCTGTGCAC TTCCTAGCGA           26950

CTTTGTGCCC ATTAAGTACC GCGAATGCCC TCCGCCGCTT TGGGGCCACT           27000

GCTACCTTCT GCAGCTAGCC AACTACCTTG CCTACCACTC TGACATAATG           27050

GAAGACGTGA GCGGTGACGG TCTACTGGAG TGTCACTGTC GCTGCAACCT           27100

ATGCACCCCG CACCGCTCCC TGGTTTGCAA TTCGCAGCTG CTTAACGAAA           27150

GTCAAATTAT CGGTACCTTT GAGCTGCAGG GTCCCTCGCC TGACGAAAAG           27200

TCCGCGGCTC CGGGGTTGAA ACTCACTCCG GGGCTGTGGA CGTCGGCTTA           27250

CCTTCGCAAA TTTGTACCTG AGGACTACCA CGCCCACGAG ATTAGGTTCT           27300

ACGAAGACCA ATCCCGCCCG CCAAATGCGG AGCTTACCGC CTGCGTCATT           27350

ACCCAGGGCC ACATTCTTGG CCAATTGCAA GCCATCAACA AAGCCCGCCA           27400

AGAGTTTCTG CTACGAAAGG GACGGGGGGT TTACTTGGAC CCCCAGTCCG           27450

GCGAGGAGCT CAACCCAATC CCCCCGCCGC CGCAGCCCTA TCAGCAGCAG           27500

CCGCGGGCCC TTGCTTCCCA GGATGGCACC CAAAAAGAAG CTGCAGCTGC           27550

CGCCGCCACC CACGGACGAG GAGGAATACT GGGACAGTCA GGCAGAGGAG           27600

GTTTTGGACG AGGAGGAGGA GGACATGATG GAAGACTGGG AGAGCCTAGA           27650

CGAGGAAGCT TCCGAGGTCG AAGAGGTGTC AGACGAAACA CCGTCACCCT           27700

CGGTCGCATT CCCCTCGCCG GCGCCCCAGA AATCGGCAAC CGGTTCCAGC           27750

ATGGCTACAA CCTCCGCTCC TCAGGCGCCG CCGGCACTGC CCGTTCGCCG           27800

ACCCAACCGT AGATGGGACA CCACTGGAAC CAGGGCCGGT AAGTCCAAGC           27850

AGCCGCCGCC GTTAGCCCAA GAGCAACAAC AGCGCCAAGG CTACCGCTCA           27900

TGGCGCGGGC ACAAGAACGC CATAGTTGCT TGCTTGCAAG ACTGTGGGGG           27950

CAACATCTCC TTCGCCCGCC GCTTTCTTCT CTACCATCAC GGCGTGGCCT           28000

TCCCCCGTAA CATCCTGCAT TACTACCGTC ATCTCTACAG CCCATACTGC           28050

ACCGGCGGCA GCGGCAGCGG CAGCAACAGC AGCGGCCACA CAGAAGCAAA           28100

GGCGACCGGA TAGCAAGACT CTGACAAAGC CCAAGAAATC CACAGCGGCG           28150

GCAGCAGCAG GAGGAGGAGC GCTGCGTCTG GCGCCCAACG AACCCGTATC           28200

GACCCGCGAG CTTAGAAACA GGATTTTTCC CACTCTGTAT GCTATATTTC           28250

AACAGAGCAG GGGCCAAGAA CAAGAGCTGA AAATAAAAAA CAGGTCTCTG           28300
```

-continued

| | |
|---|---|
| CGATCCCTCA CCCGCAGCTG CCTGTATCAC AAAAGCGAAG ATCAGCTTCG | 28350 |
| GCGCACGCTG GAAGACGCGG AGGCTCTCTT CAGTAAATAC TGCGCGCTGA | 28400 |
| CTCTTAAGGA CTAGTTTCGC GCCCTTTCTC AAATTTAAGC GCGAAAACTA | 28450 |
| CGTCATCTCC AGCGGCCACA CCCGGCGCCA GCACCTGTCG TCAGCGCCAT | 28500 |
| TATGAGCAAG GAAATTCCCA CGCCCTACAT GTGGAGTTAC CAGCCACAAA | 28550 |
| TGGGACTTGC GGCTGGAGCT GCCCAAGACT ACTCAACCCG AATAAACTAC | 28600 |
| ATGAGCGCGG GACCCCACAT GATATCCCGG GTCAACGGAA TCCGCGCCCA | 28650 |
| CCGAAACCGA ATTCTCTTGG AACAGGCGGC TATTACCACC ACACCTCGTA | 28700 |
| ATAACCTTAA TCCCCGTAGT TGGCCCGCTG CCCTGGTGTA CCAGGAAAGT | 28750 |
| CCCGCTCCCA CCACTGTGGT ACTTCCCAGA GACGCCCAGG CCGAAGTTCA | 28800 |
| GATGACTAAC TCAGGGCGC AGCTTGCGGG CGGCTTTCGT CACAGGGTGC | 28850 |
| GGTCGCCCGG GCAGGGTATA ACTCACCTGA CAATCAGAGG GCGAGGTATT | 28900 |
| CAGCTCAACG ACGAGTCGGT GAGCTCCTCG CTTGGTCTCC GTCCGGACGG | 28950 |
| GACATTTCAG ATCGGCGGCG CCGGCCGTCC TTCATTCACG CCTCGTCAGG | 29000 |
| CAATCCTAAC TCTGCAGACC TCGTCCTCTG AGCCGCGCTC TGGAGGCATT | 29050 |
| GGAACTCTGC AATTTATTGA GGAGTTTGTG CCATCGGTCT ACTTTAACCC | 29100 |
| CTTCTCGGGA CCTCCCGGCC ACTATCCGGA TCAATTTATT CCTAACTTTG | 29150 |
| ACGCGGTAAA GGACTCGGCG GACGGCTACG ACTGAATGTT AAGTGGAGAG | 29200 |
| GCAGAGCAAC TGCGCCTGAA ACACCTGGTC CACTGTCGCC GCCACAAGTG | 29250 |
| CTTTGCCCGC GACTCCGGTG AGTTTTGCTA CTTTGAATTG CCCGAGGATC | 29300 |
| ATATCGAGGG CCCGGCGCAC GGCGTCCGGC TTACCGCCCA GGGAGAGCTT | 29350 |
| GCCCGTAGCC TGATTCGGGA GTTTACCCAG CGCCCCCTGC TAGTTGAGCG | 29400 |
| GGACAGGGGA CCCTGTGTTC TCACTGTGAT TTGCAACTGT CCTAACCTTG | 29450 |
| GATTACATCA AGATCTTTGT TGCCATCTCT GTGCTGAGTA TAATAAATAC | 29500 |
| AGAAATTAAA ATATACTGGG GCTCCTATCG CCATCCTGTA AACGCCACCG | 29550 |
| TCTTCACCCG CCCAAGCAAA CCAAGGCGAA CCTTACCTGG TACTTTTAAC | 29600 |
| ATCTCTCCCT CTGTGATTTA CAACAGTTTC AACCCAGACG GAGTGAGTCT | 29650 |
| ACGAGAGAAC CTCTCCGAGC TCAGCTACTC CATCAGAAAA AACACCACCC | 29700 |
| TCCTTACCTG CCGGGAACGT ACGAGTGCGT CACCGGCCGC TGCACCACAC | 29750 |
| CTACCGCCTG ACCGTAAACC AGACTTTTTC CGGACAGACC TCAATAACTC | 29800 |
| TGTTTACCAG AACAGGAGGT GAGCTTAGAA AACCCTTAGG GTATTAGGCC | 29850 |
| AAAGGCGCAG CTACTGTGGG GTTTATGAAC AATTCAAGCA ACTCTACGGG | 29900 |
| CTATTCTAAT TCAGGTTTCT CTAGAATCGG GGTTGGGGTT ATTCTCTGTC | 29950 |
| TTGTGATTCT CTTTATTCTT ATACTAACGC TTCTCTGCCT AAGGCTCGCC | 30000 |
| GCCTGCTGTG TGCACATTTG CATTTATTGT CAGCTTTTTA AACGCTGGGG | 30050 |
| TCGCCACCCA AGATGATTAG GTACATAATC CTAGGTTTAC TCACCCTTGC | 30100 |
| GTCAGCCCAC GGTACCACCC AAAAGGTGGA TTTTAAGGAG CCAGCCTGTA | 30150 |
| ATGTTACATT CGCAGCTGAA GCTAATGAGT GCACCACTCT TATAAAATGC | 30200 |
| ACCACAGAAC ATGAAAAGCT GCTTATTCGC CACAAAAACA AAATTGGCAA | 30250 |

```
GTATGCTGTT TATGCTATTT GGCAGCCAGG TGACACTACA GAGTATAATG      30300

TTACAGTTTT CCAGGGTAAA AGTCATAAAA CTTTTATGTA TACTTTTCCA      30350

TTTTATGAAA TGTGCGACAT TACCATGTAC ATGAGCAAAC AGTATAAGTT      30400

GTGGCCCCCA CAAAATTGTG TGGAAAACAC TGGCACTTTC TGCTGCACTG      30450

CTATGCTAAT TACAGTGCTC GCTTTGGTCT GTACCCTACT CTATATTAAA      30500

TACAAAAGCA GACGCAGCTT TATTGAGGAA AGAAAATGC CTTAATTTAC       30550

TAAGTTACAA AGCTAATGTC ACCACTAACT GCTTTACTCG CTGCTTGCAA      30600

AACAAATTCA AAAGTTAGC ATTATAATTA GAATAGGATT TAAACCCCCC      30650

GGTCATTTCC TGCTCAATAC CATTCCCCTG AACAATTGAC TCTATGTGGG      30700

ATATGCTCCA GCGCTACAAC CTTGAAGTCA GGCTTCCTGG ATGTCAGCAT      30750

CTGACTTTGG CCAGCACCTG TCCCGCGGAT TTGTTCCAGT CCAACTACAG      30800

CGACCCACCC TAACAGAGAT GACCAACACA ACCAACGCGG CCGCCGCTAC      30850

CGGACTTACA TCTACCACAA ATACACCCCA AGTTTCTGCC TTTGTCAATA      30900

ACTGGGATAA CTTGGGCATG TGGTGGTTCT CCATAGCGCT TATGTTTGTA      30950

TGCCTTATTA TTATGTGGCT CATCTGCTGC CTAAAGCGCA AACGCGCCCG      31000

ACCACCCATC TATAGTCCCA TCATTGTGCT ACACCCAAAC AATGATGGAA      31050

TCCATAGATT GGACGGACTG AAACACATGT TCTTTTCTCT TACAGTATGA      31100

TTAAATGAGA CATGATTCCT CGAGTTTTTA TATTACTGAC CCTTGTTGCG      31150

CTTTTTTGTG CGTGCTCCAC ATTGGCTGCG GTTTCTCACA TCGAAGTAGA      31200

CTGCATTCCA GCCTTCACAG TCTATTTGCT TTACGGATTT GTCACCCTCA      31250

CGCTCATCTG CAGCCTCATC ACTGTGGTCA TCGCCTTTAT CCAGTGCATT      31300

GACTGGGTCT GTGTGCGCTT TGCATATCTC AGACACCATC CCCAGTACAG      31350

GGACAGGACT ATAGCTGAGC TTCTTAGAAT TCTTTAATTA TGAAATTTAC      31400

TGTGACTTTT CTGCTGATTA TTTGCACCCT ATCTGCGTTT TGTTCCCCGA      31450

CCTCCAAGCC TCAAAGACAT ATATCATGCA GATTCACTCG TATATGGAAT      31500

ATTCCAAGTT GCTACAATGA AAAAAGCGAT CTTTCCGAAG CCTGGTTATA      31550

TGCAATCATC TCTGTTATGG TGTTCTGCAG TACCATCTTA GCCCTAGCTA      31600

TATATCCCTA CCTTGACATT GGCTGGAAAC GAATAGATGC CATGAACCAC      31650

CCAACTTTCC CCGCGCCCGC TATGCTTCCA CTGCAACAAG TTGTTGCCGG      31700

CGGCTTTGTC CCAGCCAATC AGCCTCGCCC CACTTCTCCC ACCCCCACTG      31750

AAATCAGCTA CTTTAATCTA ACAGGAGGAG ATGACTGACA CCCTAGATCT      31800

AGAAATGGAC GGAATTATTA CAGAGCAGCG CCTGCTAGAA AGACGCAGGG      31850

CAGCGGCCGA GCAACAGCGC ATGAATCAAG AGCTCCAAGA CATGGTTAAC      31900

TTGCACCAGT GCAAAAGGGG TATCTTTTGT CTGGTAAAGC AGGCCAAAGT      31950

CACCTACGAC AGTAATACCA CCGGACACCG CCTTAGCTAC AAGTTGCCAA      32000

CCAAGCGTCA GAAATTGGTG GTCATGGTGG GAGAAAAGCC CATTACCATA      32050

ACTCAGCACT CGGTAGAAAC CGAAGGCTGC ATTCACTCAC CTTGTCAAGG      32100

ACCTGAGGAT CTCTGCACCC TTATTAAGAC CCTGTGCGGT CTCAAAGATC      32150

TTATTCCCTT TAACTAATAA AAAAAAATAA TAAAGCATCA CTTACTTAAA      32200

ATCAGTTAGC AAATTTCTGT CCAGTTTATT CAGCAGCACC TCCTTGCCCT      32250
```

```
CCTCCCAGCT CTGGTATTGC AGCTTCCTCC TGGCTGCAAA CTTTCTCCAC      32300

AATCTAAATG GAATGTCAGT TTCCTCCTGT TCCTGTCCAT CCGCACCCAC      32350

TATCTTCATG TTGTTGCAGA TGAAGCGCGC AAGACCGTCT GAAGATACCT      32400

TCAACCCCGT GTATCCATAT GACACGGAAA CCGGTCCTCC AACTGTGCCT      32450

TTTCTTACTC CTCCCTTTGT ATCCCCCAAT GGGTTTCAAG AGAGTCCCCC      32500

TGGGGTACTC TCTTTGCGCC TATCCGAACC TCTAGTTACC TCCAATGGCA      32550

TGCTTGCGCT CAAAATGGGC AACGGCCTCT CTCTGGACGA GGCCGGCAAC      32600

CTTACCTCCC AAAATGTAAC CACTGTGAGC CCACCTCTCA AAAAAACCAA      32650

GTCAAACATA AACCTGGAAA TATCTGCACC CCTCACAGTT ACCTCAGAAG      32700

CCCTAACTGT GGCTGCCGCC GCACCTCTAA TGGTCGCGGG CAACACACTC      32750

ACCATGCAAT CACAGGCCCC GCTAACCGTG CACGACTCCA AACTTAGCAT      32800

TGCCACCCAA GGACCCCTCA CAGTGTCAGA AGGAAAGCTA GCCCTGCAAA      32850

CATCAGGCCC CCTCACCACC ACCGATAGCA GTACCCTTAC TATCACTGCC      32900

TCACCCCCTC TAACTACTGC CACTGGTAGC TTGGGCATTG ACTTGAAAGA      32950

GCCCATTTAT ACACAAAATG GAAAACTAGG ACTAAAGTAC GGGGCTCCTT      33000

TGCATGTAAC AGACGACCTA AACACTTTGA CCGTAGCAAC TGGTCCAGGT      33050

GTGACTATTA ATAATACTTC CTTGCAAACT AAAGTTACTG GAGCCTTGGG      33100

TTTTGATTCA CAAGGCAATA TGCAACTTAA TGTAGCAGGA GGACTAAGGA      33150

TTGATTCTCA AAACAGACGC CTTATACTTG ATGTTAGTTA TCCGTTTGAT      33200

GCTCAAAACC AACTAAATCT AAGACTAGGA CAGGGCCCTC TTTTTATAAA      33250

CTCAGCCCAC AACTTGGATA TTAACTACAA CAAAGGCCTT TACTTGTTTA      33300

CAGCTTCAAA CAATTCCAAA AAGCTTGAGG TTAACCTAAG CACTGCCAAG      33350

GGGTTGATGT TTGACGCTAC AGCCATAGCC ATTAATGCAG GAGATGGGCT      33400

TGAATTTGGT TCACCTAATG CACCAAACAC AAATCCCCTC AAAACAAAAA      33450

TTGGCCATGG CCTAGAATTT GATTCAAACA AGGCTATGGT TCCTAAACTA      33500

GGAACTGGCC TTAGTTTTGA CAGCACAGGT GCCATTACAG TAGGAAACAA      33550

AAATAATGAT AAGCTAACTT TGTGGACCAC ACCAGCTCCA TCTCCTAACT      33600

GTAGACTAAA TGCAGAGAAA GATGCTAAAC TCACTTTGGT CTTAACAAAA      33650

TGTGGCAGTC AAATACTTGC TACAGTTTCA GTTTTGGCTG TTAAAGGCAG      33700

TTTGGCTCCA ATATCTGGAA CAGTTCAAAG TGCTCATCTT ATTATAAGAT      33750

TTGACGAAAA TGGAGTGCTA CTAAACAATT CCTTCCTGGA CCCAGAATAT      33800

TGGAACTTTA GAAATGGAGA TCTTACTGAA GGCACAGCCT ATACAAACGC      33850

TGTTGGATTT ATGCCTAACC TATCAGCTTA TCCAAAATCT CACGGTAAAA      33900

CTGCCAAAAG TAACATTGTC AGTCAAGTTT ACTTAAACGG AGACAAAACT      33950

AAACCTGTAA CACTAACCAT TACACTAAAC GGTACACAGG AAACAGGAGA      34000

CACAACTCCA AGTGCATACT CTATGTCATT TTCATGGGAC TGGTCTGGCC      34050

ACAACTACAT TAATGAAATA TTTGCCACAT CCTCTTACAC TTTTTCATAC      34100

ATTGCCCAAG AATAAAGAAT CGTTTGTGTT ATGTTTCAAC GTGTTTATTT      34150

TTCAATTGCA GAAAATTTCA AGTCATTTTT CATTCAGTAG TATAGCCCCA      34200
```

```
CCACCACATA GCTTATACAG ATCACCGTAC CTTAATCAAA CTCACAGAAC        34250

CCTAGTATTC AACCTGCCAC CTCCCTCCCA ACACACAGAG TACACAGTCC        34300

TTTCTCCCCG GCTGGCCTTA AAAAGCATCA TATCATGGGT AACAGACATA        34350

TTCTTAGGTG TTATATTCCA CACGGTTTCC TGTCGAGCCA AACGCTCATC        34400

AGTGATATTA ATAAACTGGC GGCGATATAA AATGCAAGGT GCTGCTCAAA        34450

AAATCAGGCA AGCCTCGCG CAAAAAGAA AGCACATCGT AGTCATGCTC          34500

ATGCAGATAA AGGCAGGTAA GCTCCGGAAC CACCACAGAA AAAGACACCA        34550

TTTTTCTCTC AAACATGTCT GCGGGTTTCT GCATAAACAC AAAATAAAAT        34600

AACAAAAAAA CATTTAAACA TTAGAAGCCT GTCTTACAAC AGGAAAAACA        34650

ACCCTTATAA GCATAAGACG GACTACGGCC ATGCCGGCGT GACCGTAAAA        34700

AAACTGGTCA CCGTGATTAA AAAGCACCAC CGACAGCTCC TCGGTCATGT        34750

CCGGAGTCAT AATGTAAGAC TCGGTAAACA CATCAGGTTG ATTCATCGGT        34800

CAGTGCTAAA AAGCGACCGA AATAGCCCGG GGGAATACAT ACCCGCAGGC        34850

GTAGAGACAA CATTACAGCC CCCATAGGAG GTATAACAAA ATTAATAGGA        34900

GAGAAAAACA CATAAACACC TGAAAAACCC TCCTGCCTAG GCAAAATAGC        34950

ACCCTCCCGC TCCAGAACAA CATACAGCGC TTCACAGCGG CAGCCTAACA        35000

GTCAGCCTTA CCAGTAAAAA AGAAAACCTA TTAAAAAAAC ACCACTCGAC        35050

ACGGCACCAG CTCAATCAGT CACAGTGTAA AAAAGGGCCA AGTGCAGAGC        35100

GAGTATATAT AGGACTAAAA AATGACGTAA CGGTTAAAGT CCACAAAAAA        35150

CACCCAGAAA ACCGCACGCG AACCTACGCC CAGAAACGAA AGCCAAAAAA        35200

CCCACAACTT CCTCAAATCG TCACTTCCGT TTTCCCACGT TACGTAACTT        35250

CCCATTTTAA GAAAACTACA ATTCCCAACA CATACAAGTT ACTCCGCCCT        35300

AAAACCTACG TCACCCGCCC CGTTCCCACG CCCCGCGCCA CGTCACAAAC        35350

TCCACCCCCT CATTATCATA TTGGCTTCAA TCCAAAATAA GGTATATTAT        35400

TGATGATG                                                     35408

(2) INFORMATION FOR SEQ ID NO: 4:

(i) SEQUENCE CHARACTERISTICS:
        (A) LENGTH: 8509 base pairs
        (B) TYPE: nucleic acid
        (C) STRANDEDNESS: double
        (D) TOPOLOGY: not relevant (ii) MOLECULE TYPE: cDNA (xi) SEQUENCE DESCRIPTION: SEQ ID NO: 4:

GCCCAATACG CAAACCGCCT CTCCCCGCGC GTTGGCCGAT TCATTAATGC           50

AGCTGCGCGC TCGCTCGCTC ACTGAGGCCG CCCGGGCAAA GCCCGGGCGT          100

CGGGCGACCT TTGGTCGCCC GGCCTCAGTG AGCGAGCGAG CGCGCAGAGA          150

GGGAGTGGCC AACTCCATCA CTAGGGGTTC CTTGTAGTTA ATGATTAACC          200

CGCCATGCTA CTTATCTACG TAGCCATTCT CTAGCCCCTG CAGGTCGTTA          250

CATAACTTAC GGTAAATGGC CCGCCTGGCT GACCGCCCAA CGACCCCCGC          300

CCATTGACGT CAATAATGAC GTATGTTCCC ATAGTAACGC CAATAGGGAC          350

TTTCCATTGA CGTCAATGGG TGGAGTATTT ACGGTAAACT GCCCACTTGG          400
```

-continued

| | |
|---|---|
| CAGTACATCA AGTGTATCAT ATGCCAAGTA CGCCCCCTAT TGACGTCAAT | 450 |
| GACGGTAAAT GGCCCGCCTG GCATTATGCC CAGTACATGA CCTTATGGGA | 500 |
| CTTTCCTACT TGGCAGTACA TCTACGTATT AGTCATCGCT ATTACCATGG | 550 |
| TGATGCGGTT TTGGCAGTAC ATCAATGGGC GTGGATAGCG GTTTGACTCA | 600 |
| CGGGGATTTC CAAGTCTCCA CCCCATTGAC GTCAATGGGA GTTTGTTTTG | 650 |
| GCACCAAAAT CAACGGGACT TTCCAAAATG TCGTAACAAC TCCGCCCCAT | 700 |
| TGACGCAAAT GGGCGGTAGG CGTGTACGGT GGGAGGTCTA TATAAGCAGA | 750 |
| GCTCGTTTAG TGAACCGTCA GATCGCCTGG AGACGCCATC CACGCTGTTT | 800 |
| TGACCTCCAT AGAAGACACC GGGACCGATC CAGCCTCCGG ACTCTAGAGG | 850 |
| ATCCGGTACT CGAGGAACTG AAAAACCAGA AAGTTAACTG GTAAGTTTAG | 900 |
| TCTTTTTGTC TTTTATTTCA GGTCCCGGAT CCGGTGGTGG TGCAAATCAA | 950 |
| AGAACTGCTC CTCAGTGGAT GTTGCCTTTA CTTCTAGGCC TGTACGGAAG | 1000 |
| TGTTACTTCT GCTCTAAAAG CTGCGGAATT GTACCCGCGG CCGCAATTCC | 1050 |
| CGGGGATCGA AAGAGCCTGC TAAAGCAAAA AAGAAGTCAC CATGTCGTTT | 1100 |
| ACTTTGACCA ACAAGAACGT GATTTTCGTT GCCGGTCTGG GAGGCATTGG | 1150 |
| TCTGGACACC AGCAAGGAGC TGCTCAAGCG CGATCCCGTC GTTTTACAAC | 1200 |
| GTCGTGACTG GGAAAACCCT GGCGTTACCC AACTTAATCG CCTTGCAGCA | 1250 |
| CATCCCCCTT TCGCCAGCTG GCGTAATAGC GAAGAGGCCC GCACCGATCG | 1300 |
| CCCTTCCCAA CAGTTGCGCA GCCTGAATGG CGAATGGCGC TTTGCCTGGT | 1350 |
| TTCCGGCACC AGAAGCGGTG CCGGAAAGCT GGCTGGAGTG CGATCTTCCT | 1400 |
| GAGGCCGATA CTGTCGTCGT CCCCTCAAAC TGGCAGATGC ACGGTTACGA | 1450 |
| TGCGCCCATC TACACCAACG TAACCTATCC CATTACGGTC AATCCGCCGT | 1500 |
| TTGTTCCCAC GGAGAATCCG ACGGGTTGTT ACTCGCTCAC ATTTAATGTT | 1550 |
| GATGAAAGCT GGCTACAGGA AGGCCAGACG CGAATTATTT TTGATGGCGT | 1600 |
| TAACTCGGCG TTTCATCTGT GGTGCAACGG GCGCTGGGTC GGTTACGGCC | 1650 |
| AGGACAGTCG TTTGCCGTCT GAATTTGACC TGAGCGCATT TTTACGCGCC | 1700 |
| GGAGAAAACC GCCTCGCGGT GATGGTGCTG CGTTGGAGTG ACGGCAGTTA | 1750 |
| TCTGGAAGAT CAGGATATGT GGCGGATGAG CGGCATTTTC CGTGACGTCT | 1800 |
| CGTTGCTGCA TAAACCGACT ACACAAATCA GCGATTTCCA TGTTGCCACT | 1850 |
| CGCTTTAATG ATGATTTCAG CCGCGCTGTA CTGGAGGCTG AAGTTCAGAT | 1900 |
| GTGCGGCGAG TTGCGTGACT ACCTACGGGT AACAGTTTCT TTATGGCAGG | 1950 |
| GTGAAACGCA GGTCGCCAGC GGCACCGCGC CTTTCGGCGG TGAAATTATC | 2000 |
| GATGAGCGTG GTGGTTATGC CGATCGCGTC ACACTACGTC TGAACGTCGA | 2050 |
| AAACCCGAAA CTGTGGAGCG CCGAAATCCC GAATCTCTAT CGTGCGGTGG | 2100 |
| TTGAACTGCA CACCGCCGAC GGCACGCTGA TTGAAGCAGA AGCCTGCGAT | 2150 |
| GTCGGTTTCC GCGAGGTGCG GATTGAAAAT GGTCTGCTGC TGCTGAACGG | 2200 |
| CAAGCCGTTG CTGATTCGAG GCGTTAACCG TCACGAGCAT CATCCTCTGC | 2250 |
| ATGGTCAGGT CATGGATGAG CAGACGATGG TGCAGGATAT CCTGCTGATG | 2300 |
| AAGCAGAACA ACTTTAACGC CGTGCGCTGT TCGCATTATC CGAACCATCC | 2350 |
| GCTGTGGTAC ACGCTGTGCG ACCGCTACGG CCTGTATGTG GTGGATGAAG | 2400 |

-continued

| | |
|---|---|
| CCAATATTGA AACCCACGGC ATGGTGCCAA TGAATCGTCT GACCGATGAT | 2450 |
| CCGCGCTGGC TACCGGCGAT GAGCGAACGC GTAACGCGAA TGGTGCAGCG | 2500 |
| CGATCGTAAT CACCCGAGTG TGATCATCTG GTCGCTGGGG AATGAATCAG | 2550 |
| GCCACGGCGC TAATCACGAC GCGCTGTATC GCTGGATCAA ATCTGTCGAT | 2600 |
| CCTTCCCGCC CGGTGCAGTA TGAAGGCGGC GGAGCCGACA CCACGGCCAC | 2650 |
| CGATATTATT TGCCCGATGT ACGCGCGCGT GGATGAAGAC CAGCCCTTCC | 2700 |
| CGGCTGTGCC GAAATGGTCC ATCAAAAAAT GGCTTTCGCT ACCTGGAGAG | 2750 |
| ACGCGCCCGC TGATCCTTTG CGAATACGCC CACGCGATGG GTAACAGTCT | 2800 |
| TGGCGGTTTC GCTAAATACT GGCAGGCGTT TCGTCAGTAT CCCCGTTTAC | 2850 |
| AGGGCGGCTT CGTCTGGGAC TGGGTGGATC AGTCGCTGAT TAAATATGAT | 2900 |
| GAAAACGGCA ACCCGTGGTC GGCTTACGGC GGTGATTTTG GCGATACGCC | 2950 |
| GAACGATCGC CAGTTCTGTA TGAACGGTCT GGTCTTTGCC GACCGCACGC | 3000 |
| CGCATCCAGC GCTGACGGAA GCAAAACACC AGCAGCAGTT TTTCCAGTTC | 3050 |
| CGTTTATCCG GCAAACCAT CGAAGTGACC AGCGAATACC TGTTCCGTCA | 3100 |
| TAGCGATAAC GAGCTCCTGC ACTGGATGGT GGCGCTGGAT GGTAAGCCGC | 3150 |
| TGGCAAGCGG TGAAGTGCCT CTGGATGTCG CTCCACAAGG TAAACAGTTG | 3200 |
| ATTGAACTGC CTGAACTACC GCAGCCGGAG AGCGCCGGGC AACTCTGGCT | 3250 |
| CACAGTACGC GTAGTGCAAC CGAACGCGAC CGCATGGTCA GAAGCCGGGC | 3300 |
| ACATCAGCGC CTGGCAGCAG TGGCGTCTGG CGGAAAACCT CAGTGTGACG | 3350 |
| CTCCCCGCCG CGTCCCACGC CATCCCGCAT CTGACCACCA GCGAAATGGA | 3400 |
| TTTTTGCATC GAGCTGGGTA ATAAGCGTTG GCAATTTAAC CGCCAGTCAG | 3450 |
| GCTTTCTTTC ACAGATGTGG ATTGGCGATA AAAAACAACT GCTGACGCCG | 3500 |
| CTGCGCGATC AGTTCACCCG TGCACCGCTG GATAACGACA TTGGCGTAAG | 3550 |
| TGAAGCGACC CGCATTGACC CTAACGCCTG GGTCGAACGC TGGAAGGCGG | 3600 |
| CGGGCCATTA CCAGGCCGAA GCAGCGTTGT TGCAGTGCAC GGCAGATACA | 3650 |
| CTTGCTGATG CGGTGCTGAT TACGACCGCT CACGCGTGGC AGCATCAGGG | 3700 |
| GAAAACCTTA TTTATCAGCC GGAAAACCTA CCGGATTGAT GGTAGTGGTC | 3750 |
| AAATGGCGAT TACCGTTGAT GTTGAAGTGG CGAGCGATAC ACCGCATCCG | 3800 |
| GCGCGGATTG GCCTGAACTG CCAGCTGGCG CAGGTAGCAG AGCGGGTAAA | 3850 |
| CTGGCTCGGA TTAGGGCCGC AAGAAAACTA TCCCGACCGC CTTACTGCCG | 3900 |
| CCTGTTTTGA CCGCTGGGAT CTGCCATTGT CAGACATGTA TACCCCGTAC | 3950 |
| GTCTTCCCGA GCGAAAACGG TCTGCGCTGC GGGACGCGCG AATTGAATTA | 4000 |
| TGGCCCACAC CAGTGGCGCG GCGACTTCCA GTTCAACATC AGCCGCTACA | 4050 |
| GTCAACAGCA ACTGATGGAA ACCAGCCATC GCCATCTGCT GCACGCGGAA | 4100 |
| GAAGGCACAT GGCTGAATAT CGACGGTTTC CATATGGGGA TTGGTGGCGA | 4150 |
| CGACTCCTGG AGCCCGTCAG TATCGGCGGA ATTACAGCTG AGCGCCGGTC | 4200 |
| GCTACCATTA CCAGTTGGTC TGGTGTCAAA ATAATAATA ACCGGGCAGG | 4250 |
| CCATGTCTGC CCGTATTTCG CGTAAGGAAA TCCATTATGT ACTATTTAAA | 4300 |
| AAACACAAAC TTTTGGATGT TCGGTTTATT CTTTTTCTTT TACTTTTTTA | 4350 |

| | |
|---|---|
| TCATGGGAGC CTACTTCCCG TTTTTCCCGA TTTGGCTACA TGACATCAAC | 4400 |
| CATATCAGCA AAAGTGATAC GGGTATTATT TTTGCCGCTA TTTCTCTGTT | 4450 |
| CTCGCTATTA TTCCAACCGC TGTTTGGTCT GCTTTCTGAC AAACTCGGCC | 4500 |
| TCGACTCTAG GCGGCCGCGG GGATCCAGAC ATGATAAGAT ACATTGATGA | 4550 |
| GTTTGGACAA ACCACAACTA GAATGCAGTG AAAAAAATGC TTTATTTGTG | 4600 |
| AAATTTGTGA TGCTATTGCT TTATTTGTAA CCATTATAAG CTGCAATAAA | 4650 |
| CAAGTTAACA ACAACAATTG CATTCATTTT ATGTTTCAGG TTCAGGGGGA | 4700 |
| GGTGTGGGAG GTTTTTTCGG ATCCTCTAGA GTCGACCTGC AGGGGCTAGA | 4750 |
| ATGGCTACGT AGATAAGTAG CATGGCGGGT TAATCATTAA CTACAAGGAA | 4800 |
| CCCCTAGTGA TGGAGTTGGC CACTCCCTCT CTGCGCGCTC GCTCGCTCAC | 4850 |
| TGAGGCCGGG CGACCAAAGG TCGCCCGACG CCCGGGCTTT GCCCGGGCGG | 4900 |
| CCTCAGTGAG CGAGCGAGCG CGCAGCTGGC GTAATAGCGA AGAGGCCCGC | 4950 |
| ACCGATCGCC CTTCCCAACA GTTGCGCAGC CTGAATGGCG AATGGAATTC | 5000 |
| CAGACGATTG AGCGTCAAAA TGTAGGTATT TCCATGAGCG TTTTTCCTGT | 5050 |
| TGCAATGGCT GGCGGTAATA TTGTTCTGGA TATTACCAGC AAGGCCGATA | 5100 |
| GTTTGAGTTC TTCTACTCAG GCAAGTGATG TTATTACTAA TCAAAGAAGT | 5150 |
| ATTGCGACAA CGGTTAATTT GCGTGATGGA CAGACTCTTT TACTCGGTGG | 5200 |
| CCTCACTGAT TATAAAAACA CTTCTCAGGA TTCTGGCGTA CCGTTCCTGT | 5250 |
| CTAAAATCCC TTTAATCGGC CTCCTGTTTA GCTCCCGCTC TGATTCTAAC | 5300 |
| GAGGAAAGCA CGTTATACGT GCTCGTCAAA GCAACCATAG TACGCGCCCT | 5350 |
| GTAGCGGCGC ATTAAGCGCG GCGGGTGTGG TGGTTACGCG CAGCGTGACC | 5400 |
| GCTACACTTG CCAGCGCCCT AGCGCCCGCT CCTTTCGCTT TCTTCCCTTC | 5450 |
| CTTTCTCGCC ACGTTCGCCG GCTTTCCCCG TCAAGCTCTA AATCGGGGGC | 5500 |
| TCCCTTTAGG GTTCCGATTT AGTGCTTTAC GGCACCTCGA CCCCAAAAAA | 5550 |
| CTTGATTAGG GTGATGGTTC ACGTAGTGGG CCATCGCCCT GATAGACGGT | 5600 |
| TTTTCGCCCT TTGACGTTGG AGTCCACGTT CTTTAATAGT GGACTCTTGT | 5650 |
| TCCAAACTGG AACAACACTC AACCCTATCT CGGTCTATTC TTTTGATTTA | 5700 |
| TAAGGGATTT TGCCGATTTC GGCCTATTGG TTAAAAAATG AGCTGATTTA | 5750 |
| ACAAAAATTT AACGCGAATT TTAACAAAAT ATTAACGTTT ACAATTTAAA | 5800 |
| TATTTGCTTA TACAATCTTC CTGTTTTTGG GGCTTTTCTG ATTATCAACC | 5850 |
| GGGGTACATA TGATTGACAT GCTAGTTTTA CGATTACCGT TCATCGATTC | 5900 |
| TCTTGTTTGC TCCAGACTCT CAGGCAATGA CCTGATAGCC TTTGTAGAGA | 5950 |
| CCTCTCAAAA ATAGCTACCC TCTCCGGCAT GAATTTATCA GCTAGAACGG | 6000 |
| TTGAATATCA TATTGATGGT GATTTGACTG TCTCCGGCCT TTCTCACCCG | 6050 |
| TTTGAATCTT TACCTACACA TTACTCAGGC ATTGCATTTA AAATATATGA | 6100 |
| GGGTTCTAAA AATTTTTATC CTTGCGTTGA ATAAAGGCT TCTCCCGCAA | 6150 |
| AAGTATTACA GGGTCATAAT GTTTTTGGTA CAACCGATTT AGCTTTATGC | 6200 |
| TCTGAGGCTT TATTGCTTAA TTTTGCTAAT TCTTTGCCTT GCCTGTATGA | 6250 |
| TTTATTGGAT GTTGGAATTC CTGATGCGGT ATTTTCTCCT TACGCATCTG | 6300 |
| TGCGGTATTT CACACCGCAT ATGGTGCACT CTCAGTACAA TCTGCTCTGA | 6350 |

| | |
|---|---|
| TGCCGCATAG TTAAGCCAGC CCCGACACCC GCCAACACCC GCTGACGCGC | 6400 |
| CCTGACGGGC TTGTCTGCTC CCGGCATCCG CTTACAGACA AGCTGTGACC | 6450 |
| GTCTCCGGGA GCTGCATGTG TCAGAGGTTT TCACCGTCAT CACCGAAACG | 6500 |
| CGCGAGACGA AAGGGCCTCG TGATACGCCT ATTTTTATAG GTTAATGTCA | 6550 |
| TGATAATAAT GGTTTCTTAG ACGTCAGGTG GCACTTTTCG GGGAAATGTG | 6600 |
| CGCGGAACCC CTATTTGTTT ATTTTTCTAA ATACATTCAA ATATGTATCC | 6650 |
| GCTCATGAGA CAATAACCCT GATAAATGCT TCAATAATAT TGAAAAGGA | 6700 |
| AGAGTATGAG TATTCAACAT TTCCGTGTCG CCCTTATTCC CTTTTTTGCG | 6750 |
| GCATTTTGCC TTCCTGTTTT TGCTCACCCA GAAACGCTGG TGAAAGTAAA | 6800 |
| AGATGCTGAA GATCAGTTGG GTGCACGAGT GGGTTACATC GAACTGGATC | 6850 |
| TCAACAGCGG TAAGATCCTT GAGAGTTTTC GCCCCGAAGA ACGTTTTCCA | 6900 |
| ATGATGAGCA CTTTTAAAGT TCTGCTATGT GGCGCGGTAT TATCCCGTAT | 6950 |
| TGACGCCGGG CAAGAGCAAC TCGGTCGCCG CATACACTAT TCTCAGAATG | 7000 |
| ACTTGGTTGA GTACTCACCA GTCACAGAAA AGCATCTTAC GGATGGCATG | 7050 |
| ACAGTAAGAG AATTATGCAG TGCTGCCATA ACCATGAGTG ATAACACTGC | 7100 |
| GGCCAACTTA CTTCTGACAA CGATCGGAGG ACCGAAGGAG CTAACCGCTT | 7150 |
| TTTTGCACAA CATGGGGGAT CATGTAACTC GCCTTGATCG TTGGGAACCG | 7200 |
| GAGCTGAATG AAGCCATACC AAACGACGAG CGTGACACCA CGATGCCTGT | 7250 |
| AGCAATGGCA ACAACGTTGC GCAAACTATT AACTGGCGAA CTACTTACTC | 7300 |
| TAGCTTCCCG GCAACAATTA ATAGACTGGA TGGAGGCGGA TAAAGTTGCA | 7350 |
| GGACCACTTC TGCGCTCGGC CCTTCCGGCT GGCTGGTTTA TTGCTGATAA | 7400 |
| ATCTGGAGCC GGTGAGCGTG GGTCTCGCGG TATCATTGCA GCACTGGGGC | 7450 |
| CAGATGGTAA GCCCTCCCGT ATCGTAGTTA TCTACACGAC GGGGAGTCAG | 7500 |
| GCAACTATGG ATGAACGAAA TAGACAGATC GCTGAGATAG GTGCCTCACT | 7550 |
| GATTAAGCAT TGGTAACTGT CAGACCAAGT TTACTCATAT ATACTTTAGA | 7600 |
| TTGATTTAAA ACTTCATTTT TAATTTAAAA GGATCTAGGT GAAGATCCTT | 7650 |
| TTTGATAATC TCATGACCAA AATCCCTTAA CGTGAGTTTT CGTTCCACTG | 7700 |
| AGCGTCAGAC CCCGTAGAAA AGATCAAAGG ATCTTCTTGA GATCCTTTTT | 7750 |
| TTCTGCGCGT AATCTGCTGC TTGCAAACAA AAAAACCACC GCTACCAGCG | 7800 |
| GTGGTTTGTT TGCCGGATCA AGAGCTACCA ACTCTTTTTC CGAAGGTAAC | 7850 |
| TGGCTTCAGC AGAGCGCAGA TACCAAATAC TGTCCTTCTA GTGTAGCCGT | 7900 |
| AGTTAGGCCA CCACTTCAAG AACTCTGTAG CACCGCCTAC ATACCTCGCT | 7950 |
| CTGCTAATCC TGTTACCAGT GGCTGCTGCC AGTGGCGATA AGTCGTGTCT | 8000 |
| TACCGGGTTG GACTCAAGAC GATAGTTACC GGATAAGGCG CAGCGGTCGG | 8050 |
| GCTGAACGGG GGGTTCGTGC ACACAGCCCA GCTTGGAGCG AACGACCTAC | 8100 |
| ACCGAACTGA GATACCTACA GCGTGAGCTA TGAGAAAGCG CCACGCTTCC | 8150 |
| CGAAGGGAGA AAGGCGGACA GGTATCCGGT AAGCGGCAGG GTCGGAACAG | 8200 |
| GAGAGCGCAC GAGGGAGCTT CCAGGGGGAA ACGCCTGGTA TCTTTATAGT | 8250 |
| CCTGTCGGGT TTCGCCACCT CTGACTTGAG CGTCGATTTT TGTGATGCTC | 8300 |

```
GTCAGGGGGG CGGAGCCTAT GGAAAAACGC CAGCAACGCG GCCTTTTTAC       8350

GGTTCCTGGC CTTTTGCTGG CCTTTTGCTC ACATGTTCTT TCCTGCGTTA       8400

TCCCCTGATT CTGTGGATAA CCGTATTACC GCCTTTGAGT GAGCTGATAC       8450

CGCTCGCCGC AGCCGAACGA CCGAGCGCAG CGAGTCAGTG AGCGAGGAAG       8500

CGGAAGAGC                                                    8509
```

(2) INFORMATION FOR SEQ ID NO: 5:

(i) SEQUENCE CHARACTERISTICS:
        (A) LENGTH: 8299 base pairs
        (B) TYPE: nucleic acid
        (C) STRANDEDNESS: double
        (D) TOPOLOGY: not relevant (ii) MOLECULE TYPE: cDNA (xi) SEQUENCE DESCRIPTION: SEQ ID NO: 5:

```
GCCCAATACG CAAACCGCCT CTCCCCGCGC GTTGGCCGAT TCATTAATGC         50

AGCTGCGCGC TCGCTCGCTC ACTGAGGCCG CCCGGGCAAA GCCCGGGCGT        100

CGGGCGACCT TTGGTCGCCC GGCCTCAGTG AGCGAGCGAG CGCGCAGAGA        150

GGGAGTGGCC AACTCCATCA CTAGGGGTTC CTTGTAGTTA ATGATTAACC        200

CGCCATGCTA CTTATCTACA TCATCGATGA ATTCGAGCTT GCATGCCTGC        250

AGGTCGTTAC ATAACTTACG GTAAATGGCC CGCCTGGCTG ACCGCCCAAC        300

GACCCCCGCC CATTGACGTC AATAATGACG TATGTTCCCA TAGTAACGCC        350

AATAGGGACT TTCCATTGAC GTCAATGGGT GGAGTATTTA CGGTAAACTG        400

CCCACTTGGC AGTACATCAA GTGTATCATA TGCCAAGTAC GCCCCCTATT        450

GACGTCAATG ACGGTAAATG GCCCGCCTGG CATTATGCCC AGTACATGAC        500

CTTATGGGAC TTTCCTACTT GGCAGTACAT CTACGTATTA GTCATCGCTA        550

TTACCATGGT GATGCGGTTT TGGCAGTACA TCAATGGGCG TGGATAGCGG        600

TTTGACTCAC GGGGATTTCC AAGTCTCCAC CCCATTGACG TCAATGGGAG        650

TTTGTTTTGG CACCAAAATC AACGGGACTT TCCAAAATGT CGTAACAACT        700

CCGCCCCATT GACGCAAATG GGCGGTAGGC GTGTACGGTG GGAGGTCTAT        750

ATAAGCAGAG CTCGTTTAGT GAACCGTCAG ATCGCCTGGA GACGCCATCC        800

ACGCTGTTTT GACCTCCATA GAAGACACCG GGACCGATCC AGCCTCCGGA        850

CTCTAGAGGA TCCGGTACTC GACCCGAGCT CGGATCCACT AGTAACGGCC        900

GCCAGTGTGC TGGAATTCTG CACTCCAGGC TGCCCGGGTT TGCATGCTGC        950

TGCTGCTGCT GCTGCTGGGC CTGAGGCTAC AGCTCTCCCT GGGCATCATC       1000

CTAGTTGAGG AGGAGAACCC GGACTTCTGG AACCGCGAGG CAGCCGAGGC       1050

CCTGGGTGCC GCCAAGAAGC TGCAGCCTGC ACAGACAGCC GCCAAGAACC       1100

TCATCATCTT CCTGGGCGAT GGGATGGGGG TGTCTACGGT GACAGCTGCC       1150

AGGATCCTAA AAGGGCAGAA GAAGGACAAA CTGGGGCCTG AGATACCCCT       1200

GGCCATGGAC CGCTTCCCAT ATGTGGCTCT GTCCAAGACA TACAATGTAG       1250

ACAAACATGT GCCAGACAGT GGAGCCACAG CCACGGCCTA CCTGTGCGGG       1300

GTCAAGGGCA ACTTCCAGAC CATTGGCTTG AGTGCAGCCG CCCGCTTTAA       1350

CCAGTGCAAC ACGACACGCG GCAACGAGGT CATCTCCGTG ATGAATCGGG       1400
```

-continued

| | |
|---|---|
| CCAAGAAAGC AGGGAAGTCA GTGGGAGTGG TAACCACCAC ACGAGTGCAG | 1450 |
| CACGCCTCGC CAGCCGGCAC CTACGCCCAC ACGGTGAACC GCAACTGGTA | 1500 |
| CTCGGACGCC GACGTGCCTG CCTCGGCCCG CCAGGAGGGG TGCCAGGACA | 1550 |
| TCGCTACGCA GCTCATCTCC AACATGGACA TTGATGTGAT CCTAGGTGGA | 1600 |
| GGCCGAAAGT ACATGTTTCG CATGGGAACC CCAGACCCTG AGTACCCAGA | 1650 |
| TGACTACAGC CAAGGTGGGA CCAGGCTGGA CGGGAAGAAT CTGGTGCAGG | 1700 |
| AATGGCTCGG CGAACGCCAG GGTGCCCGGT ACGTGTGGAA CCGCACTGAG | 1750 |
| CTCATGCAGG CTTCCCTGGA CCCGTCTGTG ACCCATCTCA TGGGTCTCTT | 1800 |
| TGAGCCTGGA GACATGAAAT ACGAGATCCA CCGAGACTCC ACACTGGACC | 1850 |
| CCTCCCTGAT GGAGATGACA GAGGCTGCCC TGCGCCTGCT GAGCAGACAC | 1900 |
| CCCCGCGGCT TCTTCCTCTT CGTGGAGGGT GGTCGCATCG ACCATGGTCA | 1950 |
| TCATGAAAGC AGGGCTTACC GGGCACTGAC TGAGACGATC ATGTTCGACG | 2000 |
| ACGCCATTGA GAGGCGGGC CAGCTCACCA GCGAGGAGGA CACGCTGAGC | 2050 |
| CTCGTCACTG CCGACCACTC CCACGTCTTC TCCTTCGGAG GCTACCCCCT | 2100 |
| GCGAGGGAGC TCCTTCATCG GGCTGGCCGC TGGCAAGGCC CGGGACAGGA | 2150 |
| AGGCCTACAC GGTCCTCCTA TACGGAAACG GTCCAGGCTA TGTGCTCAAG | 2200 |
| GACGGCGCCC GGCCGGATGT TACCGAGAGC GAGAGCGGGA GCCCCGAGTA | 2250 |
| TCGGCAGCAG TCAGCAGTGC CCCTGGACGA AGAGACCCAC GCAGGCGAGG | 2300 |
| ACGTGGCGGT GTTCGCGCGC GGCCCGCAGG CGCACCTGGT TCACGGCGTG | 2350 |
| CAGGAGCAGA CCTTCATAGC GCACGTCATG GCCTTCGCCG CCTGCCTGGA | 2400 |
| GCCCTACACC GCCTGCGACC TGGCGCCCCC CGCCGGCACC ACCGACGCCG | 2450 |
| CGCACCCGGG GCGGTCCGTG GTCCCCGCGT TGCTTCCTCT GCTGGCCGGG | 2500 |
| ACCCTGCTGC TGCTGGAGAC GGCCACTGCT CCCTGAGTGT CCCGTCCCTG | 2550 |
| GGGCTCCTGC TTCCCCATCC CGGAGTTCTC CTGCTCCCCA CCTCCTGTCG | 2600 |
| TCCTGCCTGG CCTCCAGCCC GAGTCGTCAT CCCCGGAGTC CCTATACAGA | 2650 |
| GGTCCTGCCA TGGAACCTTC CCCTCCCCGT GCGCTCTGGG GACTGAGCCC | 2700 |
| ATGACACCAA ACCTGCCCCT TGGCTGCTCT CGGACTCCCT ACCCCAACCC | 2750 |
| CAGGGACTGC AGGTTGTGCC CTGTGGCTGC CTGCACCCCA GGAAAGGAGG | 2800 |
| GGGCTCAGGC CATCCAGCCA CCACCTACAG CCCAGTGGGG TCGAGACAGA | 2850 |
| TGGTCAGTCT GGAGGATGAC GTGGCGTGAA GCTGGCCGCG GGGATCCAGA | 2900 |
| CATGATAAGA TACATTGATG AGTTTGGACA AACCACAACT AGAATGCAGT | 2950 |
| GAAAAAAATG CTTTATTTGT GAAATTTGTG ATGCTATTGC TTTATTTGTA | 3000 |
| ACCATTATAA GCTGCAATAA ACAAGTTAAC AACAACAATT GCATTCATTT | 3050 |
| TATGTTTCAG GTTCAGGGGG AGGTGTGGGA GGTTTTTTCG GATCCTCTAG | 3100 |
| AGTCGACTCT AGANNNNNNN NNNNNNNNNN NNNNNNNNNN NNNNNNNNNN | 3150 |
| NNNNNNNNNN NNNNNNNNNN NNNNNNNNNN NNNNNNNNNN NNNNNNNNNN | 3200 |
| NNNNNNNNNN NNNNNNNNNN NNNNNNNNNN NNNNNNNNNN NNNNNNNNNN | 3250 |
| NNNNNNNNNN NNNNNNNNNN NNNNNNNNNN NNNNNNNNNN NNNNNNNNNN | 3300 |
| NNNNNNNNNN NNNNNNNNNN NNNNNNNNNN NNNNNNNNNN NNNNNNNNNN | 3350 |
| NNNNNNNNNN NNNNNNNNNN NNNNNNNNNN NNNNNNNNNN NNNGGATCCC | 3400 |

```
CATGACTACG TCCGGCGTTC CATTTGGCAT GACACTACGA CCAACACGAT      3450

CTCGGTTGTC TCGGCGCACT CCGTACAGTA GGGATCGTCT ACCTCCTTTT      3500

GAGACAGAAA CCCGCGCTAC CATACTGGAG GATCATCCGC TGCTGCCCGA      3550

ATGTAACACT TTGACAATGC ACAACGTGAG TTACGTGCGA GGTCTTCCCT      3600

GCAGTGTGGG ATTTACGCTG ATTCAGGAAT GGGTTGTTCC CTGGGATATG      3650

GTTCTAACGC GGGAGGAGCT TGTAATCCTG AGGAAGTGTA TGCACGTGTG      3700

CCTGTGTTGT GCCAACATTG ATATCATGAC GAGCATGATG ATCCATGGTT      3750

ACGAGTCCTG GGCTCTCCAC TGTCATTGTT CCAGTCCCGG TTCCCTGCAG      3800

TGTATAGCCG GCGGGCAGGT TTTGGCCAGC TGGTTTAGGA TGGTGGTGGA      3850

TGGCGCCATG TTTAATCAGA GGTTTATATG GTACCGGGAG GTGGTGAATT      3900

ACAACATGCC AAAAGAGGTA ATGTTTATGT CCAGCGTGTT TATGAGGGGT      3950

CGCCACTTAA TCTACCTGCG CTTGTGGTAT GATGGCCACG TGGGTTCTGT      4000

GGTCCCCGCC ATGAGCTTTG GATACAGCGC CTTGCACTGT GGGATTTTGA      4050

ACAATATTGT GGTGCTGTGC TGCAGTTACT GTGCTGATTT AAGTGAGATC      4100

AGGGTGCGCT GCTGTGCCCG GAGGACAAGG CGCCTTATGC TGCGGGCGGT      4150

GCGAATCATC GCTGAGGAGA CCACTGCCAT GTTGTATTCC TGCAGGACGG      4200

AGCGGCGGCG GCAGCAGTTT ATTCGCGCGC TGCTGCAGCA CCACCGCCCT      4250

ATCCTGATGC ACGATTATGA CTCTACCCCC ATGTAGGGAT CCCCATCACT      4300

AGTGCGGCCG CGGGGATCCA GACATGATAA GATACATTGA TGAGTTTGGA      4350

CAAACCACAA CTAGAATGCA GTGAAAAAAA TGCTTTATTT GTGAAATTTG      4400

TGATGCTATT GCTTTATTTG TAACCATTAT AAGCTGCAAT AAACAAGTTA      4450

ACAACAACAA TTGCATTCAT TTTATGTTTC AGGTTCAGGG GGAGGTGTGG      4500

GAGGTTTTTT CGGATCCTCT AGAGTCGACC TGCAGGCATG CAAGCTGTAG      4550

ATAAGTAGCA TGGCGGGTTA ATCATTAACT ACAAGGAACC CCTAGTGATG      4600

GAGTTGGCCA CTCCCTCTCT GCGCGCTCGC TCGCTCACTG AGGCCGGGCG      4650

ACCAAAGGTC GCCCGACGCC CGGGCTTTGC CCGGGCGGCC TCAGTGAGCG      4700

AGCGAGCGCG CAGCTGGCGT AATAGCGAAG AGGCCCGCAC CGATCGCCCT      4750

TCCCAACAGT TGCGCAGCCT GAATGGCGAA TGGAANTTCC AGACGATTGA      4800

GCGTCAAAAT GTAGGTATTT CCATGAGCGT TTTTCCTGTT GCAATGGCTG      4850

GCGGTAATAT TGTTCTGGAT ATTACCAGCA AGGCCGATAG TTTGAGTTCT      4900

TCTACTCAGG CAAGTGATGT TATTACTAAT CAAAGAAGTA TTGCGACAAC      4950

GGTTAATTTG CGTGATGGAC AGACTCTTTT ACTCGGTGGC CTCACTGATT      5000

ATAAAAACAC TTCTCAGGAT TCTGGCGTAC CGTTCCTGTC TAAAATCCCT      5050

TTAATCGGCC TCCTGTTTAG CTCCCGCTCT GATTCTAACG AGGAAAGCAC      5100

GTTATACGTG CTCGTCAAAG CAACCATAGT ACGCGCCCTG TAGCGGCGCA      5150

TTAAGCGCGG CGGGTGTGGT GGTTACGCGC AGCGTGACCG CTACACTTGC      5200

CAGCGCCCTA GCGCCCGCTC CTTTCGCTTT CTTCCCTTCC TTTCTCGCCA      5250

CGTTCGCCGG CTTTCCCCGT CAAGCTCTAA ATCGGGGGCT CCCTTTAGGG      5300

TTCCGATTTA GTGCTTTACG GCACCTCGAC CCCAAAAAAC TTGATTAGGG      5350
```

| | |
|---|---|
| TGATGGTTCA CGTAGTGGGC CATCGCCCTG ATAGACGGTT TTTCGCCCTT | 5400 |
| TGACGTTGGA GTCCACGTTC TTTAATAGTG GACTCTTGTT CCAAACTGGA | 5450 |
| ACAACACTCA ACCCTATCTC GGTCTATTCT TTTGATTTAT AAGGGATTTT | 5500 |
| GCCGATTTCG GCCTATTGGT TAAAAAATGA GCTGATTTAA CAAAAATTTA | 5550 |
| ACGCGAATTT TAACAAAATA TTAACGTTTA CAATTTAAAT ATTTGCTTAT | 5600 |
| ACAATCTTCC TGTTTTTGGG GCTTTTCTGA TTATCAACCG GGGTACATAT | 5650 |
| GATTGACATG CTAGTTTTAC GATTACCGTT CATCGATTCT CTTGTTTGCT | 5700 |
| CCAGACTCTC AGGCAATGAC CTGATAGCCT TTGTAGAGAC CTCTCAAAAA | 5750 |
| TAGCTACCCT CTCCGGCATG AATTTATCAG CTAGAACGGT TGAATATCAT | 5800 |
| ATTGATGGTG ATTTGACTGT CTCCGGCCTT TCTCACCCGT TTGAATCTTT | 5850 |
| ACCTACACAT TACTCAGGCA TTGCATTTAA AATATATGAG GGTTCTAAAA | 5900 |
| ATTTTTATCC TTGCGTTGAA ATAAAGGCTT CTCCCGCAAA AGTATTACAG | 5950 |
| GGTCATAATG TTTTTGGTAC AACCGATTTA GCTTTATGCT CTGAGGCTTT | 6000 |
| ATTGCTTAAT TTTGCTAATT CTTTGCCTTG CCTGTATGAT TTATTGGATG | 6050 |
| TTGGAANTTC CTGATGCGGT ATTTTCTCCT TACGCATCTG TGCGGTATTT | 6100 |
| CACACCGCAT ATGGTGCACT CTCAGTACAA TCTGCTCTGA TGCCGCATAG | 6150 |
| TTAAGCCAGC CCCGACACCC GCCAACACCC GCTGACGCGC CCTGACGGGC | 6200 |
| TTGTCTGCTC CCGGCATCCG CTTACAGACA AGCTGTGACC GTCTCCGGGA | 6250 |
| GCTGCATGTG TCAGAGGTTT TCACCGTCAT CACCGAAACG CGCGAGACGA | 6300 |
| AAGGGCCTCG TGATACGCCT ATTTTTATAG GTTAATGTCA TGATAATAAT | 6350 |
| GGTTTCTTAG ACGTCAGGTG GCACTTTTCG GGGAAATGTG CGCGGAACCC | 6400 |
| CTATTTGTTT ATTTTTCTAA ATACATTCAA ATATGTATCC GCTCATGAGA | 6450 |
| CAATAACCCT GATAAATGCT TCAATAATAT TGAAAAAGGA AGAGTATGAG | 6500 |
| TATTCAACAT TTCCGTGTCG CCCTTATTCC CTTTTTTGCG GCATTTTGCC | 6550 |
| TTCCTGTTTT TGCTCACCCA GAAACGCTGG TGAAAGTAAA AGATGCTGAA | 6600 |
| GATCAGTTGG GTGCACGAGT GGGTTACATC GAACTGGATC TCAACAGCGG | 6650 |
| TAAGATCCTT GAGAGTTTTC GCCCCGAAGA ACGTTTTCCA ATGATGAGCA | 6700 |
| CTTTTAAAGT TCTGCTATGT GGCGCGGTAT TATCCCGTAT TGACGCCGGG | 6750 |
| CAAGAGCAAC TCGGTCGCCG CATACACTAT TCTCAGAATG ACTTGGTTGA | 6800 |
| GTACTCACCA GTCACAGAAA AGCATCTTAC GGATGGCATG ACAGTAAGAG | 6850 |
| AATTATGCAG TGCTGCCATA ACCATGAGTG ATAACACTGC GGCCAACTTA | 6900 |
| CTTCTGACAA CGATCGGAGG ACCGAAGGAG CTAACCGCTT TTTTGCACAA | 6950 |
| CATGGGGGAT CATGTAACTC GCCTTGATCG TTGGGAACCG GAGCTGAATG | 7000 |
| AAGCCATACC AAACGACGAG CGTGACACCA CGATGCCTGT AGCAATGGCA | 7050 |
| ACAACGTTGC GCAAACTATT AACTGGCGAA CTACTTACTC TAGCTTCCCG | 7100 |
| GCAACAATTA ATAGACTGGA TGGAGGCGGA TAAAGTTGCA GGACCACTTC | 7150 |
| TGCGCTCGGC CCTTCCGGCT GGCTGGTTTA TTGCTGATAA ATCTGGAGCC | 7200 |
| GGTGAGCGTG GGTCTCGCGG TATCATTGCA GCACTGGGGC CAGATGGTAA | 7250 |
| GCCCTCCCGT ATCGTAGTTA TCTACACGAC GGGGAGTCAG GCAACTATGG | 7300 |
| ATGAACGAAA TAGACAGATC GCTGAGATAG GTGCCTCACT GATTAAGCAT | 7350 |

```
TGGTAACTGT CAGACCAAGT TTACTCATAT ATACTTTAGA TTGATTTAAA            7400

ACTTCATTTT TAATTTAAAA GGATCTAGGT GAAGATCCTT TTTGATAATC            7450

TCATGACCAA AATCCCTTAA CGTGAGTTTT CGTTCCACTG AGCGTCAGAC            7500

CCCGTAGAAA AGATCAAAGG ATCTTCTTGA GATCCTTTTT TTCTGCGCGT            7550

AATCTGCTGC TTGCAAACAA AAAAACCACC GCTACCAGCG GTGGTTTGTT            7600

TGCCGGATCA AGAGCTACCA ACTCTTTTTC CGAAGGTAAC TGGCTTCAGC            7650

AGAGCGCAGA TACCAAATAC TGTCCTTCTA GTGTAGCCGT AGTTAGGCCA            7700

CCACTTCAAG AACTCTGTAG CACCGCCTAC ATACCTCGCT CTGCTAATCC            7750

TGTTACCAGT GGCTGCTGCC AGTGGCGATA AGTCGTGTCT TACCGGGTTG            7800

GACTCAAGAC GATAGTTACC GGATAAGGCG CAGCGGTCGG GCTGAACGGG            7850

GGGTTCGTGC ACACAGCCCA GCTTGGAGCG AACGACCTAC ACCGAACTGA            7900

GATACCTACA GCGTGAGCTA TGAGAAAGCG CCACGCTTCC CGAAGGGAGA            7950

AAGGCGGACA GGTATCCGGT AAGCGGCAGG GTCGGAACAG GAGAGCGCAC            8000

GAGGGAGCTT CCAGGGGGAA ACGCCTGGTA TCTTTATAGT CCTGTCGGGT            8050

TTCGCCACCT CTGACTTGAG CGTCGATTTT TGTGATGCTC GTCAGGGGGG            8100

CGGAGCCTAT GGAAAAACGC CAGCAACGCG GCCTTTTTAC GGTTCCTGGC            8150

CTTTTGCTGG CCTTTTGCTC ACATGTTCTT TCCTGCGTTA TCCCCTGATT            8200

CTGTGGATAA CCGTATTACC GCCTTTGAGT GAGCTGATAC CGCTCGCCGC            8250

AGCCGAACGA CCGAGCGCAG CGAGTCAGTG AGCGAGGAAG CGGAAGAGC             8299
```

US 6,270,996 B1

RECOMBINANT ADENOVIRUS AND ADENO-ASSOCIATED VIRUS, CELL LINES AND METHODS OF PRODUCTION AND USE THEREOF

This application is a continuation of U.S. patent application Ser. No. 08/973,334, filed Dec. 5, 1997, which is a national phase filing, pursuant to 35 USC § 371, of PCT/US96/10245, filed Jun. 4, 1996, which is a continuation-in-part (CIP) of U.S. patent application Ser. No. 08/549,489, filed Oct. 27, 1995, and U.S. patent application Ser. No. 08/462,014, filed Jun. 5, 1995, now U.S. Pat. No. 5,756,283. U.S. patent application Ser. No. 08/549,489 is itself a CIP of U.S. patent application Ser. No. 08/462,014.

This invention was supported by the National Institute of Health Grant Nos. HD32649-01, DK47757 and DK49136. The United States government has rights in this invention.

FIELD OF THE INVENTION

The present invention relates generally to the field of somatic gene therapy, and specifically to methods and compositions useful in the treatment of genetic disorders.

BACKGROUND OF THE INVENTION

Adenoviruses are eukaryotic DNA viruses that can be modified to efficiently deliver a therapeutic or reporter transgene to a variety of cell types [see, e.g., M. S. Horwitz et al, "Adenoviridae and Their Replication", *Virology*, second edition, pp. 1712, ed. B. N. Fields et al, Raven Press Ltd., New York (1990)]. Recombinant adenovirus (rAds) are capable of providing extremely high levels of transgene delivery to virtually all cell types, regardless of the mitotic state. The efficacy of this system in delivering a therapeutic transgene in vivo that complements a genetic imbalance has been demonstrated in animal models of various disorders [K. F. Kozarsky et al, *Somatic Cell Mol. Genet.*, 19:449–458 (1993) ("Kozarsky et al I"); K. F. Kozarsky et al, *J. Biol. Chem.*, 269:13695–13702 (1994) ("Kozarsky et al II") and others]. The use of recombinant adenoviruses in the transduction of genes into hepatocytes in vivo has previously been demonstrated in rodents and rabbits [see, e.g., Kozarsky II, cited above, and S. Ishibashi et al, *J. Clin. Invest.*, 92:883–893 (1993)].

The first-generation recombinant, replication-deficient adenoviruses which have been developed for gene therapy contain deletions of the entire E1a and part of the E1b regions. This replication-defective virus is grown on an adenovirus-transformed, complementation human embryonic kidney cell line containing a functional adenovirus E1a gene which provides a transacting E1a protein, the 293 cell [ATCC CRL1573]. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection.

Adeno-associated virus (AAV) is an integrating human DNA parvovirus which has been proposed for use as a gene delivery vehicle for somatic gene therapy [B. J. Carter, in "Handbook of Parvoviruses", ed., P. Tijsser, CRC Press, pp.155–168 (1990)]. This small non-enveloped virus contains a 4.6 kb single stranded (ss) DNA genome that encodes sets of regulatory and capsid genes called rep and cap. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures.

Recombinant forms of AAV (rAAV) have been developed as vectors by replacing all viral open reading frames with a therapeutic minigene, while retaining the necessary cis elements contained in the ITRs. [See, e.g., U.S. Pat. Nos. 4,797,368; 5,153,414; 5,139,941; 5,252,479; and 5,354,678; and International Publication Nos. WO 91/18088 published Nov. 28, 1991; WO 93/24641 published Dec. 9, 1993 and WO94/13788 published Jun. 23, 1994]. However, progress towards establishing AAV as a transducing vehicle for gene therapy has been slow for a variety of reasons. For example, the integrated provirus preferentially targets specific sites in chromosome 19. Additionally, difficulties surround large-scale production of replication defective recombinants. The cells employed to produce rAAV must also be infected with adenovirus or herpesvirus to provide the necessary helper functions, thereby producing problems in purifying recombinant AAV (rAAV) from contaminating virus in culture. Practical experience with purified recombinant AAV as a gene therapy vector has been disappointing, because the more purified the AAV is from co-infection with its helper virus in culture, the lower the gene transduction efficiencies that the rAAV displays.

There remains a need in the art for additional recombinant adenoviruses and rAAV, therapeutic compositions and methods which enable effective use of these recombinant viruses in the treatment of disorders and diseases by gene therapy.

SUMMARY OF THE INVENTION

In one aspect of this invention, a packaging cell line is provided which expresses adenovirus genes E1a, E1b and E4, or functional fragments thereof, e.g., the E4 open reading frame (ORF) 6.

In another aspect, the invention provides a rAd comprising the DNA of at least a portion of the genome of an adenovirus having functional deletions of the E1 and E4 gene regions; a suitable gene operatively linked to regulatory sequences directing its expression, and an adenovirus capsid, the rAd capable of infecting a mammalian cell and expressing the gene product in the cell in vivo or in vitro. The invention also provides a mammalian cell infected with the rAd described above.

In still another aspect, the invention provides a rAd shuttle vector comprising the DNA of at least a portion of the genome of an adenovirus having functional deletions of the E1 and E4 gene regions.

In a further aspect, the invention provides a method for producing the above-described recombinant Ad and a method for delivering a selected gene into a mammalian cell using the recombinant Ad described above.

In another aspect, the invention provides a method for enhancing the efficiency of transduction of a recombinant AAV into a target cell. The method operates, in brief, by infecting a target cell with a ss recombinant adeno-associated virus (rAAV) which comprises a transgene operatively linked to regulatory sequences directing its expression, and contacting the infected cells with an agent which facilitates the conversion of ss rAAV to its double stranded (ds) form. Conversion of ss rAAV to ds rAAV occurs in the target cell, resulting in enhanced transduction of the rAAV into the target cell. The agent may be a helper virus which carries a selected gene or functional fragment thereof encoding a polypeptide capable of enhancing the conversion of the ss rAAV to ds rAAV and which is co-infected into the same target cell. The agent may also be a drug or chemical composition which accomplishes the same function and is applied to the infected target cell. This method can operate both in an ex vivo setting and in vivo.

In yet another aspect, the invention provides a novel recombinant AAV, which contains both the transgene intended for use in treating a genetic disease or disorder and at least one additional gene operatively linked to inducible or constitutive regulatory sequences. The additional gene(s) encodes a polypeptide capable of facilitating, alone or in concert with other additional genes, the conversion of ss rAAV to its ds form upon expression. In a preferred embodiment, the additional gene is adenovirus E4 or a functional fragment thereof. Also disclosed is a method for enhancing the efficiency of transduction of the novel rAAV into a target cell.

The novel rAAV and methods of this invention are also useful in pharmaceutical compositions for use in ex vivo and in vivo gene therapy treatment protocols for treating inherited diseases, cancer, and other genetic dysfunctions.

Other aspects and advantages of the present invention are described further in the following detailed description of the preferred embodiments thereof.

BRIEF DESCRIPTION OF THE DRAWINGS

FIG. 7A illustrates a model for leading strand synthesis of a complementary AAV strand in the presence of Rep (+Rep) or absence of Rep (–Rep). Rep expresses a terminal resolution activity that can convert a duplex structure with closed-ends to an open-ended duplex. In the absence of Rep, terminal resolution is impaired leaving the covalently closed, hairpin structures intact. Under these conditions, hairpins are expected to be found leftward and rightward, since both strands of a rescued ds AAV genome are packaged into virions.

FIG. 7B is a schematic of linear AV.CMVLacZ with labeled domains including the AAV ITRs, CMV immediate early enhancer/promoter (CMV), SV40 splice donor-splice acceptor (SD/SA), E. coli $\beta$-galactosidase cDNA (LacZ), and SV40 polyA signal (pA). Two NotI sites located at bp positions 1035 and 4509 are indicated.

FIG. 7C illustrates a closed end and an open end fragment of rAV.CMVLacZ.

FIGS. 7D, 7E and 7F indicate the mixture of open-ended and covalently closed duplex fragments generated by NotI digestion of ss AV.CMVLacZ at position 4509 in the absence of terminal resolution. The NotI 4509 digestion provides a convenient means of releasing a 361 bp fragment that contains the right ITR in the context of a hybridization target (i.e. SV40 pA). In the presence of terminal resolution, only the open-ended 361 bp fragment would be expected to be generated (FIG. 7D) by such digestion.

DETAILED DESCRIPTION OF THE INVENTION

Figure 1:
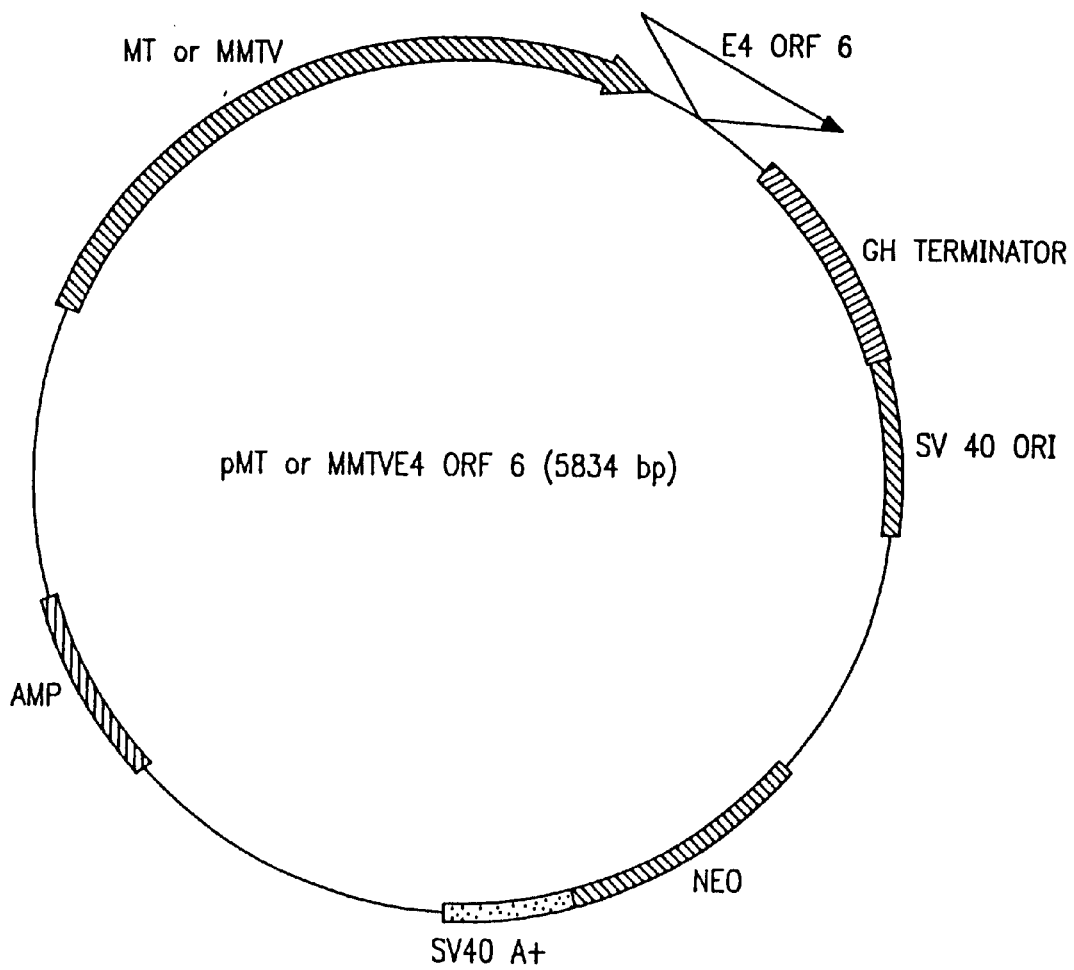
FIG. 1 is a schematic drawing of an exemplary plasmid pMMTVE4ORF6 [SEQ ID NO: 1] or pMTE4ORF6, which contains an MMTV or sheep MT promoter, respectively, in control of a human E4 ORF 6 gene sequence, a growth hormone gene terminator sequence (GH), and SV40 ori, pBR322-based plasmid sequences including a neo$^R$ gene, an SV40 polyA site and an amp$^R$ gene.

The present invention provides packaging cell lines, which enable the production of recombinant adenoviruses (rAd) functionally deleted in both the E1 and E4 genes. These rAd and methods which enable the therapeutic treatment of disorders with such rAds are disclosed. Novel "second generation" recombinant adeno-associated virus (rAAV) and methods for enhancing the transduction efficiency of rAAV containing a transgene for expression in a somatic gene therapy protocol are also provided. The methods and compositions of this invention are useful in ex vivo applications of gene therapy, such as in the transduction of bone marrow cells with desirable hematopoietic stem cell progenitor genes prior to bone marrow transplantation. The embodiments of the invention are also useful in pharmaceutical compositions for direct in vivo treatment of patients by gene therapy vectors, including the transduction of desirable genes in patients with genetic disorders, such as cystic fibrosis (CF).

I. Packaging Cell Lines

To increase the transgene capacity and decrease immune response to rAds, as many viral genes as possible should be deleted to inactivate the adenovirus. However, it is crucial to generate complementing cell lines for construction and propagation of such deleted Ad. The method and compositions of the present invention overcome several problems previously identified in the gene therapy for first generation E1 deleted adenoviruses and display advantages in administration particularly to muscle tissue.

Early region 4 (E4) of Ad serotype 5 consists of 7 ORFs believed to be involved in viral DNA replication, host cell shut-off, and late mRNA accumulation. To generate rAd deleted in E4, the function of the E4 region must be supplied to the rAd by a helper virus or packaging cell line. However, useful packaging cell lines have not been available previously because normally the continuous expression of functioning Ad E1 and functional E4 in a single cell line are toxic to the cell. Such cells are therefore not useful for the growth and replication of rAds. Further, the DNA encoding the functional Ad E1 and Ad E4 genes, when present in a packaging cell line, can increase the chances of recombination with a rAd virus to cause the virus to revert to a wildtype Ad virus.

The present invention avoids these problems by providing a packaging cell line which contains the Ad5 E1 gene and only the ORF 6 of the Ad5 E4 gene. ORF6 of E4 alone can provide the requirements for E4 in the viral life cycle.

According to this invention, the ORF6 is preferably under the transcriptional control of an inducible promoter. The mouse mammary tumor virus (MMTV) promoter, inducible by a glucocorticoid, particularly, dexamethasone, is presently preferred. The DNA sequence of the MMTV promoter spans nucleotides 1–1506 of SEQ ID NO: 1. Another inducible promoter is the sheep metallothionine (MT) promoter, inducible by zinc [M. G. Peterson et al, *Eur. J. Biochem.*, 174:417–424 (1988)]. However, the zinc sulfate inducer of the MT promoter can itself be toxic to the cells. Other inducible promoters, such as those identified in International patent application WO95/13392, published May 18, 1995, and incorporated by reference herein may also be used in the production of packaging cell lines according to this invention. Constitutive promoters, such as the constitutive Ad5 E4 region promoter, LTR, may be employed in control of the expression of ORF6.

The packaging cell line of the invention which utilizes an inducible promoter permits one to control the development of toxicity by regulating the expression of the E4 ORF6 gene. After the desired shuttle vector containing the Ad sequences is transfected into the cell line, expression of the E4 ORF6 can be induced by the appropriate inducer. The packaging cell is thus able to provide both Ad E1 and Ad E4 ORF6 gene products to the rAd for a sufficient period to allow productive infection and recovery of the rAd, before the cell becomes toxic. At present, the time period before the cell experiences toxicity is about 10 days.

In its most preferred form, the packaging cell line is a human embryonic kidney (HEK) 293 E1 expressing cell line into which is introduced the E4 ORF 6 sequence under the control of the inducible promoter. It should be understood by one of skill in the art that another parent cell line may be selected for the generation of a novel cell line expressing the E1a, E1b, and E4 ORF6 genes of a selected adenovirus serotype. Among such parent cell lines may be included HeLa [CCL 2], A549 [CCL 185], Kb [CCL 17], Detroit [e.g., Detroit 510, CCL 72] and WI-38 [ATCC CCL 75] cells. These cell lines are all available from the American Type Culture Collection, 12301 Parklawn Drive, Rockville, Md., USA. Other suitable parent cell lines may be obtained from other sources. If such parent cell lines were selected for modification, the cell line would need to be further supplied with the E1a and E1b gene functions, e.g., such as by transfection with a plasmid containing these genes or functional fragments thereof under a suitable promoter, as well as with the ORF6 gene as described herein.

Example 1 teaches construction of packaging cell lines containing only the ORF 6 of Ad5 E4 region or, for functional comparisons, the entire E4 region. Briefly described, the entire E4 region and an ORF6 sequence of Ad 5 E4 gene were obtained by known techniques [see, e.g., Sambrook et al., "Molecular Cloning. A Laboratory Manual.", 2d edit., Cold Spring Harbor Laboratory, New York (1989) and references cited therein]. To isolate the ORF6 region, the anchored PCR technique was used to amplify the ORF6 sequence from its initiation codon to its termination codon. Primers selected from the published sequence of ORF6 were used to amplify the ORF sequence and insert restriction sites onto the end of the sequence. The E4 ORF6 sequence itself is reproduced as nucleotides 1523 through 2408 of SEQ ID NO: 1. The entire E4 gene sequence is published in the Genbank sequence of Ad5 [Genbank Accession No. M73260].

A minigene was constructed that placed the ORF6 sequence under the control of a selected promoter. By "minigene" as used here is meant the combination of the desired sequence to be expressed (in this particular instance, the ORF6 sequence) and the other regulatory elements necessary to transcribe the desired sequence and express the gene product in a cell containing that minigene. The ORF6 sequence gene is operatively linked to regulatory components in a manner which permits its transcription. Such components include conventional regulatory elements, such as a promoter to drive ORF6 expression. One inducible promoter was the $Zn^{+2}$ inducible MT promoter; the other was the dexamethasone-inducible MMTV promoter of SEQ ID NO: 1.

The minigene also contains nucleic acid sequences heterologous to the ORF6 viral sequence, including sequences providing signals required for efficient polyadenylation of the transcript (poly-A or pA). A common poly-A sequence which is employed in this invention is that derived from the growth hormone (GH) gene terminator sequence (nuc. 2409–3654 of SEQ ID NO: 1). The poly-A sequence generally is inserted in the minigene following the ORF6 sequence. The polyA sequence employed in the MMTV-ORF6 minigene described in Example 1 [SEQ ID NO: 1] is supplied by the GH gene terminator and an SV40 origin of replication (ori). A similar minigene differing in promoter sequence, polyA sequence and/or SV40 ori can also be designed by one of skill in the art to transfer the E4 ORF6 sequence to a shuttle plasmid. Selection of these and other common vector elements are conventional [see, e.g., Sambrook et al, cited above, and references cited therein] and many such sequences are available from commercial and industrial sources as well as from Genbank.

The ORF6-containing minigene was subcloned into a pBR322-based shuttle plasmid that contained a neomycin resistance gene, resulting in the shuttle vector of FIG. 1. Any of the many known bacterial shuttle vectors may be employed to carry the minigene, providing that the vector contains a reporter gene or selectable marker of which many, e.g., neo, amp or puromycin, are known in the art. It is expected that one of skill in the art can develop other suitable shuttle vectors using other plasmid components which are similarly capable of transferring the ORF6 minigene into the chromosome of a cell transfected with the plasmid.

As further described in Example 1, other shuttle vectors were designed for comparative purposes, which contain the complete or substantially complete Ad5 E4 region under the control of the constitutive retroviral MLV LTR sequence in the presence or absence of the endogenous E4 promoter. The shuttle plasmid carrying the ORF6 minigene (or the entire E4 region) was introduced into HEK 293 cells which express the Ad E1 gene products. Complementing cell lines were generated that express these Ad E4 or ORF6 genes from either their endogenous promoters or heterologous inducible promoters. These cell lines are further characterized by their genetic constitution, E4 protein synthesis, recombinant AAV helper function, relative plaque efficiency of H5dl1004 virus, and growth kinetics of recombinant E1/E4 deleted adenovirus. These characteristics of exemplary E1/E4 expressing packaging cell lines are discussed in detail in the following examples.

II. Recombinant Adenovirus

The E1/E4 expressing cell line is useful in constructing E1/E4 deleted rAds which can deliver a suitable gene to mammalian cells and tissues. These rAds are functionally deleted in at least the E1a, E1b and E4 Ad gene regions. By the term "functionally deleted" is meant that a sufficient amount of the gene region is removed or otherwise damaged, e.g., by mutation or modification, so that the gene region is no longer capable of producing the products of gene expression. If desired, the entire gene region may be removed. In in vivo experiments with the rAd grown in the packaging cell lines, the E1/E4 deleted rAd demonstrated utility particularly in transferring a transgene to a muscle cell.

The adenovirus sequences used in the construction of the shuttle vectors, helper viruses, if needed, and rAd, and other components and sequences employed in the construction of the vectors and viruses described herein may be readily obtained from commercial or academic sources based on previously published and described sequences. Viral materials may also be obtained from an individual patient. The viral sequences and vector components may be generated by resort to the teachings and references contained herein, coupled with standard recombinant molecular cloning techniques known and practiced by those skilled in the art. Modifications of existing nucleic acid sequences forming the vectors, including sequence deletions, insertions, and other mutations taught by this specification may be generated using standard techniques. Similarly, the methods employed for the selection of viral sequences useful in a vector, the cloning and construction of the "minigene" and its insertion into a desired viral shuttle vector and the production of a recombinant infectious virus are within the skill in the art given the teachings provided herein.

A. Construction of the Transgene

A "minigene" in this context is defined as above, except that the components of this minigene are designed to express the gene product ex vivo or in vivo. Such components include conventional regulatory elements necessary to drive expression of the transgene in a cell transfected with the rAd. For this minigene, a selected promoter is operatively linked to the transgene and located, with other regulatory elements, within the selected viral sequences of the recombinant vector. Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytomegalovirus (CMV) immediate early promoter/enhancer [see, e.g., Boshart et al, *Cell*, 41:521–530 (1985)]. Another desirable promoter includes the Rous sarcoma virus LTR promoter/enhancer. Still another promoter/enhancer sequence is the chicken cytoplasmic β-actin (CB) promoter [T. A. Kost et al, *Nucl. Acids Res.*, 11(23):8287 (1983)]. Other suitable promoters may be selected by one of skill in the art.

The minigene may also desirably contain nucleic acid sequences heterologous to the viral vector sequences including poly-A sequences and introns with functional splice donor and acceptor sites, as described above. The poly-A sequence generally is inserted in the minigene following the transgene sequences and before the 3' adenovirus sequences. A minigene of the present invention may also contain an intron, desirably located between the promoter/enhancer sequence and the transgene. Selection of these and other common vector elements are conventional as described above and many such sequences are available from commercial and industrial sources as well as from Genbank.

As above stated, the minigene is located in the site of any selected deletion in the rAd. In the E1/E4 deleted rAd H5.001CBLacZ, the transgene is located in the deleted E1 gene region. However, the transgene may be located elsewhere in the adenovirus sequence, as desired.

B. Production of Recombinant Adenovirus

Adenovirus sequences useful in this invention may include the DNA sequences of a number of adenovirus types, which are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified 41 human types [see, e.g., Horwitz, cited above]. Similarly adenoviruses known the infect other animals may also be employed in the vector constructs of this invention. The selection of the adenovirus type is not anticipated to limit the following invention. A variety of adenovirus strains are available from the American Type Culture Collection, Rockville, Md., or available by request from a variety of commercial and institutional sources. In the following exemplary embodiment an adenovirus, type 5 (Ad5) is used for convenience.

However, it is desirable to obtain a variety of adenovirus shuttle vectors based on different human adenovirus serotypes. It is anticipated that a library of such plasmids and the resulting rAds would be useful in a therapeutic regimen to evade cellular, and possibly humoral, immunity, and lengthen the duration of transgene expression, as well as improve the success of repeat therapeutic treatments. Additionally the use of various serotypes is believed to produce rAds with different tissue targeting specificities. Additionally, the absence of adenoviral genes E1 and E4 in the rAd of this invention should reduce or eliminate adverse CTL responses which normally cause destruction of rAds deleted of only the E1 gene.

rAds of this invention are recombinant, defective adenoviruses (i.e., E1 deleted) which are also deleted completely or functionally of the E4 gene region. Functional deletions of E4 gene regions may be assessed by assays of Examples 2 and 3, among other assays. rAds useful in this invention may optionally bear other mutations, e.g., temperature sensitive (ts) mutations in the E2a gene region, and deletions in the E3 gene regions.

An adenovirus of this invention contains a functional deletion of the adenoviral early immediate early gene E1a (which spans mu 1.3 to 4.5) and delayed early gene E1b (which spans mu 4.6 to 11.2). Similarly the adenovirus has a functional deletion of the whole E4 region (which spans mu 92 to 97.2), or of at least ORF6 of the E4 region. Gene regions which may be optionally deleted in the E1/E4 deleted rAd of this invention include all or a portion of the adenovirus delayed early gene E3 (which spans mu 76.6 to 86.2). The function of E3 is irrelevant to the function and production of the rAd.

The rAd of this invention may also have a mutation which results in reduced expression of adenoviral protein and/or reduced viral replication. For example, a ts mutation may be introduced into the adenovirus delayed early gene E2a (which spans mu 67.9 to 61.5). Among such mutations include the incorporation of the missense ts mutation in the (DBP)E2a region found in the Ad5 H5ts125 strain [P. Vander Vliet et al, *J. Virol.*, 15:348–354 (1975)] at 62.5 mu. A single amino acid substitution (62.5 mu) at the carboxy end of the 72 kd protein produced from the E2a gene in this strain produces a protein product which is a ss DNA binding protein and is involved in the replication of adenoviral genomic DNA. At permissive temperatures (approximately 32° C.) the ts strain is capable of full life cycle growth on HeLa cells, while at non-permissive temperatures (approximately 38° C.) no replication of adenoviral DNA is seen. In addition, at non-permissive temperatures, decreased immunoreactive 72 kd protein is seen in HeLa cells. See, e.g., J. F. Engelhardt et al, *Hum. Gene Ther.*, 5:1217–1229 (1994); J. F. Engelhardt et al, *Proc. Natl. Acad. Sci., USA*, 91:6196–6200 (1994) and International patent application WO95/13392, published May 18, 1995, incorporated by reference herein.

However, it should be understood that other deletions in the adenovirus genome as previously described in the art or otherwise may also occur in the rAds of this invention. One minimal type of rAd can contain adenovirus genomic sequences from which all viral genes are deleted. More specifically, the adenovirus sequences may be only the cis-acting 5' and 3' inverted terminal repeat (ITR) sequences of an adenovirus (which function as oris) and the native 5' packaging/enhancer domain, that contains sequences necessary for packaging linear Ad genomes and enhancer elements for the E1 promoter. The adenovirus 5' sequence containing the 5' ITR and packaging/enhancer region (Ad5 mu 0–1 or bp 1–360) can be employed as the 5' adenovirus sequence in rAd of this invention. The 3' adenovirus sequences including the right terminal (3') ITR sequence of the adenoviral genome spanning about bp 35,353—end of the adenovirus genome, or map units ~98.4–100 may be desirably employed as the 3' sequence of the rAd. These sequences, which are clearly devoid of the E1 and E4 genes, can flank, or be operatively associated with the minigene in a rAd. Any other necessary Ad gene products will then be supplied by helper viruses and the E1/E4 ORF6 expressing packaging cell of this invention.

Exemplary rAds for use in this invention, for example, may be obtained by homologous recombination of desired fragments from various rAds, a technique which has been commonly employed to generate other rAds for gene therapy use. In the examples below, a representative rAd, H5.001CBLacZ, is constructed by homologous recombination between the adenovirus dl1004 (also H5dl1004) viral backbone and pAdCBLacZ minigene DNA. H5dl1004 is an Ad5 virus deleted of from about map unit 92.1 through map unit 98, i.e., substantially the entire E4 gene. The dl1004 virus is described in Bridge and Ketner, *J. Virol.*, 632(2): 631–638 (February 1989).

the pAdCBLacZ vector is a cDNA plasmid containing Ad m.u. 0–1, an E1 deletion into which is inserted a bacterial β-galactosidase gene under the control of a chicken β-actin promoter, with other regulatory elements as described below, and flanked by Ad m.u. 9–16 and plasmid sequence.

The production of the E1/E4 rAd of this invention in the packaging cell line of this invention utilizes conventional techniques. Such techniques include conventional cloning techniques of cDNA such as those described in texts [Sambrook et al, cited above], use of overlapping oligonucleotide sequences of the adenovirus genomes, PCR and any suitable method which provides the desired nucleotide sequence. Standard transfection and co-transfection techniques are employed, e.g., $CaPO_4$ transfection techniques using the complementation 293 cell line. Other conventional methods employed include homologous recombination of the viral genomes, plaquing of viruses in agar overlay, methods of measuring signal generation, and the like.

For example, following the construction and assembly of the desired minigene-containing plasmid vector pAdCBLacZ, the E1/E4 expressing packaging cell line of this invention is infected with the helper virus H5dl1004. The infected cell line is then subsequently transfected with an adenovirus plasmid vector by conventional methods. Homologous recombination occurs between the E4-deleted H5dl1004 helper and the pAdCBLacZ vector, which permits the adenovirus-transgene sequences in the vector to be replicated and packaged into virion capsids, resulting in the rAd. About 30 or more hours post-transfection, the cells are harvested, an extract prepared and the rAd containing the LacZ transgene is purified by buoyant density ultracentrifugation in a CsCl gradient.

III. Use of the Recombinant Virus in Gene Therapy

The rAd containing the transgene produced by cooperation of the adenovirus vector and E4 deleted helper virus and packaging cell line, as described above, provides an efficient gene transfer vehicle which can deliver the transgene in a pharmaceutical composition to a patient in vivo or ex vivo and provide for integration of the gene into a mammalian cell.

The rAds are administered to humans in a conventional manner for gene therapy and serve as an alternative or supplemental gene therapy for the disorder to which the transgene is directed. A rAd of this invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAds are administered in sufficient amounts to transfect the desired target cells, e.g., muscle, liver, epithelial, etc. and provide sufficient levels of transfer and expression of the transgene to provide a therapeutic benefit without undue adverse or with medically acceptable physiological effects which can be determined by those skilled in the medical arts. Conventional and pharmaceutically acceptable routes of administration include direct delivery to the muscle or other selected cell, intranasal, intravenous, intramuscular, subcutaneous, intradermal, oral and other parental routes of administration. Routes of administration may be combined, if desired.

Dosages of rAd will depend primarily on factors such as the condition being treated, the age, weight and health of the patient, and may thus vary among patients. For example, a therapeutically effective human dose of the rAd is generally in the range of from about 20 to about 100 ml of saline solution containing concentrations of from about $1 \times 10^9$ to $1 \times 10^{11}$ pfu/ml virus. A preferred human dose is estimated to be about 50 ml saline solution at $2 \times 10^{10}$ pfu/ml. The dose will be adjusted to balance the therapeutic benefit against any side effects. The levels of expression of the transgene can be monitored to determine the frequency of administration.

An optional method step involves the co-administration to the patient, either concurrently with, or before or after administration of the rAd of a suitable amount of a short acting immune modulator. The selected immune modulator is defined herein as an agent capable of inhibiting the formation of neutralizing antibodies directed against the recombinant vector of this invention or capable of inhibiting or substantially delaying cytolytic T lymphocyte (CTL) elimination of the vector. Among desirable immune modulators are interleukin-12 [European Patent Application No. 441,900]; gamma interferon [S. C. Morris et al, *J. Immunol.*, 152:1047 (1994)]; interleukin-4 [U.S. Pat. No. 5,017,691]; antibody to the CD4 protein, such as anti-OKT 3+ [see, e.g., U.S. Pat. No. 4,658,019] or antibody GK1.5 (ATCC Accession No. TIB207); a soluble CD40 molecule or an antibody to CD40 ligand (Bristol-Myers Squibb Co) [European patent application 555,880, published Aug. 18, 1993]; a soluble form of B7 or an antibody to CD28 or CTLA4 [CTLA4-Ig (Bristol-Myers Squibb Co), European patent application 606,217, published Jul. 20, 1994], or agents such as cyclosporin A or cyclophosphamide. Thus, the pharmaceutical compositions and methods of this invention provide a desirable gene therapy treatment.

IV. Recombinant Adeno-Associated Virus

In the following context the term "transgene" means a nucleic acid sequence or reverse transcript thereof, heterologous to the AAV sequence, which encodes a polypeptide or protein of interest. The transgene may be operatively linked to regulatory components in a manner which permits transgene transcription, i.e., the transgene is placed into operative association with a promoter, as well as other regulatory sequences, such as SV40 introns or polyA sequences, useful for its regulation. The composite association of the transgene with its regulatory sequences is referred to herein as a minicassette or minigene.

The composition of the transgene or minicassette sequence will depend upon the use of which the resulting rAAV will be put. For example, one type of transgene sequence includes a reporter sequence, which upon expression produces a detectable signal. Such reporter sequences include without limitation, an *E. coli* β-galactosidase (LacZ) cDNA, an alkaline phosphatase gene (ALP) and a green fluorescent protein gene. These sequences, when associated with regulatory elements which drive their expression, provide signals detectable by conventional means, e.g., ultraviolet wavelength absorbance, visible color change, etc.

Another type of transgene sequence includes a therapeutic gene which expresses a desired gene product in a host cell. These therapeutic nucleic acid sequences typically encode products for administration and expression in a patient in vivo or ex vivo to replace or correct an inherited or non-inherited genetic defect or treat an epigenetic disorder or disease. Such transgenes may be readily selected by one of skill in this art and the design of the transgene or the minicassette for insertion into the rAAV is not a limitation of this invention.

The term "rAAV" encompasses any recombinant AAV gene therapy vehicle of the prior art, including the AdAAV hybrid virus described in published International Patent Application No. WO96/13598, published May 9, 1996. More specifically, rAAV defines a rAAV comprising: (a) the DNA of at least a portion of the genome of an AAV, which portion is capable of transducing into a target cell at least one selected gene in the absence of cell division; and (b) at least one selected gene (or transgene) operatively linked to regulatory sequences directing its expression, the gene flanked by the DNA of (a) and capable of expression in the target cell in vivo or in vitro.

Other rAAVs have been described in the art. The method of this invention is not limited by the precise nature of the AAV sequences used in the rAAV, provided that at a minimum both the 5' and 3' AAV inverted terminal repeats are present. Thus, the rAAV may be selected by one of skill in the art, and is not itself a limitation on this invention. The rAAVs specifically disclosed herein are illustrative.

By the term "transduction" is meant that the rAAV produced by practice of the invention is capable of infecting a desired target cell and expressing the transgene in the cell by harnessing the cell's machinery. Transduction may include stably integrating the viral DNA into a chromosome of the target cell. "Enhanced transduction" is defined as the ability of the rAAV in the presence of a conversion agent to transduce the target cell, either in vitro, ex vivo or in vivo, at an efficiency greater than a typical prior art rAAV produced in, and purified from, a culture co-infected with an adenovirus or herpesvirus helper.

This method is based on the observation that the limiting step in rAAV mediated transduction of cells for gene therapy is not the internalization or transfer of the ss viral genome, but rather the subsequent conversion of the single-stranded (ss) viral genome to a transcriptionally active double-stranded (ds) form. Formation, of ds DNA intermediates is necessary for recombinant gene expression, which is likely to be modulated by viral and cellular factors through post-transcriptional mechanisms. The inventors have designed a method to overcome this rate-limiting step, thereby enhancing transduction ability of an rAAV and ultimately the use of rAAV in gene therapy protocols.

This method of the present invention may employ a conventionally prepared ss rAAV containing a transgene. The prior art produces ss rAAV by co-infection in culture with a helper adenovirus or herpesvirus, followed by purifying the rAAV from the culture contaminants including the helper virus, and infecting the target cell with the rAAV alone. The present invention provides for infecting a target cell with a ss rAAV. However, once the target cell is infected, the infected cell is contacted with an agent which facilitates the conversion of the ss rAAV to the ds form of rAAV. The action of this "facilitating agent" or "conversion agent" causes the ss to ds conversion to occur in the target cell, resulting in enhanced transduction of the recombinant AAV into the target cell. By facilitating the conversion of ss to ds rAAV in the target cell, the method of this invention may also result in both transduction and stable chromosomal integration of the rAAV into the chromosome of said host cell.

Preferably, for use of this invention the "facilitating or conversion agent" may take several forms.

A. The Conversion Agent is a Helper Virus

In one embodiment, the agent is a helper virus and the method includes an additional step of co-infecting the target cell with the helper virus. The helper virus useful in this method contains a selected gene which can facilitate the conversion of ss rAAV to ds rAAV. The selected gene may encode a gene product or polypeptide (or a functional fragment of the polypeptide which shares the biological activity of the full-length polypeptide) which enhances the conversion. Alternatively, the selected gene may express an antisense or ribozyme which functions in the cell to block or inhibit a cellular gene that normally prevents ss to ds conversion of the rAAV. These genes may also be employed in the second generation rAAV described below.

The helper virus is capable of expressing the selected gene product in the target cell in the absence of cell division. The helper virus may be a wild-type or mutant adenovirus. The helper virus may alternatively by a wild-type or mutant herpesvirus. Preferably, for use as facilitating agents, such viruses are mutants deleted of several normal genes so that the helper viruses and/or their expressed gene products will not cause disease in a patient.

For example, a helper adenovirus useful in this invention may express only a gene product of a single adenoviral early gene. Exposure of the ss rAAV to an Ad early gene product is sufficient to substantially enhance the formation of ds rAAV genome with a coordinate increase in transduction efficiency. The Ad early genes which are useful in producing this effect are E1, E2a, E4 and functional fragments thereof. However, as demonstrated by the examples below, adenovirus substantially enhances recombinant AAV transduction in vitro in a way that is dependent on expression of the E1 and E4 genes of adenovirus and is directly proportional to the appearance of ds replicative forms of rAAV.

One example of a helper virus is an adenovirus deleted of most of its wild-type early genes and which is capable of expressing only its E4 gene or a functional fragment thereof in the target cell. Among such functional fragments is the ORF 6 of the E4 gene. As described below in the examples, experiments in cell lines indicate that the ORF6 of the adenoviral E4 gene locus is sufficient to significantly enhance rAAV transduction. Selective expression of the E4-ORF6 product of adenovirus accomplishes an increase in transduction efficiency similar to, but somewhat attenuated, compared to that produced by exposure to the E1 and E4 gene products in combination. That is, the ORF6 product of E4 is sufficient to enhance the augmentation of rAAV transduction; but this effect is amplified substantially by E1 gene products.

Thus, more preferably, exposure of the rAAV to both the expressed E1 and E4 gene products produces a substantial enhancement of the above-described rate limiting step. Therefore, another exemplary helper virus may also contain more than one gene which, upon expression, facilitates the ss to ds conversion. An example of such a helper virus is an adenovirus which expresses both the E1 and E4 genes, or functional fragments thereof. Still other Ad genes may be expressed by the helper virus, provided that the virus is sufficiently crippled so that it does no cause disease in the patient contributing the target cells.

Where the agent which facilitates conversion of ss to ds rAAV is a helper virus, the method of the invention comprises co-infecting the target cell with the rAAV and the helper virus. Such co-infection may occur in the context of ex vivo therapy, i.e., manipulations performed on cells extracted from the patient, which cells are reinserted into the patient after the method is performed. Alternatively, the patient may be directly co-infected with the two viruses by conventional means. Delivery of the two viruses to the patient may be directed to a specific organ, or to the general circulatory system. Such delivery methods are described in the art for gene therapy of e.g., cystic fibrosis [see, e.g., U.S. Pat. No. 5,240,846].

B. The Conversion Agent is a Chemical, Drug or Other Entity that can Activate rAAV Transduction In another embodiment of the method of this invention, the conversion agent which contacts the cells infected with the rAAV may be selected from the following classes of known compounds or methods: 1) inhibitors of DNA synthesis such as hydroxyurea, hydrogen peroxide, and other direct or indirect inhibitors of DNA polymerase; 2) chemotherapeutic agents that induce DNA damage, such as cyclophosphamide, alkylating agents, purine analogs, e.g., 6-thioguanine, etc.; 3) drugs that interfere with DNA modifying enzymes, such as inhibitors of topoisomerase, DNA ligase exonucleases and endonucleases; and 4) agents that nonspecifically enhance transcription, such as sodium butyrate, or agents that stabilize cells, such as DMSO. Also, genotoxic agents such as carcinogens may be employed as the conversion agent. Other methods of inducing disruption or damage to DNA may also be useful as agents capable of facilitating ss to ds conversion of rAAV and maybe selected by one of skill in the art, including physical methods, such as irradiation. These classes of compounds or methods are believed to result in the conversion from ss to ds rAAV.

According to this embodiment of the method of the invention, the rAAV is again produced conventionally, but not co-infected with a helper virus. The ss rAAV is infected into the target cell, and the infected cell is contacted by the agent in an appropriate manner depending on the identity of the agent. These conversion enhancing agents can be employed in ex vivo treatment of the target cells infected by the rAAV by application directly to the cells. Such application can occur substantially simultaneously, or consecutively, with application of the rAAV gene therapy vehicle. For example, the infected target cell may be subjected to one of the above-listed compounds or drugs for a desired time period. The parameters for contacting the infected cells with the agent may readily be determined by one of skill in the art. These parameters will depend upon whether the method is performed ex vivo or in vivo. For example, the number of ex vivo infected cells to be treated will be considered for the dosage, and timing of such treatment.

Similarly, the physical status of the patient can determine the parameters of delivery of the agent to the patient in vivo. The dosage and amount of the damaging agent may therefore be adjusted by one of skill in the art. Where the agents are typical chemotherapeutic drugs approved for use in humans or animals, such enhanced conversion of rAAV may also occur in vivo by the co-administration of the agent, i.e., the chemotherapeutic drug, and the rAAV gene therapy vehicle to the patient. According to this aspect of the invention, the chemotherapeutic drug would be administered only when the rAAV is administered. Appropriate dosages and amounts of chemotherapeutic drugs and recombinant gene therapy vehicles and means for determining such amounts are within the skill of the art. However, because the effect of the chemotherapeutic drug will enhance the ss to ds conversion of the rAAV and thus enhance its efficiency of transduction into the target cells, it is anticipated that lower dosages than the conventional dosages of either or both the drug and the rAAV could be effectively administered.

C. Conversion Agent May be Part of the rAAV.

In still another embodiment of this invention, a novel "second generation" rAAV may be designed to incorporate the conversion agent into the virus, so that both the transgene and the conversion agent are co-expressed in the target cell. Such a novel recombinant adeno-associated virus comprises the following components:

(a) the DNA of at least a portion of the genome of an adeno-associated virus which portion is capable of transducing at least two selected genes or functional fragments thereof into a target cell in the absence of cell division; (b) a first selected gene, i.e., the desired transgene, operatively linked to regulatory sequences directing its expression, and (c) a second selected gene, i.e., the "conversion gene" operatively linked to regulatory sequences capable of directing expression of said second gene. The "conversion gene" upon expression is capable of facilitating the conversion of the ss rAAV to its ds form upon expression. The first and second genes in this rAAV are flanked by the AAV DNA, preferably the 5' and 3' ITRs. An embodiment of such a second generation rAAV is provided schematically in FIG. 11. Its DNA sequence is provided in SEQ ID NO: 5.

Another embodiment of such a novel rAAV may include more than one gene which upon expression has the ability to facilitate conversion of ss to ds rAAV in the target cell. For example, the novel rAAV described above may also contain an additional selected gene operatively linked to regulatory sequences capable of directing its expression, the additional gene and said second "conversion" gene described above being capable of jointly facilitating the conversion of ss rAAV to its ds form upon expression of both the second and additional genes. In this rAAV, all three genes, i.e., the transgene, the second "conversion" gene and the additional gene are flanked by the AAV DNA.

In one desirable embodiment of a novel rAAV, the AAV ITRs flank a selected transgene, and a conversion gene, which is the adenovirus E4 gene or a functional fragment thereof (e.g., the ORF6 sequence). In another embodiment, the novel recombinant expresses three genes, the transgene, the adenovirus E4 gene or a functional fragment thereof and the adenovirus E1 gene or a functional fragment thereof. The E4 and E1 gene products expressed in the target cell with the transgene, together act to facilitate conversion of the ss to ds form of rAAV.

In still another embodiment of the novel rAAV and its use, the regulatory sequences directing expression of the conversion gene, e.g., whether it be a single second gene or more than a single additional gene, may include an inducible promoter. Thus, expression of the conversion gene occurs only in the presence of an inducing agent. Many inducible promoters and companion inducing agents, e.g., steroids such as glucocorticoids, are known to the art and may be readily selected for incorporation into the rAAV and methods of this invention by one of skill in the art with resort to this description.

The method of the invention employing such "second generation" rAAVs which carry at least one "conversion gene" provides for infecting the target cell with this ss rAAV. Where the promoters directing expression of both the transgene and the conversion gene are constitutive, the infected target cell machinery will direct the expression of the transgene product and conversion gene product. Co-expression in the target cell of the transgene and the "conversion gene" facilitates the conversion of ss rAAV to ds rAAV in the cell, and increases the transduction efficiency, and perhaps stable chromosomal integration, without further method steps.

When the second generation rAAV employed in the method contains the "conversion gene(s)" under the control of inducible promoter(s), the method is slightly altered. Following infection of the target cell by the rAAV, the infected target cell is contacted with a suitable inducing agent, which triggers the inducible promoter to "turn on" production of the conversion gene product. When the inducing agent is removed or stopped, the expression of the conversion gene product is "turned off".

As described above, any prior art rAAV containing a transgene for gene therapy may be used in at least one embodiment of the above methods. The sources, selection and assembly of the various components to generate the rAAV, including the novel rAAV described above, are now conventional and readily accessible to one of skill in thisart, given the disclosure contained herein. Such methods employ conventional genetic engineering techniques [See, e.g. Sambrook et al, cited above].

The novel rAAV viruses and the methods of this invention provide efficient gene transfer vehicles for somatic gene therapy and are suitable in pharmaceutical compositions for ex vivo applications and in vivo use. When rAAV contain a therapeutic gene, e.g., in place of the LacZ transgene illustrated in the exemplary rAAV, AV.CMVLacZ, by use of the rAAV and the methods described herein, the therapeutic transgene can be delivered to a patient in vivo or ex vivo to provide for efficient transduction, and possibly stable integration, of the desired gene into the target cell. Thus, these novel rAAV and the methods described herein can be employed to correct genetic deficiencies or defects. The potential of AAV to efficiently integrate its genome into nondividing cells is currently being exploited in the development of gene therapies based on ex vivo transduction of hematopoietic stem cells. In vivo application of rAAVs is primarily being developed for the treatment of CF where purified stocks of virus are instilled into the airway to transduce the terminally differentiated epithelial cells of conducting airway. The methods and compositions described herein can be used with both types of gene therapy. Another condition suitable for such use includes transduction of the low density lipoprotein (LDL) receptor gene into hepatocytes for the treatment of familial hypercholesterolemia. One of skill in the art can generate any number of rAAV which can be used via the above methods for the treatment of these and other disorders.

For ex vivo or for in vivo therapy, the rAAV may be used to infect the target cells by suspending the virus particles in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAAV are administered in sufficient amounts to transfect the desired cells and provide sufficient levels of expression of the selected transgene to provide a therapeutic benefit without undue adverse, or with medically acceptable, physiological effects which can be determined by those skilled in the medical arts. Conventional and pharmaceutically acceptable routes of in vivo administration include direct delivery to the target organ, tissue or site, intranasal, intravenous, intramuscular, subcutaneous, intradermal, oral and other parental routes of administration. Routes of administration may be combined, if desired.

Dosages of the rAAV for the infecting step of the method will depend primarily on factors such as the therapeutic environment, i.e., ex vivo or in vivo; the condition being treated, the selected gene, the age, weight and health of the patient, and may thus vary among patients. A therapeutically effective dosage of the rAAV for ex vivo treatment will be based upon the multiplicity of infection, which is likely to range from between about 1 to about 10 transducing particles/cell. A therapeutically effective human dosage of the rAAV for in vivo infection according to the present invention is believed to be in the range of from about 20 to about 50 ml of saline solution containing concentrations of from about $1 \times 10^7$ to $1 \times 10^{10}$ transducing viral particles/ml virus. A preferred human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

The effective amount of the facilitating agent to be administered is within the skill of the art to determine and will depend upon the identity of the agent. Known dosages of certain of the classes of chemicals and pharmaceuticals described above may be employed in this method to damage the DNA and facilitate ss to ds conversion of the rAAV. Where the agent is a gene expressed by a helper virus, the amounts of infecting virus should be similar to those amounts described above for the rAAV. Of course, where the agent is a gene present in a second generation rAAV, the identical dosages described above for the rAAV will apply.

Several embodiments of the above-described methods of this invention were confirmed in murine models or rAAV mediated gene transfer to both lung and liver. These experiments demonstrated similarly low levels of gene transfer in vivo by rAAV, which was increased several orders of magnitude by coinfection with E1 and E4 expressing adenovirus.

In summary, experiments were conducted to demonstrate that adenovirus enhances rAAV transduction in cultured cells. During the production and characterization of a lacZ recombinant AAV generated in 293 cells that were coinfected with an E1 deleted virus, it was observed that purification of rAAV from lysates was associated with substantial loss of lacZ transducing activity when assayed on 293 cells. This drop in rAAV activity was particularly evident in the final step where residual contaminating helper adenovirus was removed by heat inactivation. LacZ transducing activity was recovered by adding adenovirus back to the purified stock or rAAV. These data provided the first indication that adenovirus could substantially enhance the transduction efficiency of rAAV.

Figure 5A:
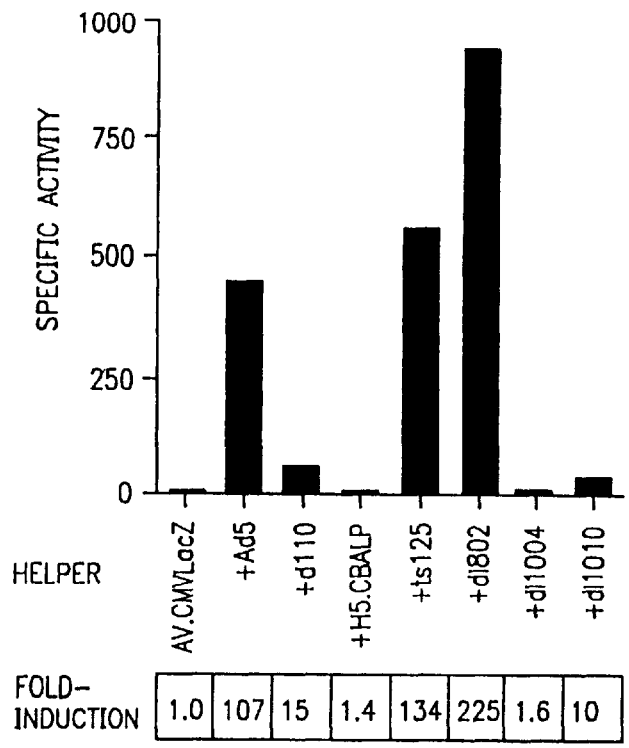
FIG. 5A is a bar graph plotting $\beta$-galactosidase enzyme activity in lysates from infected Hela cells. The horizontal axis indicates the adenoviruses infected into the HeLa cells, with the symbol "+" indicating the addition of the adenovirus to the rAAV, AV.CMVLacZ. The vertical axis indicates intracellular $\beta$-galactosidase specific activity (mUnits/mg protein) using ONPG. Below each bar, the fold-induction in specific activity relative to cells that received the AV.CMVLacZ vector alone is given.

As described in Example 10, a series of complementation groups were generated by mixing different adenovirus early gene mutants with purified LacZ rAAV, referred to as AV.CMVLacZ (see Example 2). These defined mixtures of viruses were analyzed for LacZ transduction on Hela cells (See Examples 12 and 13). An E1 deletion rAd H5.CBALP and the E4 deletion mutant dl1004 provided no significant increase in AV.CMVLacZ transduction (FIG. 5A). However, partial activity could be achieved with E1 and E4 mutants that carried less severe deletions. Both dl110 (E1B-55 kDa deleted) and dl1010 (ORF6 deleted) enhanced transduction to levels that approached those of Ad5, ts125, and dl802 in terms of the number of positive blue cells, but total β-galactosidase activity was substantially lower (FIG. 5A). These results implicate early regions E1 and E4 in the augmentation of rAAV transduction.

The experiments described below also demonstrate that the novel rAAV which incorporates as its conversion gene, as Ad gene, such as E4, can increase transduction efficiency of the rAAV in the absence of a helper virus. As described in more detail in Example 15 below, 293 cells were stably transfected with a genomic fragment of Ad5 spanning E4. This E1/E4 expressing cell line and the parent E1 expressing cell line (293) were infected with rAAV and analyzed for transduction. These experiments demonstrated the significance of the combined expression of E1 and E4(ORF6) in the adenovirus mediated augmentation of rAAV transduction.

In the presence of E1 and E4 expression, rAAV transduction was invariably accompanied by the appearance of ds RF monomers and dimers (Example 14). Importantly, the tight correlation between rAAV vector transduction and the accumulation of duplex forms could be achieved in two different experimental settings; cells infected with E1/E4 expressing adenovirus (FIGS. 8A and 8B), or complementing cell lines (FIG. 8C).

The following examples illustrate the construction and testing of the novel packaging cell lines, the E1/E4 deleted rAd of the present invention and the use thereof, improved methods and second generation recombinant AAV production for gene therapy of the present invention. These examples are illustrative only, and do not limit the scope of the present invention.

EXAMPLE 1

Novel E1a/E1b and E4 Expressing Packaging Cell Lines

A. Construction of E4 ORF 6 Expressing Plasmids

The entire E4 region from Ad5 or an ORF6 minigene were subcloned into a shuttle plasmid that contained a neomycin resistance gene. Two versions of ORF6 minigene were developed that differed in the promoter element. The first used a Zn+2 inducible sheep metallothionine (MT) promoter to drive ORF 6 expression. The second used a dexamethasone-inducible mouse mammary tumor virus (MMTV) promoter.

An exemplary plasmid useful for the construction of a packaging cell line of this invention is pMMTVE4ORF6. The minigene contained in this plasmid is set out in SEQ ID NO: 1, and contains a mouse mammary tumor virus promoter (MMTV) (nucleotides 1–1506 of SEQ ID NO: 1) in transcriptional control of a human E4 ORF 6 gene sequence (nucleotides 1523–2408 of SEQ ID NO: 1), a growth hormone terminator (GH) (nucleotides 2409–3654 of SEQ ID NO: 1), an SV40 origin of replication, plasmid sequences from plasmid pBR322, including a neomycin resistance gene, and an ampicillin resistance gene. The amino acid sequence of ORF 6 is indicated in SEQ ID NO: 2. The various functional fragments of this plasmid may be readily replaced with other conventionally used sequences and are not critical to the design of the plasmid.

Another plasmid useful for the construction of a packaging cell line of this invention is pMTE4ORF6. The DNA sequence of the minigene contained in this plasmid is similar to that of SEQ ID NO: 1, except that the promoter is a sheep metallothionine promoter (MT promoter) [M. G. Peterson et al, cited above].

A plasmid used as a control for the construction of a packaging cell line of this invention is pLTR.E4(−). This plasmid contains the endogenous constitutive retroviral MLV LTR and most of the Ad E4 gene region except that the endogenous E4 promoter and a portion of E4 ORF1 are missing. The other plasmid sequences remain the same as described above.

Still another plasmid useful for the study of the methods of this invention is pLTR.E4, which contains the constitutive MLV LTR and endogenous E4 promoter and an intact E4 gene. The other plasmid sequences remain the same as described above.

To determine whether ORF6 expression was sufficient to enhance rAAV transduction, the inducible metallothionein (MT)-ORF6 minigene was stably transfected into HeLa cells. This new cell line, HeLa(MT-ORF6) was evaluated for LacZ rAAV transduction in response to ORF6 induction as described below. The cell line 293 (MT-ORF6) expresses ORF-6 of the E4 gene of Ad5 from the metallothionine promoter which is relatively inactive at baseline but can be induced with divalent cations. These 293 cells were included to establish the baseline transduction efficiency.

B. Transfections and Selection of Clones

Each of the above-described plasmids was transfected by the calcium phosphate precipitation technique into the human embryonic kidney cell line 293 [ATCC CRL1573] which expresses the product of the adenovirus E1 genes, or into HeLa cells, seeded on 100 mm plates (10 μg plasmid/plate). Twenty four hours post-transfection, cells were harvested and seeded at varying dilutions (1:10–1:100) in 100 mm plates for about 10 days. Seeding media contain G418 Geneticin, BRL) at 1 mg/ml. Resistant colonies that developed were selected using the following assays and expanded. Preliminary analysis of clones was based on enhanced transduction efficiency of a recombinant adeno-associated virus, AV.CMVLacZ, and immunofluorescence localization of Ad E4 protein as described in the following examples.

EXAMPLE 2

Recombinant AAV and AV.CMBLacZ Transduction Enhancement Assay

E1 and E4 Ad gene products are needed for recombinant adeno-associated virus (AAV) function. This primary assay involves seeding the packaging cell lines of Example 1 in 96 well 35 mm culture plates ($2 \times 10^6$ cells/well) and infecting the cells with purified, heat-treated AV.CMVLacZ at an MOI of 1000 virus particles/cell.

A. Preparation of Recombinant AV.CMVLacZ

Figure 10:
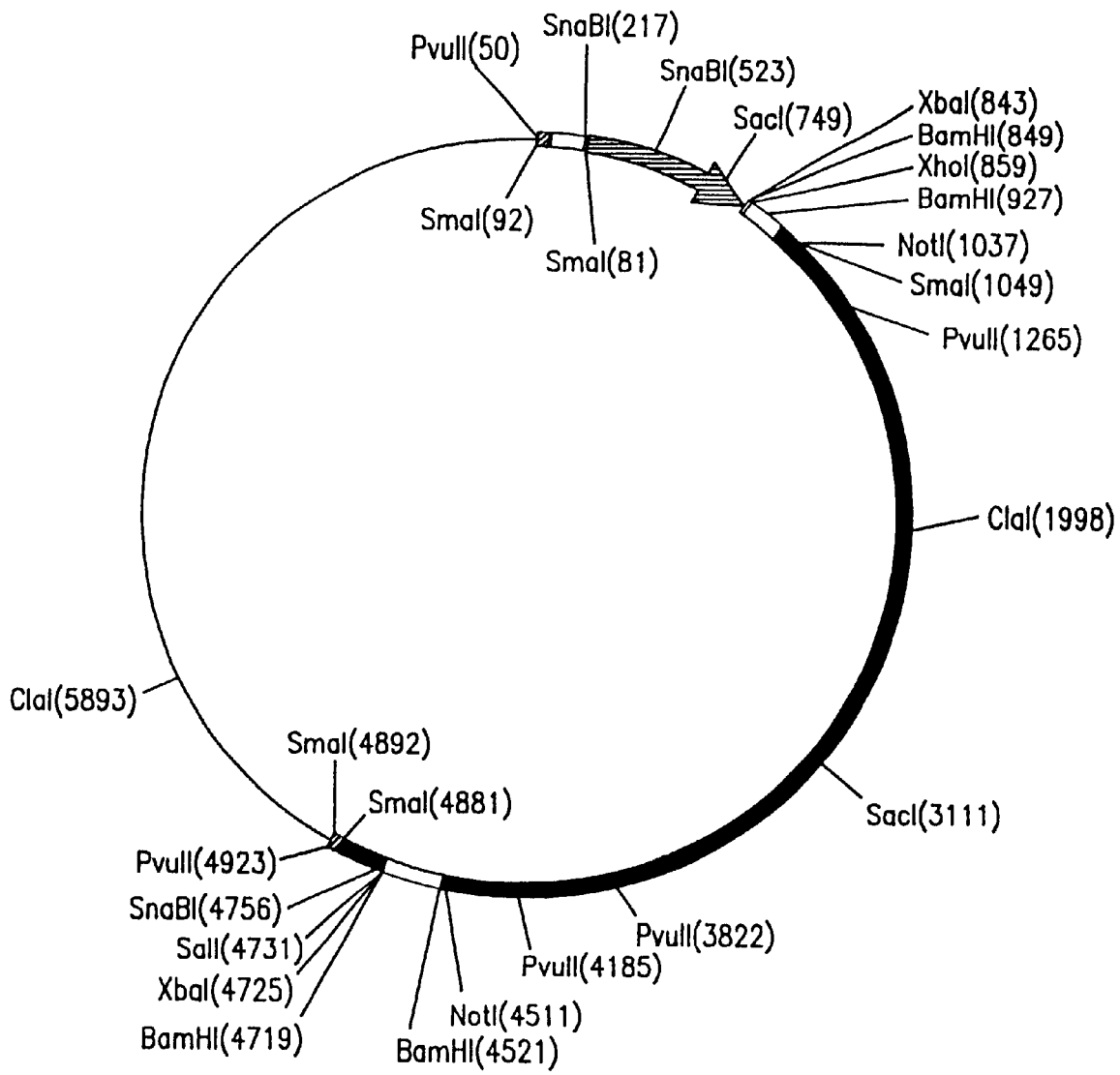
FIG. 10 is a schematic of the plasmid pAV.CMVLacZ [SEQ ID NO: 4].

A recombinant AAV virus was prepared by conventional genetic engineering techniques for the purposes of this experiment. Recombinant AAV was generated by plasmid transfections in the presence of helper adenovirus [Samulski et al, *J. Virol.,* 63:3822–3828 (1989)]. A cis-acting plasmid pAV.CMVLacZ [SEQ ID NO: 4] (see FIG. 10) was derived from psub201 [Samulski et al, *J. Virol.,* 61:3096–3101 (1987)] and contains an *E. coli* β-galactosidase minigene in place of AAV Rep and Cap genes. The 5' to 3' organization of the recombinant AV.CMVLacZ genome (4.9 kb) [SEQ ID NO: 4] includes (a) the 5' AAV ITR (bp 1–173) was obtained by PCR using pAV2 [C. A. Laughlin et al, *Gene,* 23: 65–73 (1983)] as template [nuc. 53–219];

(b) a CMV immediate early enhancer/promoter [Boshart et al, *Cell,* 41:521–530 (1985)] (nuc. 246–839);

(c) an SV40 intron (nuc. 856–987);

(d) *E. coli* β-galactosidase cDNA (nuc. 1039–4512);

(e) an SV40 polyadenylation signal (a 237 Bam HI-BclI restriction fragment containing the cleavage/poly-A signals from both the early and late transcription units (nuc. 4522–4719) and (f) 3' AAV ITR, obtained from pAV2 as a SnaBI-BglII fragment (nuc. 4759–4925). All other nucleotides are plasmid derived.

Rep and Cap genes were provided by a trans-acting plasmid pAAV/Ad [Samulski et al, cited above].

Monolayers of 293 cells grown to 90% confluency in 150 mm culture dishes ($5 \times 10^7$ cells/plate) were infected with H5.CBALP at an MOI of 10. H5.CBALP (also called H5.010ALP) is a rAd that contains an alkaline phosphatase minigene in place of adenovirus E1a and E1b gene sequences (map units 1–9.2 of the Ad5 sequence of GenBank [Accession No. M73260]). The alkaline phosphatase cDNA is under the transcriptional control of a CMV-enhanced β-actin promoter in this virus. This helper virus is described in Goldman et al, *Hum. Gene Ther.,* 6:839–851 (July, 1995); Engelhardt et al, *Hum. Gene Ther.,* 5:1217–1229 (October, 1994); and references cited therein.

Infections were done in Dulbecco's Modified Eagles Media (DMEM) supplemented with 2% fetal bovine serum (FBS) at 20 ml media/150 mm plate. Two hours post-infection, 50 μg plasmid DNA (37.5 μg trans-acting and 12.5 μg cis-acting) in 2.5 ml of transfection cocktail was added to each plate and evenly distributed. Transfections were calcium phosphate based as described [B. Cullen, *Meth. Enzymol.,* 152:684–704 (1987)]. Cells were left in this condition for 10–14 hours after which the infection/transfection media was replaced with 20 ml fresh DMEM/2% FBS. Forty to fifty hours post-transfection, cells were harvested, suspended in 10 mM Tris-Cl (pH 8.0) buffer (0.5 ml/150 mm plate) and a lysate prepared by sonication. The lysate was brought to 10 mM manganese chloride, after which bovine pancreatic DNase I (20,000 units) and RNase (0.2 mg/ml final concentration) were added, and the reaction incubated at 37° C. for 30 minutes. Sodium deoxycholate was added to a final concentration of 1% and incubated at 37° C. for an additional 10 minutes.

The treated lysate was chilled on ice for 10 minutes and solid CsCl added to a final density of 1.3 g/ml. The lysate was brought to a final volume of 60 ml with 1.3 g/ml CsCl solution in 10 mM Tris-Cl (pH 8.0) and divided into three equal aliquots. Each 20 ml sample was layered onto a CsCl step gradient composed of two 9.0 ml tiers with densities 1.45 g/ml and 1.60 g/ml.

Centrifugation was performed at 25,000 rpm in a Beckman SW-28 rotor for 24 hours at 4° C. One ml fractions were collected from the bottom of the tube and analyzed on 293 or 293(E4) cells for LacZ transduction. Fractions containing peak titers of functional AV.CMVLacZ virus were combined and subjected to three sequential rounds of equilibrium sedimentation in CsCl. Rotor selection included a Beckman NVT-90 (80,000 rpm for 4 hours) and SW-41 (35,000 rpm for 20 hours). At equilibrium, AV.CMVLacZ appeared as an opalescent band at 1.40–1.41 g/ml CsCl. Densities were calculated from refractive index measurements. Purified vector was exchanged to 20 mM HEPES buffer (pH 7.8) containing 150 mM NaCl (HBS) by dialysis and stored frozen at −80° C. in the presence of 10% glycerol or as a liquid stock at −20° C. in HBS/40% glycerol.

Purified virus was tested for contaminating H5.CBALP helper virus and AV.CMVLacZ titers. Helper virus was monitored by histochemical staining for reporter alkaline phosphatase activity. A sample of purified virus representing 1.0% of the final product was added to a growing monolayer of 293 cells seeded in a 60 mm plate. Forty-eight hours later, cells were fixed in 0.5% glutaraldehyde/phosphate buffered saline (PBS) for 10 minutes at room temperature, washed in PBS (3×10 minutes) and incubated at 65° C. for 40 minutes to inactivate endogenous alkaline phosphatase activity. The monolayer was allowed to cool to room temperature, rinsed once briefly in 100 mM Tris-Cl (pH 9.5)/100 mM NaCl/5 mM MgCl, and incubated at 37° C. for 30 minutes in the same buffer containing 0.33 mg/ml nitroblue tetrazolium chloride (NBT) and 0.165 mg/ml 5-bromo-4-chloro-3-indolylphosphate p-toluidine salt (BCIP). Color development was stopped by washing the monolayer in 10 mM Tris-Cl (pH 8.0)/5 mM EDTA. Routinely the purification scheme described above removed all detectable H5.CBALP helper virus by the third round of buoyant density ultracentrifugation.

AV.CMVLacZ titers were measured according to genome copy number (virus particles/ml), absorbance at 260 nm ($A_{260}$ particles/ml) and LacZ Forming Units (LFU/ml). Virus particle concentrations were based on Southern blotting. Briefly, a sample of purified AV.CMVLacZ was treated with capsid digestion buffer (50 mM Tris-Cl, pH 8.0/1.0 mM EDTA, pH 8.0/0.5% SDS/Proteinase K 1.0 mg/ml) at 50° C. for one hour to release virus DNA. The reactions were allowed to cool to room temperature, loading dye was added and electrophoresed through a 1.2% agarose gel. Standard quantities of ds AV.CMVLacZ genome were also resolved on the gel.

DNAs were electroblotted onto a nylon membrane, hybridized with a $^{32}P$ random primer labeled restriction fragment, and the resulting blot scanned on a PhosphorImager 445 SI (Molecular Dynamics). A standard curve was generated from the duplex forms and used to extrapolate the number of virus genomes in the sample. LFU titers were generated by infecting indicator cells with limiting dilutions of virus sample. Indicator cells included HeLa and 293 and 293 (E4) lines (described in Example 10 below). Twenty-four hours later, cells were fixed in glutaraldehyde and cells were histochemically stained for *E. coli* β-galactosidase (LacZ) activity as described in J. M. Wilson et al, *Proc. Natl. Acad. Sci. USA,* 85:3014–3018 (1988). One LFU is described as the quantity of virus that is sufficient to cause visually detectable β-galactosidase expression in one cell 24 hours post-infection.

B. Induction of ORF6 Expression

Induction of ORF6 expression with 10 μM dexamethasone or 150 μM zinc sulfate (for negative control, no inducer used) was initiated 2 hours before the addition of virus and continued throughout the duration of the experiment. Twenty-four hours after the addition of virus, cells were harvested, lysates were generated by sonication and analyzed for the β-galactosidase expression (i.e., β-galactosidase activity) and virus DNA as described above. Hirt extracts were prepared from low molecular weight DNA from cell extracts. The preparation of the Hirt extracts and subsequent analysis by Southern hybridization were performed by resort to conventional procedures known to one of skill in the art.

In the absence of the inducers, the packaging cell lines generate lower levels of β-galactosidase in rAAV infected cells. Induction of ORF6 expression with the inducer dexamethasone results in a concomitant rise in AV.CMVLacZ cell transduction to a level that was much greater than the parent 293 line. Expression of E1 alone was insufficient to have an effect in the adenovirus mediated augmentation of rAAV transduction.

Results are demonstrated for certain positive clones in the Table I below (see Example 4). However, for 30 cell lines having an MMTV promoter and ORF6 sequence, 4 demonstrated over 90% blue cells illustrative of LacZ production in the presence of dexamethasone, i.e., 293-27-6, 293-27-17, 293-27-18 and 293-27-28.

EXAMPLE 3

Immunofluorescence Localization of Ad5 Late Protein

Positive clones from the assay of Example 2 were infected with the recombinant E4 deleted adenovirus H5dl1004 and screened for E4 complementation using an immunofluorescence assay for late gene expression. The H5dl1004 virus was obtained from Dr. Ketner of Johns Hopkins University and is described in Bridge and Ketner, *J. Virol.,* 632(2): 631–638 (February 1989), incorporated by reference herein. Because ORF6 of E4 complements late Ad gene expression, specifically in the formation of the hexon and penton fibers of the adenovirus, cell lines containing ORF6 are able to bind with antibody against these proteins.

Each cell line of Example 1 is infected with E4 deleted virus H5dl1004 virus at an MOI of 0.1. The cells were treated with mouse anti-adenovirus FITC-labeled monoclonal antibody to either the hexon or penton fibers in a 1:10 dilution (Chemicon International Inc., Temecula, Calif.). Positive clones were identified by reaction with the antibody.

EXAMPLE 4

Relative Plaquing Efficiency

The cell lines of Example 1, demonstrating strong complementation ability in Example 3, were screened for relative plaquing efficiency of H5dl1004 as compared to W162 cells (an E4-complementing Vero cell line which does not express E1) [Weinberg and Ketner, *Proc. Natl. Acad. Sci. USA,* 80(17):5383–5386 (1983)]. In Table II below, RPE %, i.e., relative plaquing efficiency, represents the titer of H5dl1004 on tested cell lines/titer or H5dl1004 on W162 cells. For example, the RPE of 293 cells is 0.

The positive cell lines selected by all criteria are identified in Table I below, with the results of the assays of Examples 2, 3 and 4.

TABLE I

E1/E4 Double Complementing Cell Lines

| Cell Line | Trans-Gene | Pro-moter | IF/LP | AV.CMV LacZ | RPE % |
|---|---|---|---|---|---|
| 293-10-3 | ORF6 | MT | ++++ | ++++ | 246 |
| 293-39-11 | ORF6 | LTR | ++++ | +++ | 52 |
| 293-84-31 | E4- | LTR | ++++ | ++++ | 179 |
| 293-12-31 | whole E4 | LTR + E4 | ++++ | ++++ | 174 |
| 293-27-6 | ORF6 | MMTV | | +++++ | 327 |
| 293-27-17 | ORF6 | MMTV | | ++++ | 313 |
| 293-27-18 | ORF6 | MMTV | | +++++ | 339 |
| 293-27-28 | ORF6 | MMTV | | ++++ | 261 |

EXAMPLE 5

Construction and Purification of H5.001CBLacZ

The plasmid pAd.CBLacZ was constructed as described in detail in K. Kozarsky et al, *Som. Cell Mol. Genet.*, 19(5): 449–458 (1993), incorporated by reference herein. This plasmid contained a minigene comprising a 5' flanking NheI restriction site, followed by Ad5 sequence m.u. 0–1, followed by an E1 deletion into which is inserted a CMV enhancer/chicken β-actin promoter sequence [T. A. Kost et al, *Nucl. Acids Res.*, 11(23):8287 (1983)], which controls the transcription of the following bacterial β-galactosidase, followed by a poly A sequence and flanked 3' by Ad m.u. 9–16, and another NheI site. In the plasmid, the minigene was flanked on both sides by plasmid sequence containing drug resistance markers.

The plasmid pAd.CBLacZ was linearized with NheI and co-transfected by the calcium phosphate co-transfection method into the novel packaging cell line of Example 1 with ClaI digested H5dl1004 (an Ad5 sequence deleted of from about map unit 92.1 through map unit 98, corresponding to substantially the entire E4 gene).

Figure 2:
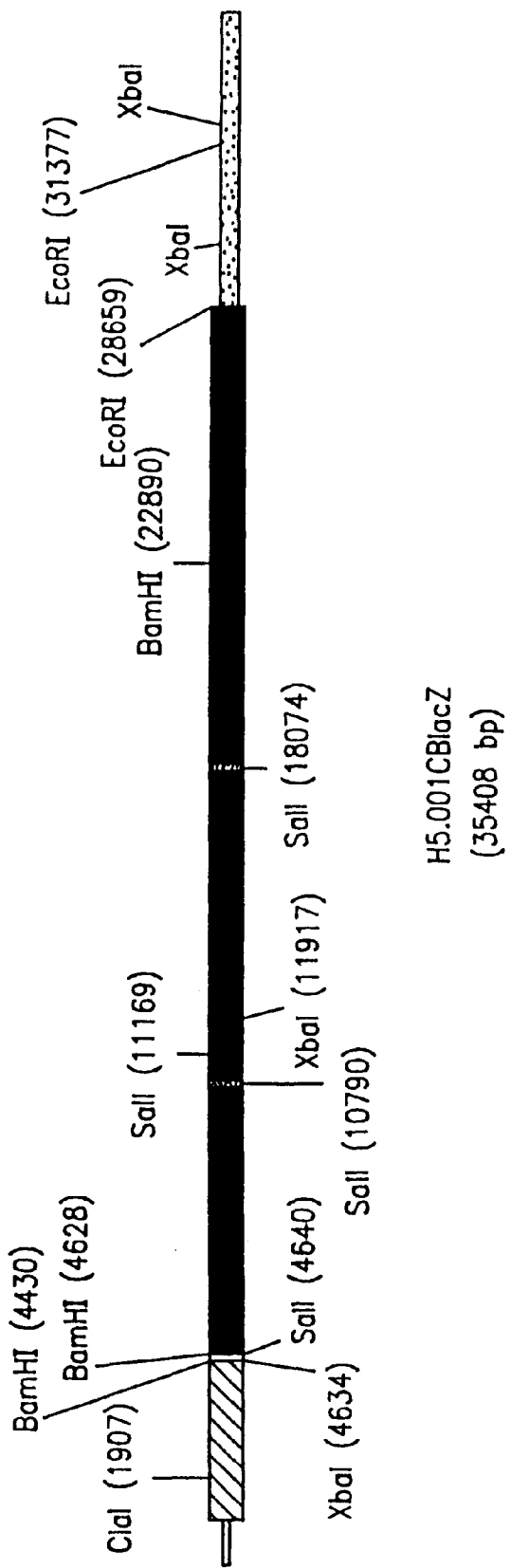
FIG. 2 is a schematic map of rAd H5.001CBLacZ [SEQ ID NO: 3] with indicated restriction endonuclease enzyme sites. The striated bar represents the CBLacZ minigene; the black bar represents Ad5 viral backbone, the crosshatched bar represents Ad E4 deletion.

Homologous recombination occurs in the cell line between these two viral constructs between Ad map units 9–16, resulting in rAd, designated H5.001CBLacZ [SEQ ID NO: 3] (FIG. 2). This rAd contains the sequence from pAd.CBLacZ (including Ad map units 0–1 (nuc. 1–330); CMV enhancer/chicken β-actin promoter (CB) (nucs. 370–928); *E. coli* β-galactosidase (nucs. 945–4429); the polyA (nuc. 4429–4628); and Ad5 map units 9–92.1 and 97.3 to 100 from H5dl1004 (nucs. 4671–35408)). This rAd is thereby functionally deleted, and substantially structurally deleted, of the Ad E1 and E4 genes.

Viral plaques were selected and screened by the β-galactosidase assay [Wilson (1988), cited above] and H5.001CBLacZ was isolated following three rounds of plaque purification. The purified virus was also subjected to cesium chloride density centrifugation and large scale production.

For the following mouse experiments, virus was used after column purification and glycerol was added to a final concentration of 10% (v/v). Virus was stored at—70° C. until use.

EXAMPLE 6

Growth Kinetics of H5.001CBLacZ in Packaging Cell Lines

Figure 3:
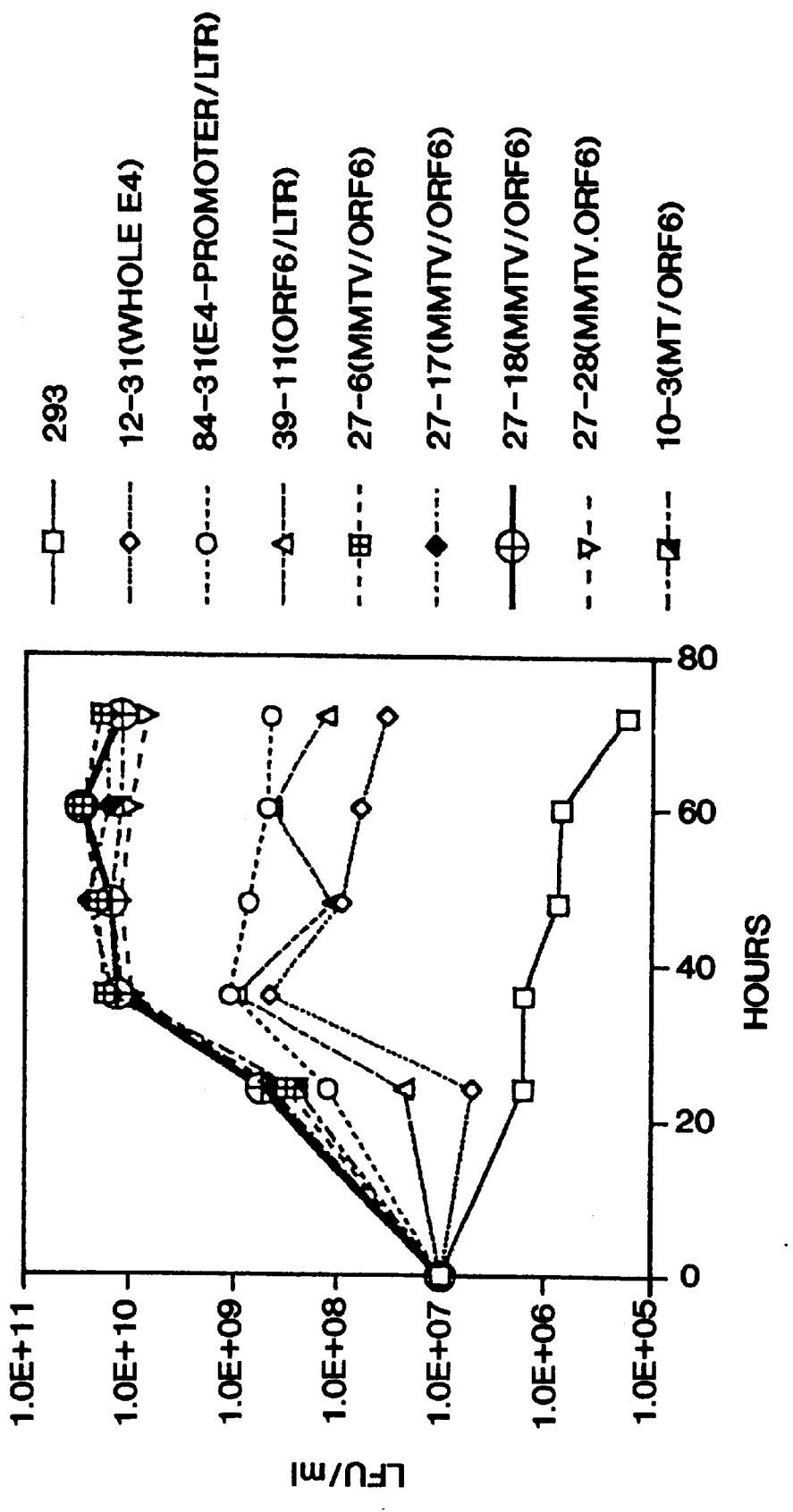
FIG. 3 plots LacZ forming units (LFU)/ml vs time (hours) for E4 complementing cell lines infected with H5.001CBLacZ.
Figure 4A:
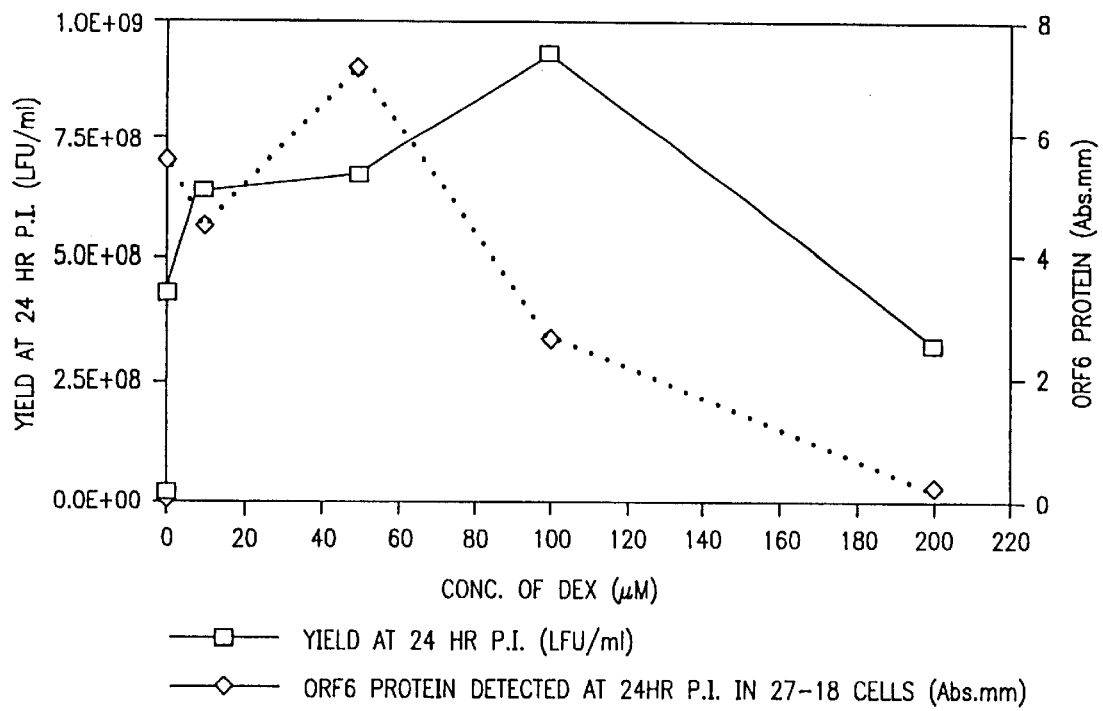
FIG. 4A is a graph of the induction, ORF6 expression and viral production in 293-27-18 packaging cells plotting yield at 24 hours post-infection (pi) in LFU/ml and ORF6 protein (abs.mm) vs. concentration of the inducer, dexamethasone ($\mu$M). Abs.mm is in the intensity of the size of the protein band on a Western blot and reflects absorbance and protein size in mm$^2$. The square is yield at 24 hours pi. The diamond is ORF6 protein detected at 24 hours pi.
Figure 4B:
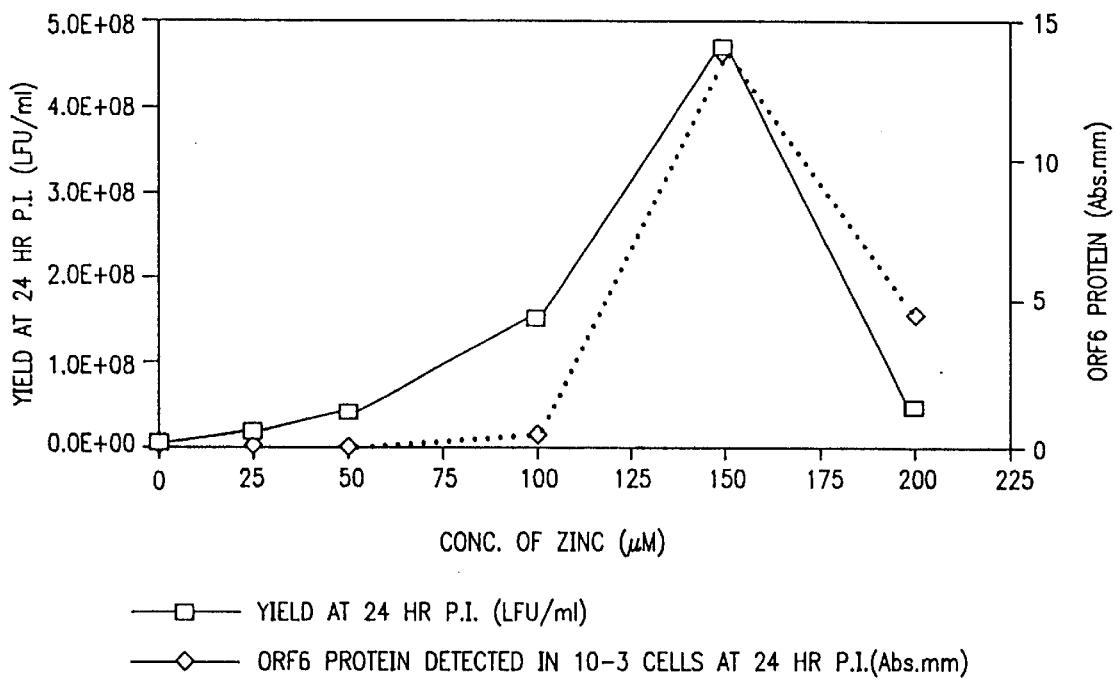
FIG. 4B is a similar graph to that of FIG. 4A, except that the packaging cells are 293-10-3 cells. The symbols are as described for FIG. 4A.

The cell lines identified in Table I were infected with recombinant H5.001CBLacZ at an MOI of 0.5. The growth kinetics of this virus in the E4 complementing cell lines are shown in FIG. 3. Maximum viral yield is reported as LFU/ml in Table II below.

TABLE II

| Cell Line | Maximum Viral Yield |
|---|---|
| 293-10-3 | $2.8 \times 10^{10}$ |
| 293-39-11 | $9.5 \times 10^{8}$ |
| 293-84-31 | $1.1 \times 10^{9}$ |
| 293-12-31 | $4.5 \times 10^{8}$ |
| 293-27-6 | $2.8 \times 10^{10}$ |
| 293-27-17 | $2.5 \times 10^{10}$ |
| 293-27-18 | $2.9 \times 10^{10}$ |
| 293-27-28 | $1.2 \times 10^{10}$ |

When grown in 293-27-18 cells (the E4 ORF6 cell line with MMTV promoter inducible by dexamethasone) the maximum yield of this virus is $2.9 \times 10^{10}$ LFU/ml. Several of the cell lines were passaged between 5 and 20 times and the viral production of the passages remained stable. However, RPE did fall following repeated passages of cells.

EXAMPLE 7

Other Recombinant Adenoviruses

Other related rAds were prepared similarly to H5.001CBLacZ by homologous recombination between pAdCBLacZ and other helper viruses.

As one example, H5.000CBLacZ is a recombinant E1 deleted Ad5 which contains the same minigene as H5.001CBLacZ, but has an intact E4 gene. This rAd was prepared as described by homologous recombination between pAdCBLacZ and a wild-type Ad5.

As another example, H5.010CBLacZ contains the adenovirus map units 0–1, followed by a CMV enhanced, chicken cytoplasmic β-actin promoter, the *E. coli* β-galactosidase gene (lacZ), a polyadenylation signal (pA), and adenovirus type 5 map units 9–100, with a small deletion in the E3 gene (the Ad 5 sub360 backbone). This rAd may be prepared by homologous recombination between the pAdCBLacZ vector and Ad5 virus sub360, which contains a 150 bp deletion within the 14.6 kD protein of the E3 gene. See, e.g., J. F. Engelhardt et al, *Proc. Natl. Acad. Sci., USA*, 91:6196–6200 (June 1994); and Engelhardt et al, *Hum. Gene Ther.*, 5:1217–1229 (October 1994), both incorporated by reference herein.

These rAds were isolated following transfection [Graham, *Virol.*, 52:456–467 (1974)], and were subjected to two rounds of plaque purification. Lysates were purified by cesium chloride density centrifugation as previously described [Englehardt et al, *Proc. Natl. Acad. Sci. USA*, 88:11192–11196 (1991)]. Cesium chloride was removed by passing the virus over a BioRad DG10 column using phosphate-buffered saline.

EXAMPLE 8

LacZ Gene Transfer into Mouse

A. Transfer into Mouse Muscle

Five to six-week old male C57B/6 mice were anesthetized. Anterior tibialis muscles were exposed and directly injected with either rAd H5.000CBLacZ, H5.010CBLacZ or H5.001CBLacZ as follows: 25 μL of purified viral suspension at a stock concentration of $5 \times 10^{11}$ virus particles/mL was injected by inserting the tip of the 33 gauge needle of a 100 μL Hamilton syringe into the belly of the muscle.

Animals were sacrificed on day 4, 14, 28 and 60 post injection. The muscles were dissected and frozen in liquid nitrogen cooled isopentane. Six μM sections were cut in a cryostat, fixed and stained for β-galactosidase activity for 6 hours at 37° C.

While the blue stained rAd was found for each virus in the day 4 and day 14 (most abundant) stains, by day 28, the H5.001CBLacZ clearly demonstrated more virus on day 28. By day 60, the only virus which stained positive was the H5.001CBLacZ.

B. Transfer into Mouse Lung and Circulation

RAd H5.000CBLacZ (control), and H5.001CBLacZ ($1 \times 10^{11}$ viral particles) were administered to six week old C57BL/6 female mice by tail vein injection and trachea installation. The animals were sacrificed and their liver and lung tissues were harvested at days 4, 9, 21, 28 and 35 post-administration. The transgene and viral late gene expression were compared.

At therapeutic doses of virus, there was diminished expression of late viral proteins at all time points in comparison with transgene.

C. Dose Responses in Liver

Dose responses of E4-deleted and E4 intact rAds in the liver of C57BL/6 mice were studied by tail vein administration of $1.5 \times 10^{11}$, $5 \times 10^{10}$, $1.7 \times 10^{10}$, $5.6 \times 10^{9}$, and $1.9 \times 10^{9}$ viral particles and comparing the transgene and viral late gene expression at day 4, 21, 28, 35, and 42 post administration.

At therapeutic doses of virus, there was diminished expression of late viral proteins at all time points in comparison with transgene.

EXAMPLE 9

Other Gene Transfers

A. Human OTC Gene Transfer

The human OTC gene [A. L. Horwich et al, *Science*, 224:1068–174 (1984)] or the human CFTR gene [Riordan et al, *Science*, 245:1066–1073 (1989)] was used to replace the LacZ as the transgene in the recombinant E1/E4 deleted adenoviruses described above, using the techniques analogous for the construction of the above-described LacZ vectors.

The resulting human OTC-containing rAd were administered at an MOI of 10 to 30 to human hepatocytes. The E1/E4 deleted rAd demonstrated less replication and less late gene expression than when the E1/E4 deleted rAds are administered to muscle, as described in the example above. However, the results of this gene transfer are better than comparable transfers with rAds containing only a deletion in the E1 gene or a deletion in the E1 gene and a point mutation in the E2a gene.

Similar results are demonstrated when the transgene is CFTR and the method of administration is intratracheal into lungs.

EXAMPLE 10

Transduction Efficiency of rAAV LacZ AV.CMVLacZ) in HeLa Cells Infected with Ad Mutants A. Viruses The following viruses were employed in this experiment:

(1) Wild-type Ad 5, propagated in 293 cells;

(2) Ad dl110 (an Ad which is deleted of the 55 kb E1B gene) [Babiss et al, *J. Virol.*, 52(2):389–395 (1984) and Babiss and Ginsberg, *J. Virol.*, 50(1):202–212 (1984)], propagated in 293 cells, (3) H5.CBALP (an Ad deleted of its E1A and E1B genes and containing a minigene that expresses alkaline phosphatase from a CMV enhanced β-actin promoter, as described above), propagated in 293 cells, (4) Ad ts125 (an Ad with a temperature sensitive mutation in the E2A gene which encodes the DNA binding protein) [Ensinger and Ginsberg, *J. Virol.*, 10(3):328–339 (1972)], propagated in 293 cells, (5) Ad dl802 (an Ad deleted of its E2a gene), grown in E2A-complementing gmDBP cells as described in Rice and Klessig, *J. Virol.*, 56(3):767–778 (1985);

(6) Ad dl1004 (an Ad deleted of the E4 gene), grown in E4-complementing Vero W162 cells [Weinberg and Ketner, *Proc. Natl. Acad. Sci. USA*, 80(17):5383–5386 (1983)] and (7) Ad dl1010 (an Ad deleted of ORF6 of its E4 gene), grown in E4-complementing Vero W162 cells [Weinberg and Ketner, cited above].

All viruses were purified by two sequential rounds of buoyant density ultracentrifugation in CsCl.

B. Experimental Procedures

HeLa cells seeded in 6 well, 36 mm culture plates ($2 \times 10^6$ cells/well) were infected with wild-type Ad5 or an adenovirus early gene mutant as described in Part A at an MOI of 10 pfu/well. Infections were done in 1.0 ml DMEM/2% FBS. Six hours post-infection, monolayers were washed and 1.0 ml fresh DMEM/2% FBS media containing AV.CMVLacZ at $4 \times 10^9$ virus particles/ml were added. Although the AV.C-MVLacZ virus lot used in these experiments was shown to be free of H5.CLALP helper virus by histochemical staining, the virus sample was subjected to heat treatment (60° C. for 20 minutes) prior to use to ensure the absence of contaminating adenovirus. Two hours later, 1.0 ml of DMEM/115% FBS was added to each well.

Twenty-four hours after the addition of AV.CMVLacZ, cells were harvested. Each test condition was done in triplicate to enable virus transduction to be evaluated in terms of three outputs: histochemical staining for β-galactosidase activity (below), intracellular β-galactosidase specific activity (Example 11), and the molecular form of the virus DNA (Example 12).

HeLa cells were histochemically stained for *E. coli* β-galactosidase (LacZ) activity as described in J. M. Wilson et al, *Proc. Natl. Acad. Sci. USA*, 85:3014–3018 (1988). The different combinations that were tested included cells transfected with AAV vector alone (AV.CMVLacZ), vector plus wild-type Ad5 (+Ad5), vector plus dl110 (+dl110), vector plus Ad mutant H5.CBALP (+H5.CBALP), vector plus Ad mutant ts125 (+ts125), vector plus Ad mutant dl802 (+dl802), vector plus Ad mutant dl1004 (+dl1004), and vector plus Ad mutant dl1010 (+dl1010).

The results were observed in photomicrographs at magnification 10× (not pictured) of histochemical stains for recombinant β-galactosidase activity. The results indicated that wild-type Ad5 and the E2a mutants ts125 and dl802 caused a significant increase in LacZ rAAV transduction as measured by the number of positive blue cells and the degree of stain intensity. Both dl110 (E1B-55 kDa) and dl1010 (ORF6) enhanced transduction to levels that approached those of Ad5, ts125, and dl802 in terms of the number of positive blue cells.

The E1 deletion recombinant H5.CBALP provided no significant increase in AV.CMVLacZ transduction. Expression of E1 alone was insufficient to have an effect in the adenovirus mediated augmentation of rAAV transduction as evidenced by lack of significant increase in transduction obtained with HeLa cells infected with the E4 deletion mutant dl1004. A significant drop in transduction occurred following removal of ORF6 from the E4 region from the coinfecting adenovirus (FIG. 5A).

It is believed that these results demonstrate that the adenoviral gene products, E4 and E1 indirectly promote the formation of ds DNA intermediates that are transcriptionally active.

EXAMPLE 11

Quantitation of Enhanced Vector Transduction (A) A duplicate set of HeLa cells as described in Example 10B were used in this experiment. Twenty-four hours after the addition of AV.CMVLacZ recombinant, for intracellular β-galactosidase assays, cell pellets were suspended in 0.5 ml PBS and sonicated. Cell debris was removed by centrifugation (15,000×g for 10 minutes) and the clarified extract assayed for total protein [M. Bradford, *Anal. Biochem.*, 72(1–2):248–254 (1976) and M. Bradford et al, *Fed. Proc.*, 35(3):274 (1976)] and β-galactosidase activity [Sambrook et al, cited above] using o-nitrophenyl β-D-galactopyranoside (ONPG) as substrate.

FIG. 5A demonstrates the transduction efficiency quantitated by measuring β-galactosidase enzyme activity in the lysates from infected Hela cells and also assayed for total protein. In FIG. 5A, the test condition is shown along the horizontal axis, and intracellular β-galactosidase specific activity (milliunits/mg protein) using ONPG as substrate is plotted on the vertical axis. Below each bar, the fold-induction in specific activity relative to cells that received the AV.CMVLacZ vector alone is given.

The results of FIG. 5A demonstrate that the E2a mutants ts125 and dl802 produced 134-fold and 225-fold increases in β-galactosidase activity, respectively, as compared to that achieved with purified rAAV alone. In comparison, cells infected with wt Ad5 generated 107-fold increase in β-galactosidase activity.

(B) In another experiment, HeLa cells (2×10$^6$) were infected with increasing multiplicities of wild-type Ad5 or the E2 mutant dl802. Six hours post-infection, monolayers were washed and infected with AV.CMVLacZ at 1000 virus particles/cell. Twenty-four hours after the addition of AV.CMVLacZ, cells were harvested and assayed for total protein and β-galactosidase activity.

Figure 5B:
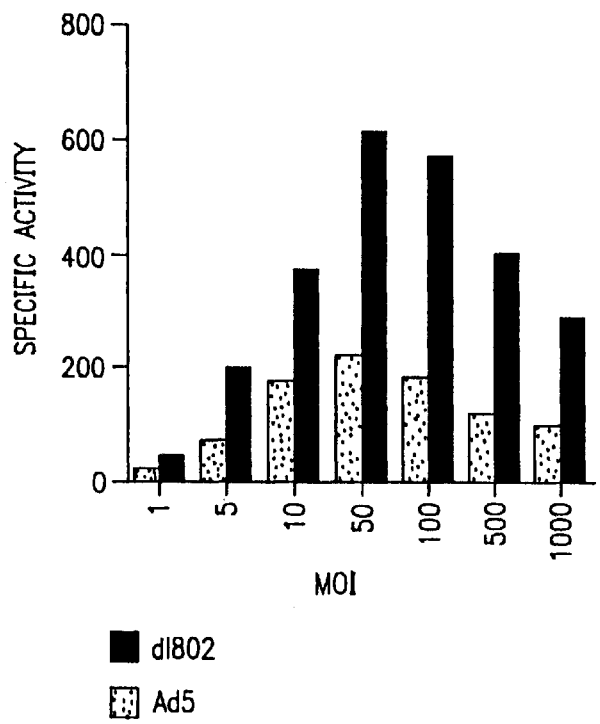
FIG. 5B is a bar graph plotting Ad multiplicity of infection (MOI) in HeLa cells of wild-type Ad5 or the E2 mutant dl802, the cells co-infected with rAAV vs. intracellular $\beta$-galactosidase specific activity. See Example 11.

The results are illustrated in the bar graph of FIG. 5B, in which adenovirus MOI's are given along the horizontal axis, and intracellular β-galactosidase specific activity along the vertical axis. Enhancement of rAAV transduction was proportional to input helper adenovirus from MOIs of 1 to 50 for both wild type Ad5 and dl802. Higher doses of virus were cytopathic, leading to a fall in β-galactosidase expression. Enhanced transduction was achieved when the cells were infected prior to, or at the time of, rAAV infection. The E1 deletion recombinant H5.CBALP and the E4 deletion mutant dl1004 provided no significant increase in AV.CMVLacZ transduction. Both cells infected with dl110 (E1B-55 kDa) and with dl1010 (ORF6) demonstrated substantially lower total β-galactosidase activity than those infected with Ad5, ts125, or dl802.

EXAMPLE 12

Analysis of Low Molecular Weight DNAs in AV.CMVLacZ Transduced Cells

Studies with these early gene mutants of adenovirus suggested that expression of adenoviral genes rather than the virion itself was responsible for enhancement of rAAV transduction. To further investigate these mechanisms and to determine if conversion of ss to ds genome limits the transduction efficiency of rAAV, the molecular state of the rAAV genome was characterized in the infected cells. The relationship between RFm formation and lacZ rAAV transduction was explored in experiments where the dose of coinfecting virus was varied (MOI=1, 5, or 10).

(A) A duplicate set of HeLa monolayers as described in Example 10 were harvested 24 hours after they were transduced with the recombinant AV.CMVLacZ and cultured with or without helper adenovirus.

Episomal DNA was extracted from cell pellets using a modification of the procedure originally described by B. Hirt, *J. Mol. Biol.*, 26:365–369 (1967). Briefly, cells were suspended in 320 ml Tris-Cl (pH 8.0)/10 mM EDTA and SDS added to a final concentration of 1%. The mixture was incubated at 37° C. for 30 minutes. Pronase and proteinase K were added to final concentrations of 500 μg/ml and 20 μg/ml, respectively, and the reaction incubated at 37° C. for 2 hours. Sodium chloride was added to a final concentration of 1.1 M and incubated at 4° C. overnight. The precipitate that developed during the 4° C. incubation was pelleted at 20,000×g for 30 minutes and the clear supernatant carefully removed. The supernatant was extracted once with phenol:chloroform:isoamyl alcohol (25:24:1) followed by chloroform:isoamyl alcohol (24:1). Nucleic acids were precipitated with ethanol. The final pellet was suspended in 50 μl Tris-Cl (pH 8.0)/1.0 mM EDTA.

These Hirt extracts were analyzed by Southern blot hybridization. Samples (5 μl) of each Hirt extract were resolved through a 1.2% agarose gel, electroblotted onto a nylon membrane and hybridized with a $^{32}$P random primer labeled cDNA of the SV40 polyA signal used in AV.CMVLacZ.

An autoradiogram of the experiment of Example 12 (not pictured), identifies and labels bands corresponding to the ss AV.CMVLacZ genome (SS), a monomer replicative form (RFm), and concatomer replicative forms (RFd). Bands corresponding to the ss AV.CMVLacZ genome (SS), a monomer replicative form (RFm), and concatomer replicative forms (RFd) were identified and labeled. To reference the RFm band, a plasmid carrying AV.CMVLacZ was digested to release the entire genome. Autoradiogram exposure times were 14 hours and 69 hours.

In this autoradiogram, the full spectrum of molecular species present during a lytic infection was demonstrated in cells infected with both LacZ rAAV and wild type adenovirus. Both the input as genome (SS) and monomeric and dimeric forms of ds replicative intermediates (RFm and RFd) are present. This contrasts with cells infected with purified rAAV alone, where ss genome is the sole molecular form detected. Analysis of cells coinfected with the adenovirus early gene mutants revealed a direct correlation between formation of ds forms of the rAAV genome and the enhancement of LacZ transduction. Mutant adenoviruses that were ineffective in enhancing rAAV transduction (i.e., the E1 deleted mutant H5.CBALP and the E4 deleted mutant dl1004) failed to promote the formation of ds forms of AAV.

Cells infected with adenovirus deleted of E2a (dl802) or partially deleted of E1 (dl110) or E4 (dl1010) additionally demonstrated a band whose size was identical to the ds replicative monomer (RFm) of the lacZ rAAV genome and whose abundance correlated directly with the expression of β-galactosidase activity (compare results of Example 14 to these described results). Slower migrating concatomers, likely dimers, of duplex rAAV were also detected in the autoradiogram described above.

In the presence of E1 and E4 expression, rAd transduction was invariably accompanied by the appearance of ds RF monomers and dimers.

The high molecular weight band in sample lane +H5.CBALP is helper virus DNA. Helper virus DNA is recognized by the SV40 probe because the CBALP minigene also utilizes the SV40 polyA signal.

(B) In another experiment, HeLa cells were infected with wt Ad5 or the E2 deleted mutant dl802 as described in Example 10B. Monolayers were harvested 24 hours later and analyzed for β-galactosidase activity and RFm synthesis. Monomer bands similar to those shown in the autoradiogram described above were quantitated on a PhosphorImager 445 SI and assigned values (CPM).

Figure 6A:
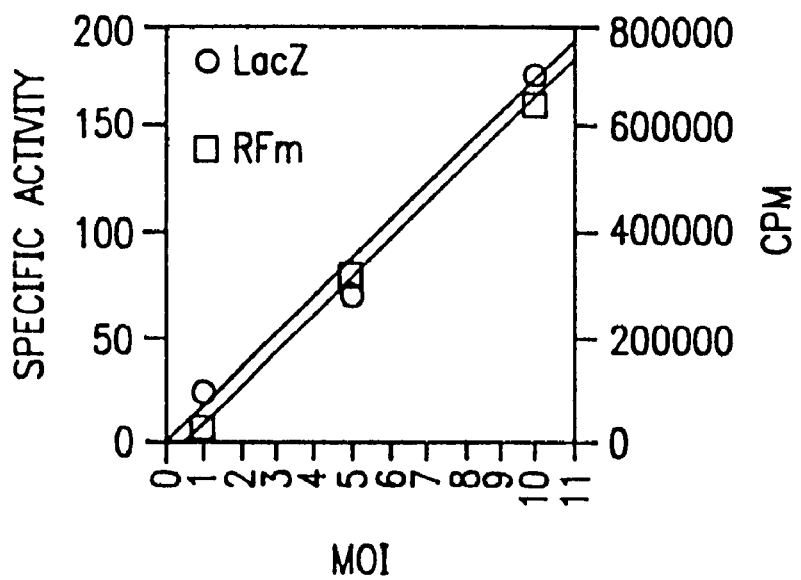
FIG. 6A is a graph in which $\beta$-galactosidase specific activity and counts per minute (CPM) are plotted along the vertical axis and adenovirus MOI's are on the horizontal axis for HeLa cells infected with wtAd5 and rAAV according to Example 12. Data obtained from low MOI (1, 5, and 10) infections are shown.
Figure 6B:
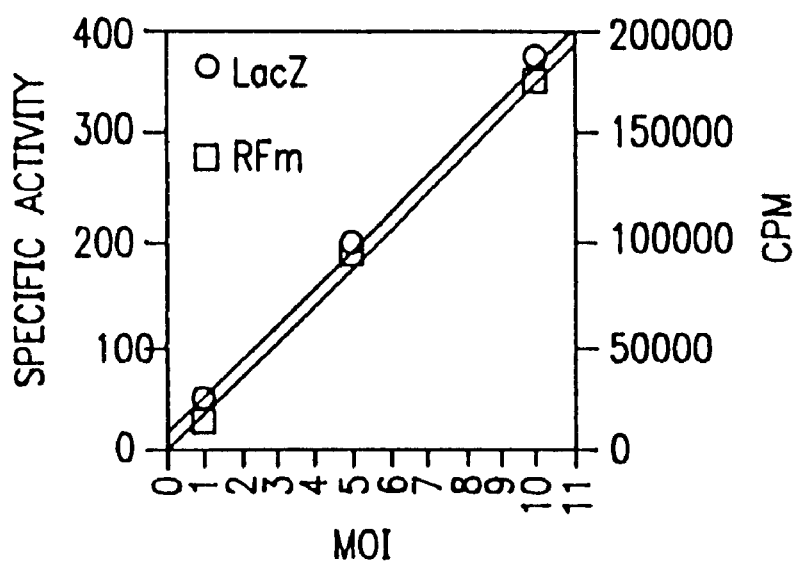
FIG. 6B is a graph similar to that of FIG. 6A except that the cells were infected with Ad mutant dl802.
Figure 8A:
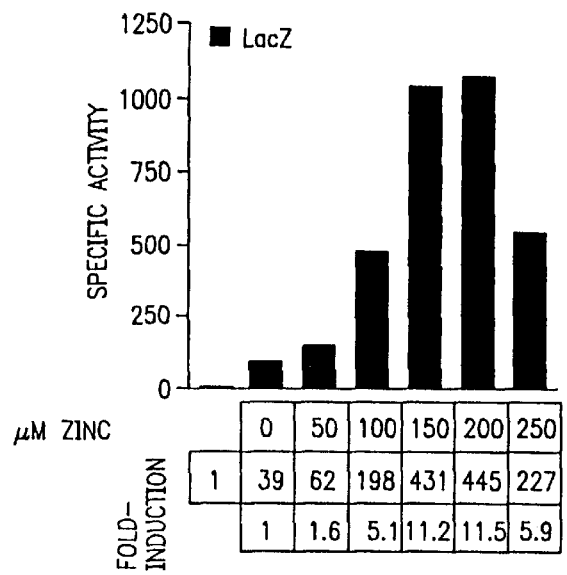
FIG. 8A is a bar graph plotting $\beta$-galactosidase specific activity (mUnits/mg protein) vs. increasing concentration of zinc ($\mu$M) inducer for cell line 293 (MT-ORF6) transduced with AVCMVLacZ (first row below each bar). Also provided is the fold-induction relative to 293 cells (second row below each bar), and the fold-induction relative to 293 (ORF6) cells maintained in the absence of zinc (third row).
Figure 8B:
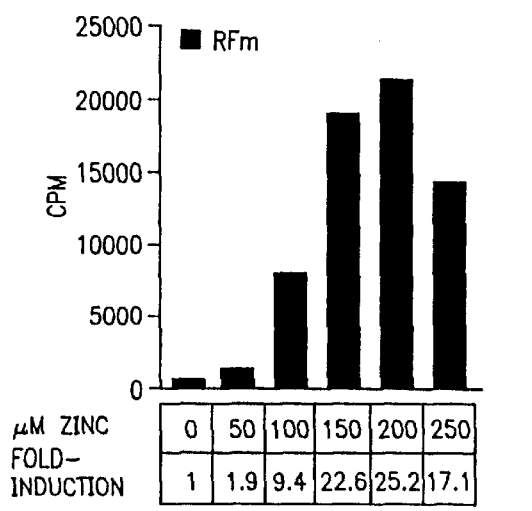
FIG. 8B is a bar graph plotting CPM of duplex monomer replicative form (RFm) of rAAV vs. the concentration of zinc ($\mu$M) used for induction and the fold-induction relative to 293 (ORF6) cells maintained in 0 mM zinc below each bar.
Figure 8C:
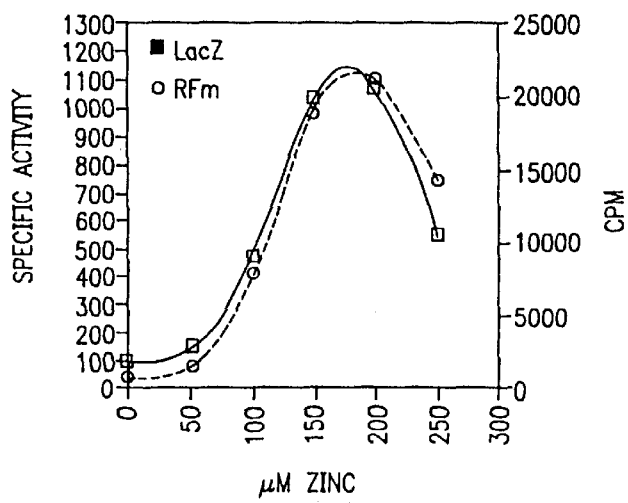
FIG. 8C is a graphical comparison of the induction profiles that describe AV.CMVLacZ transduction efficiency. Specific activity data from FIG. 8A and CPM data of AV.CMVLacZ RFm from FIG. 8B are plotted along the vertical axis, and concentration of zinc sulfate used during the experiment is shown along the horizontal axis.

The results are illustrated in the graphs of FIGS. 8A and 8B, in which β-galactosidase specific activity and CPM are plotted along the vertical axis of each figure. Adenovirus MOI's are given on the horizontal axis of each figure. Data obtained from low MOI infections (1, 5, and 10) are shown. Importantly, the tight correlation between rAAV vector transduction and the accumulation of duplex forms could be achieved in cells infected with E1/E4 expressing adenovirus. The level of β-galactosidase and abundance of RFm increased in proportion to the amount of infecting wild type Ad (FIG. 6A) and dl802 (FIG. 6B). These data suggest that synthesis of an episomal duplex intermediate is an obligatory event in transduction.

EXAMPLE 13

Duplex End—Analysis

The following is a description of a model for leading strand synthesis of a complementary AAV strand in the presence of Rep (+Rep) or absence of Rep (−Rep). Refer to FIGS. 7A–7F. Rep expresses a terminal resolution activity that can convert a duplex structure with closed-ends to an open-ended duplex. In the absence of Rep, terminal resolution is impaired leaving the covalently closed, hairpin structures intact. Under these conditions, hairpins are expected to be found leftward and rightward, since both strands of a rescued ds AAV genome are packaged into virions. FIGS. 7B–7F are a flow chart demonstrating the strategy for identifying the terminal structure of duplex RFm that is synthesized from ss AV.CMVLacZ in response to adenoviral gene expression.

FIG. 7C illustrates a closed end and an open end fragment of rAV.CMVLacZ. FIGS. 7D, 7E and 7F indicate the mixture of open-ended and covalently closed duplex fragments generated by NotI digestion at position 4509 in the absence of terminal resolution. The NotI 4509 digestion provides a convenient means of releasing a 361 bp fragment that contains the right ITR in the context of a hybridization target (i.e. SV40 pA). In the presence of terminal resolution, only the open-ended 361 bp fragment would be expected to be generated (FIG. 7D) by such digestion.

The resulting electrophoretic gel (not pictured), revealed in lane (1) the results of digestion of a plasmid carrying an AV.CMVLacZ cDNA to release the rAAV vector, and subsequent digestion with NotI to release the right terminal 361 bp fragment. In lane (2) a sample of NotI digested Hirt DNA extracted from HeLa cells infected with wild-type Ad5 and transduced with AV.CMVLacZ resulted in the release of two fragments, labeled FormI and FormII. (See, also, FIGS. 8A and 8B). The migration of ss AV.CMVLacZ (SS) and RFm were also seen.

The ds AV.CMVLacZ intermediates that accumulated in cells infected with adenovirus were likely the result of leading strand DNA synthesis, initiating from the duplex region of the vector ITR. In the absence of Rep, this conversion event was anticipated to generate molecules in which one end is open and the other is covalently closed (FIG. 7A). To further characterize the structure of this ds intermediate Hirt extracts from cells coinfected with rAV.CMBLacZ and Ad5 were digested with NotI to release the termini of the ds intermediate which, if left open, would be approximately 361 bp in length. The resulting filters were hybridized with a probe specific for the SV40 polyadenylation signal positioned immediately upstream of the rightward ITR. At least two forms were released from the right end of duplex genomes, one that migrated to a position in the gel that predicted an open-ended conformation (Form II), and a second slower migrating species (Form I). Although this result was consistent with the model (FIGS. 7A–7F), it was difficult to predict with certainty the structure of Form I. Its retarded mobility did, however, suggest a conformation that differed from the open-ended Form II.

EXAMPLE 14

Analysis of AV.CMVLacZ Transduction Efficiency
in 293 Cells Stably Transfected with an Inducible
E4 ORF6 cDNA Cell lines used in this assay were prepared as described in Example 1. 293(MT-ORF6) cells and HeLa(MT-ORF6) cells were seeded in 6 well 35 mm culture plates ($2 \times 10^6$ cells/well) and infected with purified, heat-treated AV.CMVLacZ at an MOI of 1000 virus particles/cell. Induction of ORF6 expression with from none to increasing concentrations of zinc sulfate was initiated 2 hours before the addition of virus and continued throughout the duration of the experiment.

Twenty-four hours after the addition of virus, cells were harvested, lysates were generated by sonication and analyzed for the β-galactosidase expression (i.e., β-galactosidase activity) and virus DNA as described in the preceding examples. Hirt extracts were prepared from low molecular weight DNA from cell extracts. The preparation of the Hirt extracts and subsequent analysis by Southern hybridization were performed similarly to those described in the examples above.

The results of this experiment were as follows:

(1) Specific Activity

The results are illustrated in the bar graph of FIG. 8A. Specific activity (milliunits β-galactosidase/mg protein) is plotted along the vertical axis. Below each bar is given the concentration of zinc used for induction, the fold-induction relative to 293 cells, and the fold-induction relative to 293(ORF6) cells maintained in the absence of zinc. As shown in FIG. 8A, in the absence of Zn+2, the 293(MT-ORF6) cell line generated 39-fold higher levels of β-galactosidase in rAAV infected 293 cells. Induction of ORF6 expression with increasing amounts of $Zn^{+2}$ resulted in a concomitant rise in AV.CMVLacZ cell transduction to a level that was 445-fold greater than the parent 293 line. Expression of E1 alone was insufficient to have an effect in the adenovirus mediated augmentation of rAAV transduction.

The specific activity of β-galactosidase was 196.2 mUnits/mg in E1/E4 expressing 293 cells, compared to 1.0 mUnit/mg in 293 cells that only expressed E1 genes. These experiments support a mechanism for enhancing rAAV transduction that is dependent on the combined expression of both E1 and E4 adenoviral genes.

(2) Molecular Analysis of the AV.CMVLacZ Genome

The duplex monomer replicative form (RFm) was quantitated and the values (CPM) plotted along the vertical axis in the bar graph of FIG. 8B. The concentration of zinc used for induction and the fold-induction relative to 293(ORF6) cells maintained in 0 mM zinc is given below each bar.

An autoradiogram (not pictured) shows the agarose gel resolved Hirt extracts from the AV.CMVLacZ transduced cells described above. A plasmid carrying the AV.CMVLacZ cDNA was digested to release the entire sequence and loaded in a lane of the autoradiogram. The band that appeared in this lane therefore reflected the migration of a monomer duplex replicative form (RFm). The migration of the ss AV.CMVLacZ genome (SS), RFm, and dimers of the duplex replicative form (RFd) were also shown. Lanes of the autoradiogram labeled (0), (50), (100), (150), (200), and (250) contained samples from 293(MT-ORF6) cells that were induced with the indicated concentration of zinc. A Hirt extract from 293 cells (lane labeled 293) transduced with AV.CMVLacZ was also shown.

Analysis of Hirt extracts revealed the presence of the RFm in the rAAV infected 293(MT-ORF6) cells that was not present in similarly infected 293 cells. When the induction profiles (FIGS. 8A and 8B) that describe AV.CMVLacZ transduction efficiency were compared, the results were plotted in FIG. 8C. Specific activity (milliunits β-galactosidase/mg protein) data from FIG. 8A and counts-per-minute data (CPM) of AV.CMVLacZ RFm from FIG. 8B are plotted along the vertical axis, and concentration of zinc sulfate used during the experiment is shown along the horizontal axis.

The two profiles are near mirror images. Importantly, the RFm increased in proportion to the increment in lacZ transducing activity that occurred as ORF-6 expression was induced with $Zn^{+2}$ (FIG. 8C). Similar results were obtained with a 293 derived cell line that expresses ORF6 from the glucocorticoid responsive MMTV promoter.

EXAMPLE 15

Enhanced AV.CMVLacZ Transduction in HeLa Cells Carrying an Inducible ORF6 Minigene HeLa(MT-ORF6) cells ($2\times10^6$) were transduced at an MOI of 1,000 AV.CMVLacZ recombinant particles/cell in absence of zinc sulfate inducer or in the presence of 50, 100, 150, 200, or 250 μM zinc sulfate inducer in the media during transduction. Twenty-four hours later, cells were harvested, cell extracts were prepared by sonication, and analyzed for transgene expression (i.e., β-galactosidase activity). Cell monolayers were histochemically stained for β-galactosidase activity.

The resulting photomicrographs (not pictured) illustrated that histochemical staining revealed an increase in the number of cells scored lacZ positive as the concentration of $Zn^{+2}$ in the medium was raised from 0 to 200 mM. Concentrations of 250 mM zinc were found to be toxic to the cells.

Figure 9:
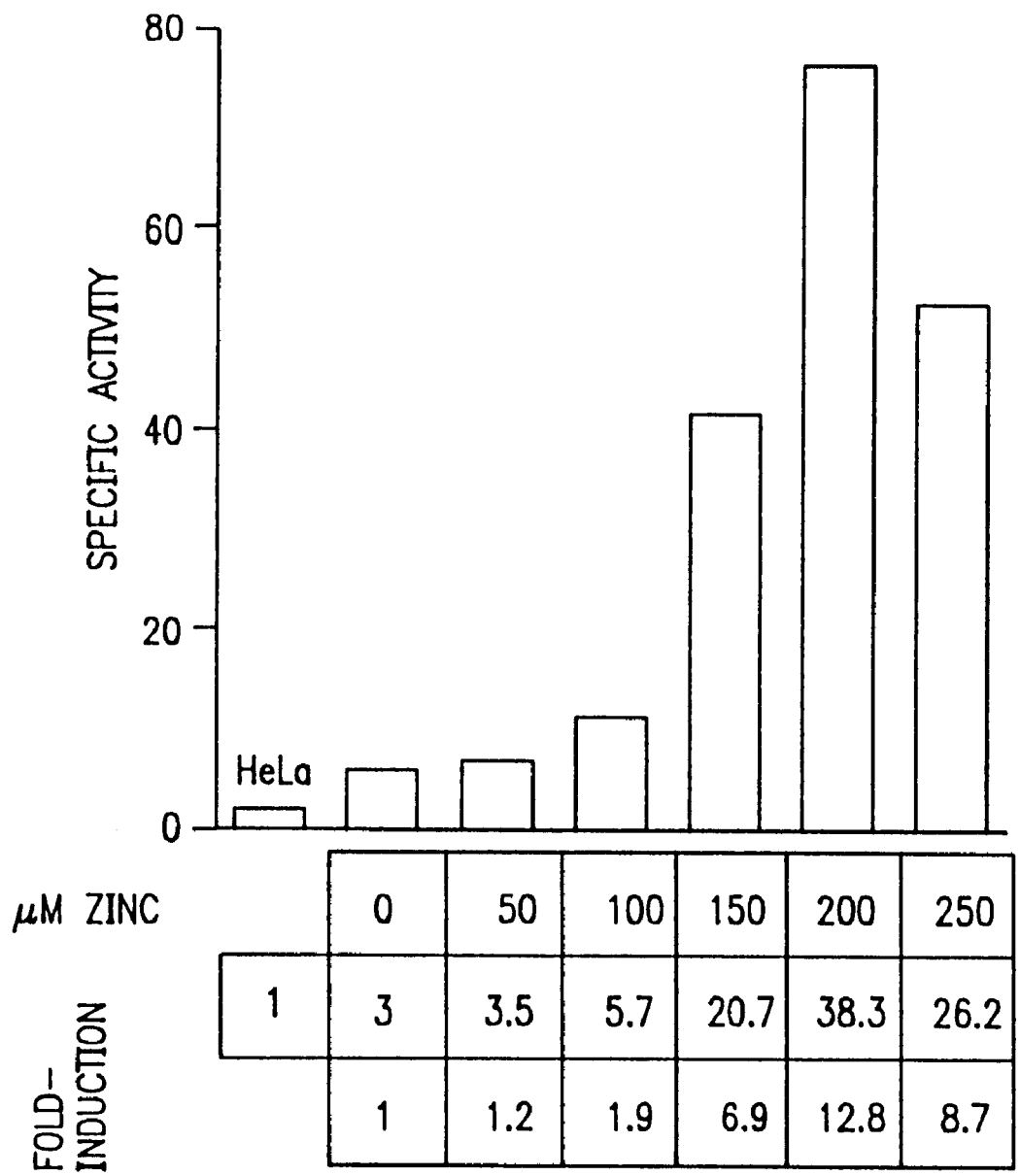
FIG. 9 is a bar graph plotting specific activity (milliunits $\beta$-galactosidase/mg protein) vs the concentration of zinc used for induction (first row under the horizontal axis), the fold-induction relative to HeLa cells (second row), and the fold-induction relative to HeLa (Mt-ORF6) cells maintained in the absence of zinc (third row), for the HeLa(MT-ORF6) cells transduced at a MOI of 1,000 AV.CMVLacZ virus particles/cell in the absence of zinc sulfate inducer or in the presence of 50, 100, 150, 200 or 250 $\mu$M zinc sulfate inducer.

Specific activity (milliunits β-galactosidase/mg protein) is plotted in FIG. 9 along the vertical axis. Below each bar is given the concentration of zinc used for induction, the fold-induction relative to HeLa cells, and the fold-induction relative to HeLa(Mt-ORF6) cells maintained in the absence of zinc. Histochemical staining revealed an increase in the amount of β-galactosidase in lysates as the concentration of $Zn^{+2}$ in the medium was raised from 0 to 200 mM.

EXAMPLE 16

Southern Blot Analysis of Low Molecular Weight DNAs from AV.CMVLacZ Transduced HeLa(MT-ORF6) Cells Following Induction of E4ORF6

Hirt extracts were prepared from HeLa(MT-ORF6) cells transduced with AV.CMVLacZ as described in Example 15 in the presence of increasing concentrations of $Zn^{+2}$ to determine whether synthesis of duplex intermediates contributed to the augmentation in AV.CMVLacZ transduction.

Samples of HeLa(MT-ORF6) cells that were induced with a concentration of zinc sulfate (0, 50, 100, 150, 200, and 250) were resolved on a 1.2% agarose Southern gel (not pictured), transferred to a nylon membrane, and hybridized with a LacZ-specific probe. One lane contained a plasmid encoding AV.CMVLacZ that was digested to release the entire genome. Bands corresponding to the ss AV.CMVLacZ genome (SS), duplex monomers (RFm), and duplex dimers (RFd) were indicated on the gel.

Southern analysis indicated that Hela and uninduced Hela(MT-ORF6) cells demonstrated a single band on Southern blots which comigrated with the ss genome. Induction of ORF-6 resulted in the appearance of detectable levels of ds monomer but only at higher concentrations of Zn+2. A band comigrating with the RFd was present in all cell preparations, the relevance of which is unclear since the monomer is a likely precursor to the dimer.

EXAMPLE 17

Effect of Adenovirus Infection on In Vivo AV.CMVLacZ Targeting Efficiency to Murine Liver The impact of adenoviral gene expression on rAAV transduction in murine liver was studied by sequentially infusing into the portal vein early gene mutants of adenovirus followed by rAAV.

Balb/c mice, 4- to 6-weeks old [Jackson Laboratories, Bar Harbor, Me.] were anesthetized by an intraperitoneal injection of ketamine (70 mg/kg) and xylazine (10 mg/kg). For liver studies, a 1 cm left flank incision was made and the spleen exposed.

Samples of purified, heat-treated AV.CMVLacZ in 50 μl HBS ($1\times10^{11}$ virus particles) were used alone or spiked with helper adenovirus containing $2\times10^{10}$ $A_{260}$ particles of purified dl1004, H5.CBALP, or ts125 in a final volume of 50 μl. The dose of adenovirus was sufficient to transduce>25% of hepatocytes. The virus mixture was injected just beneath the splenic capsule and the abdomen was closed with 3-0 vicryl.

Necropsies were performed 3 days post-infusion and tissue frozen in O.C.T. embedding compound. Frozen section (6 μm) (LacZ+ALP) were prepared and histochemically stained for β-galactosidase enzyme and alkaline phosphatase activity. Sections were counterstained with neutral red and mounted.

A β-galactosidase positive hepatocyte targeted with AV.CMVLacZ at magnification 20× was obtained. Histochemical analyses of liver tissue harvested 3 days after gene transfer demonstrated that administration of $10^{11}$ particles of purified rAV.CMVLacZ alone into the portal vein was not associated with appreciable gene transfer (<0.01% of cells), confirming the inherent inefficiency of the rAAV system.

Preinfusion with E4 deleted virus had no impact on rAAV transduction in mouse lever, whereas E1 deleted virus demonstrated a modest increment in lacZ positive hepatocytes to about 0.1%. The most significant increase in rAAV transduction occurred following infusion of the E2a adenovirus mutant ts125 with lacZ expression detected in 10–25% of hepatocytes. A direct relationship between adenovirus gene expression and rAAV transduction was demonstrated in animals infused with both lacZ rAAV and the ALP expressing E1 deleted virus. The dose of adenovirus was reduced 10-fold to minimize the coincidental occurrence of coinfection. Histochemical studies demonstrated co-localization of ALP and β-galactosidase in the majority of β-galactosidase expressing hepatocytes.

EXAMPLE 18

Effect of Adenovirus Infection on In Vivo AV.CMVLacZ Targeting Efficiency to Murine Lung Experiments described in Example 17 for mouse liver were adapted for the study of rAAV mediated gene transfer to mouse lung. For lung experiments, anesthetized Balb/C animals were intubated as described in DeMatteo et al, *Transplantation (Baltimore)*, 59(5):787–789 (1995). Briefly, a midline 2 cm skin incision was made in the neck to expose the trachea. A 2 inch 18 gauge angiocatheter was passed through the mouth, positioned in the midportion of the trachea, and connected to a rodent ventilator (#55-3438 Harvard). Polyethylene (PE#10, Intramedic) was fed through the catheter via a side port and advanced beyond the tracheal bifurcation. Using a Hamilton syringe, virus samples (30 μl) were slowly infused into the lung through the polyethylene tubing. Samples contained the same formulation of purified, heat-treated AV.CMVLacZ with or without helper adenovirus, as described for liver injections.

Tissue was harvested 72 hours post-infusion. Frozen sections were histochemically stained for β-galactosidase activity and counterstained with neutral red.

Frozen sections from lung (AV.CMVLacZ) showed a β-galactosidase positive airway epithelial cell targeted with AV.CMVLacZ. Similar studies were performed in the murine model of lung-directed gene transfer. Adenoviruses were instilled into the trachea prior to the instillation of rAAV. Analysis of lung tissue 3 days later revealed only a rare β-galactosidase positive cell in animals instilled with rAAV alone. No detectable enhancement of rAAV transduction was noted in animals preinstilled with adenovirus deleted of either E1 or E4. Substantial enhancement of transduction was achieved in conducting airway and alveolar cells of animals administered the E2a mutant adenovirus.

These experiments in murine models of gene therapy directed to liver and lung verified that the efficiency of rAAV transduction is low due limited conversion of the input ss genome to a transcriptionally active ds intermediate, and that this conversion is facilitated by expression of adenovirus E1 and E4 gene products.

EXAMPLE 19

Second Generation rAAV with Regulated Minigene Capable of Enhancing Transduction The experiments described in previous examples illustrated the following principles: 1) purified rAAV is a relatively inefficient gene transfer vehicle in vitro and in vivo and 2) the rate limiting step in transduction is not viral entry but rather conversion of the virion's ss DNA genome to a transcriptionally active ds DNA genome. Adenovirus can substantially enhance transduction through expression of a subset of its genes. It does this by promoting conversion of the virion's genome to its ds form. One approach to accomplish this is to incorporate into the recombinant AAV genome a minigene that expresses the minimal adenoviral genes necessary to enhance transduction, i.e., the ORF6 region of E4.

Two approaches have been considered in designing this modified rAAV. The first strategy is based on a rAAV genome that has two transcriptional units in series, one expressing the therapeutic gene and the other expressing its E4 ORF6 from a constitutive promoter. While this may, in fact, be useful in many situations, constitutive expression of ORF6 may be detrimental to the cell and potentially could elicit a destructive immune response.

The second version of this rAAV includes the therapeutic minigene in addition to the ORF6 transcriptional unit which, in this case, is expressed from an inducible promoter. When this second gene rAAV is administered to the cells (ex vivo strategies) or to the patient (in vivo strategies), the inducing agents are administered at the time of gene transfer or soon thereafter. If the ds genomic form or its integrated derivative is stable, the induction of ORF6 will only be necessary at the time of gene transfer into the recipient cell. Following this, its inducing agent will be withdrawn and the ORF6 gene will be turned off.

Figure 11:
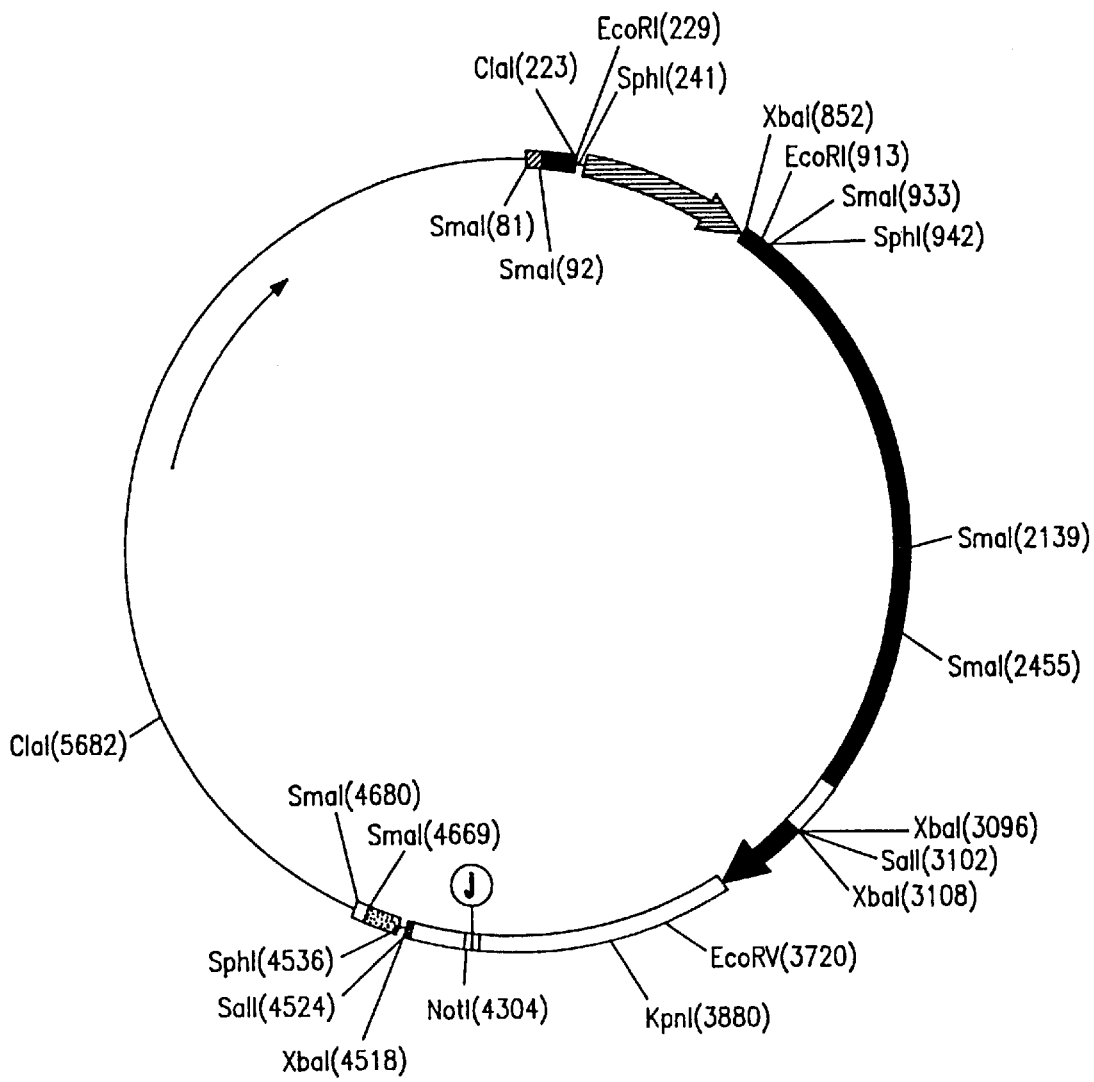
FIG. 11 illustrates plasmid pAV.CMVALP.GRE-ORF6 [SEQ ID NO: 5].

An rAAV that illustrates this concept of inducible ORF6 has been constructed and tested in vitro. A schematic of the vector pAV.CMVALP.GRE-ORF6, is shown in FIG. 11 and its sequence is illustrated in SEQ ID NO: 5. This second generation construct contains flanking 5' and 3' AAV ITR sequences. The human placental alkaline phosphatase cDNA (ALP) is included in a minigene in which the promoter from the immediate early gene of cytomegalovirus drives the transcription. A second transcriptional unit is cloned between the ITRs in series and in direct orientation with the alkaline phosphatase minigene. The second transcriptional unit expresses the Ad5-E4-ORF6 from a glucocorticoid dependent promoter (GRE) with an SV40 polyadenylation signal. This is called a second generation rAAV construct.

Specifically, pAV.CMVALP.GRE-ORF6 [SEQ ID NO: 5] generates a novel rAAV containing the LacZ transgene and the Ad E4 ORF 6 which facilitates ss to ds conversion of rAAV. The plasmid includes a flanking AAV 5' ITR sequence (nucs. 53–219); CMV enhancer/promoter (nucs. 255–848); human placenta alkaline phosphatase cDNA (ALP) (nucs. 914–2892); SV40 polyA (nucs. 2893–3090); GRE promoter (nucs. 3114–3393); Ad5 E4-ORF6 cDNA (nucs. 3402–4286); SV40 polyA (nucs. 4315–4512); and 3' AAV ITR (nucs. 4547–4713). All other nucleotides are plasmid derived.

The second generation rAAV construct was used to produce and purify rAAV virions which were exposed to HeLa cells that were left untreated or incubated with dexamethasone. In the absence of dexamethasone, (a condition under which little ORF6 should be expressed), little transduction was observed as measured by expression of the alkaline phosphatase gene. Cells incubated in dexamethasone expressed in ORF6 gene and the transduction efficacy was enhanced at least 5-fold. This provides evidence to support that a gene product expressed from the rAAV can function in cis to enhance expression of the transgene.

EXAMPLE 20

Application to Bone Marrow Directed Gene Therapy

Bone marrow directed gene therapy represents the paradigm of ex vivo gene therapy where the target cell is the hematopoietic stem cell. The basic strategy is to incorporate (i.e., integrate) a therapeutic minigene into the chromosomal DNA of hematopoietic stem cells which are transplanted into a recipient patient whose own bone marrow has been ablated allowing repopulation of its lymphohematopoietic system with progeny of the genetically corrected stem cell.

The problem with this approach has been efficiently transfecting genes into stem cells. Most studies of bone marrow directed gene therapy have utilized recombinant retroviruses which have not been very efficient. One problem is that retroviruses integrate their provirus only when the target cell is dividing. Unfortunately, most stem cells in vitro are quiescent and not dividing. rAAV holds the promise of integrating the provirus more efficiently into non-dividing stem cells. However, purified rAAV is not very efficient with respect to integration when used alone. In cultured cells, integration is observed in less than 1% of the cells. The same conditions that activate the conversion of ss to ds genome also enhance the integration of the ds intermediate into the chromosomal DNA.

Therefore, a desirable application of the methods and compositions of this invention is in bone marrow directed gene therapy. According to this method, stem cells are genetically modified with rAAV and an inducing agent ex vivo using the constructs and methods described above (see e.g., Example 19). Genetically modified stem cells are subsequently transplanted by conventional techniques.

Numerous modifications and variations of the present invention are included in the above-identified specification and are expected to be obvious to one of skill in the art. Such modifications and alterations to the compositions and processes of the present invention, such as selections of different transgenes and plasmids for the construction of the packaging cell lines and rAds, or the selection or dosage of the viruses or immune modulators, are believed to be encompassed in the scope of the claims appended hereto.

---

What is claimed is:

1. A method of enhancing conversion of single-stranded AAV to double-stranded AAV, said method comprising the step of culturing a host cell containing:
   (a) a nucleic acid molecule comprising AAV 5' inverted terminal repeats (ITRs), a transgene under the control of regulatory sequences directing expression thereof, and AAV 3' ITRs;
   (b) a nucleic acid molecule comprising a nucleic acid sequence encoding adenovirus E4 ORF6, wherein the E4 ORF6 is under the control of heterologous regulatory sequences directing expression thereof;
   (c) a nucleic acid molecule comprising a nucleic acid sequence encoding rep under the control of regulatory sequences directing expression thereof;
   (d) a nucleic acid molecule comprising nucleic acid sequence encoding cap under the control of regulatory sequences directing expression thereof.

2. The method according to claim 1, wherein the E4 ORF6 is under the control of regulatory sequences comprising a constitutive promoter.

3. The method according to claim 1, wherein the E4 ORF6 is under the control of regulatory sequences comprising an inducible promoter.

4. The method according to claim 1, wherein the nucleic acid molecule comprising the nucleic acid sequence encoding adenovirus E4 ORF6 is stably integrated in the host cell.

5. The method according to claim 1, wherein the host cell is cultured in vitro.

6. The method according the claim 1, further comprising a step of introducing the nucleic acid molecule comprising the nucleic acid sequence encoding rep into the host cell in trans.

7. The method according to claim 1, further comprising a step of infecting the host cell with wild-type helper virus.

8. The method according to claim 1, wherein the host cell further comprises a nucleic acid molecule comprising nucleic acid sequence encoding an adenovirus E1 gene.

9. The method according to claim 3, wherein said inducible promoter is selected from the group consisting of metallothionine promoter and the mouse mammary tumor virus promoter.

10. The method according to claim 5, further comprising a step of recovering rAAV from the host cell.

11. The method according to claim 8, wherein the nucleic acid molecule comprising a nucleic acid sequence encoding adenovirus E4 ORF6 further comprises a nucleic acid sequence encoding an adenovirus E1 gene.

12. The method according to claim 11, wherein the nucleic acid molecule comprising nucleic acid sequences encoding adenovirus E1 and E4 ORF6 further comprises the 5' AAV ITR, transgene, and 3' AAV ITR.

* * * * *